US007531008B2

(12) United States Patent
Lagrange

(10) Patent No.: US 7,531,008 B2
(45) Date of Patent: May 12, 2009

(54) USE OF AT LEAST ONE CATIONIC CYANIN DERIVATIVE FOR DYEING THE HAIR, COMPOSITION CONTAINING IT, PROCESS FOR TREATING KERATIN FIBERS USING THE COMPOSITION, AND DEVICE THEREFOR

(75) Inventor: Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 62 days.

(21) Appl. No.: 11/606,115

(22) Filed: Nov. 30, 2006

(65) Prior Publication Data

US 2007/0143936 A1 Jun. 28, 2007

Related U.S. Application Data

(60) Provisional application No. 60/771,432, filed on Feb. 9, 2006.

(30) Foreign Application Priority Data

Nov. 30, 2005 (FR) .................................. 05 12158

(51) Int. Cl.
*A61Q 5/10* (2006.01)
(52) U.S. Cl. ........................ 8/405; 8/406; 8/409; 8/423; 8/435; 8/565; 8/566; 8/568; 8/570; 8/571; 8/572
(58) Field of Classification Search ..................... 8/405, 8/406, 409, 423, 435, 565, 566, 568, 570, 8/571, 572
See application file for complete search history.

(56) References Cited

U.S. PATENT DOCUMENTS

| 2,528,378 | A | 10/1950 | Mannheimer |
| 2,781,354 | A | 2/1957 | Mannheimer |
| 2,798,053 | A | 7/1957 | Brown |
| 2,923,692 | A | 2/1960 | Ackerman |
| 3,915,921 | A | 10/1975 | Schlatzer, Jr. |
| 4,237,243 | A | 12/1980 | Quack et al. |
| 4,509,949 | A | 4/1985 | Huang et al. |
| 4,823,985 | A | 4/1989 | Grollier et al. |
| 5,089,578 | A | 2/1992 | Valint et al. |
| 5,708,151 | A | 1/1998 | Möckli |
| 5,792,221 | A | 8/1998 | Lagrange et al. |
| 5,914,373 | A | 6/1999 | Glancy |
| 6,120,780 | A | 9/2000 | Dupuis et al. |
| 6,822,039 | B1 | 11/2004 | Monfreux-Gaillard et al. |
| 7,066,966 | B2 | 6/2006 | Cottard et al. |
| 2003/0124079 | A1 | 7/2003 | Mougin et al. |
| 2004/0078906 | A1 | 4/2004 | Plos et al. |
| 2004/0141943 | A1 | 7/2004 | Mougin et al. |
| 2004/0187229 | A1 | 9/2004 | Guerin et al. |

FOREIGN PATENT DOCUMENTS

| EP | 0 395 282 | B1 | 10/1990 |
| EP | 0 503 853 | B1 | 9/1992 |
| EP | 0 714 954 | B1 | 6/1996 |
| EP | 0 750 899 | A2 | 1/1997 |
| EP | 0 815 828 | B1 | 1/1998 |
| EP | 1 415 643 | A1 | 5/2004 |
| FR | 2 416 723 | | 9/1979 |
| FR | 2 586 913 | A1 | 3/1987 |
| FR | 2 692 572 | A1 | 12/1993 |
| FR | 2 811 933 | A1 | 1/2002 |
| FR | 2 820 032 | A1 | 8/2002 |
| FR | 2 849 371 | A1 | 7/2004 |
| WO | WO 95/01772 | | 1/1995 |
| WO | WO 95/15144 | | 6/1995 |
| WO | WO 00/31154 | | 6/2000 |

OTHER PUBLICATIONS

STIC Search Report dated Apr. 8, 2008.*
Charles Zviak, "Sciences Des Traitements Capillaires,", published by Masson, pp. 215 and 278 (1988).
Martin Sczepan et al., "The role of internal twisting in the photophysics of stilbazolium dyes," Phys. Chem. Chem. Phys., vol. 3, pp. 3555-3561 (2001).
M.R. Porter, BSc, PhD, CChem, MRSC, "Handbook of Surfactants," Blackie & Son, Ltd., Glasgow and London, pp. 116-178 (1991).
G. Fonnum et al., "Associative thickeners. Part I: Synthesis, rheology and aggregation behavior," Colloid & Polymer Science, vol. 271, No. 4, pp. 380-389 (1993).
Yotaro Morishima, "Self-Assembling Amphiphilic Polyelectrolytes and Their Nanostructures," Chinese Journal of Polymer Science, vol. 18, No. 40, pp. 323-336 (2000).
Tetsuya Noda et al, "Micelle Formation of Random Copolymers of Sodium 2-(Acrylamido)-2-methylpropanesulfonate and a Nonionic Surfactant Macromonomer in Water As Studied by Fluorescence and Dynamic Light Scattering," Macromolecules, vol. 33, pp. 3694-3704 (2000).
Tetsuya Noda et al., "Solution Properties of Micelle Networks Formed by Nonionic Surfactant Moieties Covalently Bound to a Polyelectrolyte: Salt Effects on Rheological Behavior," Langmuir, vol. 16, pp. 5324-5332 (2000).

(Continued)

*Primary Examiner*—Eisa B Elhilo
(74) *Attorney, Agent, or Firm*—Finnegan, Henderson, Farabow, Garrett, & Dunner, L.L.P.

(57) ABSTRACT

The present disclosure relates to the use of a direct dye as an agent for lightening keratin fibers, such as, for example, human keratin fibers, and/or as an agent for coloring the said fibers. The disclosure also relates to a composition comprising, in a cosmetically acceptable medium, at least the direct dye. The disclosure also relates to a process for treating keratin fibers, including human keratin fibers, using the above-mentioned composition, and also to a device comprising it. Finally, the disclosure relates to the use of the composition according to the disclosure as a coloring agent and/or as an optical lightening agent for the fibers.

48 Claims, No Drawings

OTHER PUBLICATIONS

Tetsuya Noda et al., "Stimuli-Responsive Amphiphilic Copolymers of Sodium 2-(Acrylamido)-2-Methylpropanesulfonate and Associative Macromonomers," Polymer Preprints, vol. 40, No. 2, pp. 220-221 (1999).

Database CAPLUS [Online], Chemical Abstracts Service, Columbus, Ohio, US; 2000, XP-002399475, Database accession No. 1999:806382.

Database.CAPLUS [Online], Chemical Abstracts Service, Columbus, Ohio, US; 2002, XP-002399476, Database accession No. 2002:735039.

Database CAPLUS [Online], Chemical Abstracts Service, Columbus, Ohio, US; 2000, XP-002400287, Database accession No. 2004:529211.

Database CAOLD [Online], Chemical Abstracts Service, Columbus, Ohio, US; XP-002399796, Database accession No. ca62:10558e, 1965.

Database WPI Week 199124, Derwent Publications Ltd., London, GB; AN 1991-175738, XP-002399811.

French Search Report for FR 0512158, dated Sep. 25, 2006.

* cited by examiner

USE OF AT LEAST ONE CATIONIC CYANIN DERIVATIVE FOR DYEING THE HAIR, COMPOSITION CONTAINING IT, PROCESS FOR TREATING KERATIN FIBERS USING THE COMPOSITION, AND DEVICE THEREFOR

This application claims benefit of U.S. Provisional Application No. 60/771,432 filed Feb. 9, 2006, the contents of which are incorporated herein by reference. This application also claims benefit of priority under 35 U.S.C. § 119 to French Patent Application No. FR 05 12158, filed Nov. 30, 2005, the contents of which are also incorporated herein by reference.

The present disclosure relates to the use of at least one direct dye derived from cationic cyanin, for dyeing the hair. The disclosure also relates to a composition comprising, in a cosmetically acceptable medium, at least one direct dye derived from cationic cyanin. The disclosure similarly relates to a process for treating keratin fibers using this composition, and also to a device comprising it. Additionally, the present disclosure relates to the use of the composition according to the disclosure as an optical lightening agent and/or as a coloring agent for the fibers.

The present disclosure thus relates to the field of dyeing keratin fibers, such as dyeing of the hair. There are essentially two types of dyeing. The first is semi-permanent dyeing or direct dyeing, which involves dyes capable of giving the hair's natural color a more or less pronounced change. The dyes used are colored and coloring substances that have a certain affinity for keratin fibers. It should be noted that this type of dyeing fades out after several washes, which may be an inconvenience.

When it is desired to obtain a coloration that is lighter than the original color of the fibers, it is necessary to use, with the direct dyes, at least one oxidizing agent, under alkaline pH conditions. However, these conditions of use are not free of consequences on the properties of the treated fibers. In the long run, the fibers are more or less degraded and have a tendency to become coarse, dull, brittle and difficult to style.

The second is permanent dyeing or oxidation dyeing. This is performed with oxidation dye precursors, which are colorless or weakly colored compounds, comprising at least one oxidation base optionally combined with at least one coupler. Once mixed with oxidizing products, at the time of use, the precursors give rise to colored compounds and dyes via a process of oxidative condensation.

Given the necessary presence of an oxidizing agent in this type of coloration, the drawbacks mentioned above may also arise in this case.

It has recently been found that compositions comprising at least one fluorescent compound constitute an interesting alternative to standard lightening processes using an oxidizing agent. Thus, for dark hair, such as hair with a tone depth of less than or equal to 6 (dark blond), and, for example, of less than or equal to 4 (chestnut), it has been found that there are regions for which the curve of reflectance as a function of the wavelength (between 500 and 700 nm) for hair treated with the composition comprising the fluorescent compound is higher than the curve corresponding to untreated hair. Consequently, the hair appears lightened, without it being necessary to use an oxidizing agent.

The notion of "tone" is based on the classification of natural shades, one tone separating each shade from the one immediately following or preceding it. This definition and the classification of natural shades are well known to hairstyling professionals and are published in the book "Sciences des traitements capillaires" by Charles Zviak, 1988, published by Masson, pp. 215 and 278. The tone depths range from 1 (black) to 10 (light light blond), one unit corresponding to one tone; the higher the figure, the lighter the shade.

Although such compositions constitute progress in this field, it nevertheless remains that the stability on storage of these compositions may be improved.

Moreover, it is desirable to have available compositions which make it possible to obtain colorations that are sufficiently fast with respect to washing and to the action of light, which is rarely the case for the colorations obtained with direct dyes, whether they are fluorescent or non-fluorescent.

It has been found by the present inventor, entirely unexpectedly, that certain direct dyes derived from cationic cyanin make it possible to obtain colorations with satisfactory properties in terms of stability and selectivity (variation of coloration between the various parts of a hair or of a head of hair) and fastness. These direct dyes may also be more stable in alkaline oxidizing medium.

The present disclosure thus relates to the use as an agent for dyeing keratin fibers, such as human keratin fibers, and/or as an agent for the optical lightening of these fibers, of at least one compound corresponding to formula (I) below

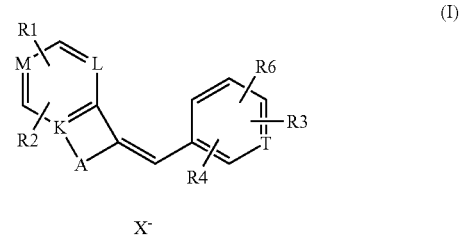

wherein:
  M and L, independently of each other, are chosen from $CR_7$, $CR_9$ and $N^+R_5$;
  K is chosen from a carbon atom and a quaternized nitrogen atom $N^+$;
  T is chosen from $N^+R_5$, $CR_4$, and nitrogen atom;
  A is chosen from linear and branched alkylene groups $C_nH_{2n}$ containing from 1 to 8 carbon atoms and optionally having at one end an oxygen atom or a carbonyl group; and from groups comprising at least one unsaturation, the unsaturation forming part of a benzene nucleus or of a heterocycle optionally substituted with at least one radical chosen from $C_1$-$C_4$ alkyl and $C_6$-$C_{30}$ aryl radicals;
  $R_1$, $R_2$, $R_3$, $R_4$, $R_6$, $R_7$ and $R_9$, independently of each other, are chosen from hydrogen atoms; halogen atoms; $C_6$-$C_{30}$ aryl groups; hydroxyl groups; cyano groups; nitro groups; sulfo groups; amino groups; acylamino groups; di($C_1$-$C_6$)alkylamino groups; dihydroxy($C_1$-$C_6$)alkylamino groups; ($C_1$-$C_6$)alkylhydroxy($C_1$-$C_6$) alkylamino groups; ($C_1$-$C_6$)alkoxy groups; ($C_1$-$C_6$) alkoxycarbonyl groups; carboxy($C_1$-$C_6$)alkoxy groups; piperidinosulfonyl groups; pyrrolidino groups; ($C_1$-$C_6$) alkylhalo($C_1$-$C_6$)alkylamino groups; benzoyl($C_1$-$C_6$) alkyl groups; vinyl groups; formyl groups; $C_6$-$C_{30}$ aryl radicals optionally substituted with at least one group chosen from hydroxyl, linear, branched and cyclic $C_1$-$C_6$ alkoxy groups and linear, branched and cyclic alkyl groups containing from 1 to 22 carbon atoms, which are optionally substituted with at least one group chosen from hydroxyl, amino and $C_1$-$C_6$ alkoxy groups; and linear, branched and cyclic alkyl radicals containing from 1 to 22 carbon atoms, such as, for example, from 1 to 6 carbon atoms, optionally substituted with at least one group chosen from hydroxyl, amino, linear, branched and cyclic $C_1$-$C_6$ alkoxy groups, optionally substituted aryl, carboxyl and sulfo groups and a halogen atom, wherein the alkyl radical is optionally interrupted with a heteroatom, such as N, S or O;

wherein two of the substituents $R_1$, $R_2$, $R_7$ and $R_9$, when M and L are chosen from, respectively, $CR_7$ and $CR_9$, may form with the carbon atoms to which they are attached an aromatic or non-aromatic $C_6$-$C_{30}$ ring or a 5- to 30-membered heterocyclic ring containing from 1 to 5 heteroatoms; these rings being optionally condensed, with the optional insertion of a carbonyl group, and being optionally substituted with at least one group chosen from $C_1$-$C_4$ alkyl, $(C_1$-$C_4)$alkoxy$(C_1$-$C_4)$alkyl, amino, di$(C_1$-$C_4)$alkylamino, halogen, phenyl, carboxyl and tri$(C_1$-$C_4)$alkylammonio$(C_1$-$C_4)$alkyl groups;

$R_1$, $R_2$, $R_7$, and $R_9$ may also be chosen from groups similar to the part of the molecule condensed on the pyridinium nucleus so as to form a perfectly symmetrical molecule, thus necessarily comprising an acridinium sequence;

wherein two of the substituents $R_3$, $R_4$ and $R_6$ may form with the carbon atoms to which they are attached a ring chosen from a $C_6$-$C_{30}$ aromatic nucleus and a 5- to 30-membered heterocyclic nucleus comprising in total from 1 to 5 heteroatoms; this ring being optionally condensed, optionally substituted with at least one group chosen from $C_1$-$C_4$ alkyl, $(C_1$-$C_4)$alkoxy$(C_1$-$C_4)$alkyl, amino, di$(C_1$-$C_4)$alkylamino, halogen, phenyl, carboxyl and tri$(C_1$-$C_4)$alkylammonio$(C_1$-$C_4)$alkyl groups, and also optionally forming with the third substituent and the carbon atom bearing it a new saturated or unsaturated, 5- to 10-membered ring;

$R_5$ is chosen from linear, branched and cyclic alkyl radicals containing from 1 to 22 carbon atoms, optionally substituted with at least one group chosen from hydroxyl, linear, branched and cyclic $C_1$-$C_6$ alkoxy groups, optionally substituted aryl groups, carboxyl groups, sulfo groups, and halogen atoms, this alkyl radical being optionally interrupted with a heteroatom such as N, O or S; a $C_6$-$C_{30}$ aryl radical optionally substituted with at least one radical chosen from $C_1$-$C_4$ alkyl radicals, $C_1$-$C_4$ alkoxy radicals and hydroxyl radicals;

$R_5$ may form with the nitrogen atom bearing it and with one of the substituents $R_1$, $R_2$, $R_7$ and $R_9$ and the carbon atom bearing this substituent a 5- to 10-membered ring optionally substituted with an alkyl group. This ring may be optionally condensed with a benzene ring or with a ring formed by two of the remaining substituents and the carbon atoms bearing them;

$X^-$ is chosen from organic and mineral anions;

wherein at least one from among K, L and M is $N^+R_5$ (L and/or M) or $N^+$ (K);

In the context of the present disclosure, "optical lightening" means a visual and visible lightening obtained without using an oxidizing agent.

These dyes may allow powerful, chromatic, sparingly selective and fast colorations to be obtained.

The direct dyes according to the present disclosure may also allow colorations that are lighter than the original color of the keratin fibers to be obtained when applied to dark fibers, without the presence of an oxidizing agent being necessary. However, it is also possible for the dyes to be used in the presence of such an agent.

The present disclosure also relates to a composition comprising, in a cosmetically acceptable medium, at least one cationic direct dye corresponding to formula (I) defined above.

The disclosure also relates to a process for treating keratin fibers, such as human keratin fibers, wherein the composition according to the present disclosure is applied to wet or dry fibers, for a time that is sufficient to develop the coloration, after which the resulting fibers are rinsed, optionally washed with shampoo, rinsed again and dried or left to dry.

According to at least one embodiment of the process, the composition according to the present disclosure is applied to the wet or dry fibers without final rinsing.

The present disclosure also relates to the use of the composition as a dyeing agent or as an optical lightener of keratin fibers.

The present disclosure also relates to a device comprising the composition according to the present disclosure.

However, other characteristics and advantages of the present disclosure will emerge even more clearly on reading the description and the examples that follow.

In at least one embodiment, the compound of formula (I) is chosen from the compounds of formulae (II) to (V) below:

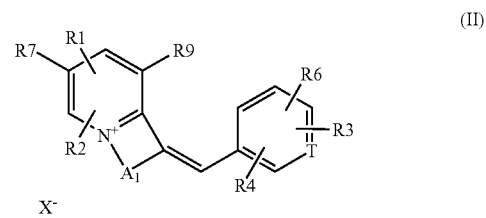

(II)

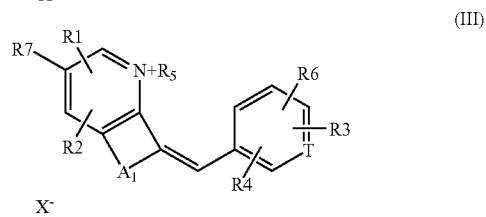

(III)

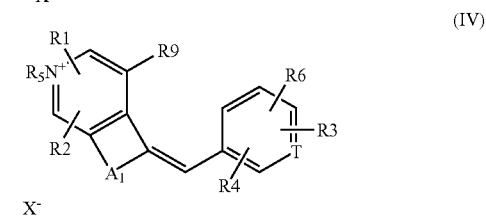

(IV)

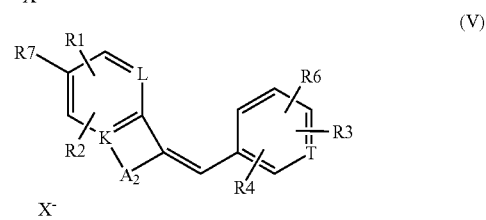

(V)

wherein:

$R_1$, $R_2$, $R_3$, $R_4$, $R_5$, $R_6$, $R_7$, $R_9$, K, L, X and T are as defined above with respect to formula (I) and wherein:

$A_1$ is chosen from linear and branched alkylene groups $C_nH_{2n}$ containing from 1 to 8 carbon atoms and optionally having at one end an oxygen atom or a carbonyl group;

$A_2$ is chosen from groups comprising at least one unsaturation, the unsaturation forming part of a benzene nucleus or of a heterocycle optionally substituted with at least one radical chosen from $C_1$-$C_4$ alkyl and $C_6$-$C_{30}$ aryl radicals;

wherein only one of the groups K and L denotes $N^+$ or $N^+R_5$, respectively.

In the text hereinbelow and unless otherwise indicated, the limits of a range of values are understood as forming part of this range.

According to the present disclosure, the term "human keratin fibers" means the hair, the eyelashes and the eyebrows.

According to at least one embodiment of the present disclosure, the direct dye is intended to be applied to dark keratin fibers. In at least one embodiment, the dark keratin fibers are pigmented fibers or artificially colored fibers, the tone depth of which is less than or equal to 6, such as, for example less than or equal to 4.

The mesomeric forms of the compounds of formulae (I) to (V) are also included in the context of the present disclosure.

In at least one embodiment, in formula (I):

$R_1$, $R_2$, $R_3$, $R_4$, $R_6$, $R_7$ and $R_9$, independently of each other, are chosen from hydrogen atoms; $C_6$-$C_{30}$ aryl groups optionally substituted with a group chosen from $C_1$-$C_6$ alkyl radicals, $C_1$-$C_6$ alkoxy radicals and hydroxyl radicals; hydroxyl groups; nitro groups; vinyl groups; pyrrolidino groups; benzoyl($C_1$-$C_6$)alkyl groups; ($C_1$-$C_6$)alkylhalo($C_1$-$C_6$)alkylamino groups; amino groups; di($C_1$-$C_6$)alkylamino groups; dihydroxy($C_1$-$C_6$)alkylamino groups; ($C_1$-$C_6$)alkylhydroxy($C_1$-$C_6$)alkylamino groups; $C_1$-$C_6$ alkoxy groups; formyl groups; linear, branched and cyclic alkyl radicals containing from 1 to 6 carbon atoms, optionally substituted with at least one group chosen from hydroxyl and optionally substituted aryl groups, $R_1$, $R_2$, $R_7$, and $R_9$ may form with the carbon atoms to which they are attached a ring chosen from aromatic or non-aromatic $C_6$-$C_{30}$ rings and 5- to 30-membered heterocyclic rings comprising in total from 1 to 5 heteroatoms; these rings being optionally condensed, with optional insertion of a carbonyl group, and being optionally substituted with at least one group chosen from $C_1$-$C_4$ alkyl, ($C_1$-$C_4$)alkoxy($C_1$-$C_4$)alkyl, amino, di($C_1$-$C_4$)alkylamino and phenyl groups;

$R_1$, $R_2$, $R_7$, and $R_9$ may also represent a group similar to the part of the molecule condensed on the pyridinium nucleus so as to form a perfectly symmetrical molecule, thus necessarily comprising an acridinium sequence;

$R_3$ and $R_4$ may form with the carbon atoms to which they are attached a ring chosen from a $C_6$-$C_{30}$ aromatic nucleus and a 5- to 30-membered heterocyclic nucleus comprising in total from 1 to 5 heteroatoms; this ring being optionally condensed and optionally substituted with at least one $C_1$-$C_4$ alkyl group. This ring may also form with $R_6$ and the carbon atom bearing it a new saturated or unsaturated 5- to 10-membered ring;

$R_5$ is chosen from linear, branched and cyclic alkyl radicals containing from 1 to 22 carbon atoms or $C_6$-$C_{30}$ aryl radicals optionally substituted with at least one radical chosen from $C_1$-$C_4$ alkyl, $C_1$-$C_4$ alkoxy and hydroxyl radicals;

$R_5$ may form with the nitrogen atom bearing it and with $R_1$ and the carbon atom bearing this substituent $R_1$ a 5- to 10-membered ring optionally substituted with an alkyl group. This ring may be optionally condensed with a benzene ring or with a ring formed by $R_1$ and $R_2$ and the carbon atoms bearing them.

In at least one embodiment, in formula (II):

$A_1$ is chosen from linear and branched alkylene groups $C_nH_{2n}$ containing from 1 to 8 carbon atoms and optionally having at one of its ends a carbonyl group;

$R_1$, $R_2$, $R_3$, $R_4$, $R_6$, $R_7$ and $R_9$, independently of each other, are chosen from hydrogen atoms; $C_6$-$C_{30}$ aryl groups optionally substituted with a group chosen from $C_1$-$C_6$ alkyl, $C_1$-$C_6$ alkoxy and hydroxyl radicals; hydroxyl groups; vinyl groups; pyrrolidino groups; benzoyl($C_1$-$C_6$)alkyl groups; ($C_1$-$C_6$)alkylhalo($C_1$-$C_6$)alkylamino groups; amino groups; di($C_1$-$C_6$)alkylamino groups; dihydroxy($C_1$-$C_6$)alkylamino groups; ($C_1$-$C_6$)alkylhydroxy($C_1$-$C_6$)alkylamino groups; $C_1$-$C_6$ alkoxy groups; formyl groups; linear, branched and cyclic alkyl radicals containing from 1 to 6 carbon atoms, optionally substituted with at least one group chosen from hydroxyl and optionally substituted aryl groups, $R_3$ and $R_4$ may form with the carbon atoms to which they are attached a ring chosen from a $C_6$-$C_{30}$ aromatic nucleus and a 5- to 30-membered heterocyclic nucleus comprising in total from 1 to 5 heteroatoms; these rings being optionally condensed and optionally substituted with at least one $C_1$-$C_4$ alkyl group. This ring may also form with $R_6$ and the carbon atom bearing it a new saturated or unsaturated 5- to 10-membered ring.

In at least one embodiment, in formula (II):

$A_1$ is chosen from alkylene groups containing from 2 to 4 carbon atoms;

T is chosen from $CR_4$, $N^+R_5$ or N;

$R_1$, $R_2$, $R_7$ and $R_9$ are hydrogen atoms;

$R_3$ and $R_4$, independently of each other, are chosen from hydrogen atoms; $C_1$-$C_4$ alkyl radicals (for example, methyl); $C_1$-$C_4$ alkoxy radicals (for example, methoxy); di($C_1$-$C_4$) alkylamino groups (for example, dimethylamino or diethylamino); dihydroxy($C_1$-$C_4$)alkylamino groups (for example, dihydroxyethylamino); ($C_1$-$C_4$)alkylhydroxy($C_1$-$C_4$)alkylamino groups (for example, methylhydroxyethylamino); pyrrolidino groups; and formyl groups; or form, together with the carbon atoms bearing them, a 5- or 6-membered ring optionally comprising at least one heteroatom, this ring being optionally condensed, and the whole being optionally substituted with at least one $C_1$-$C_6$ alkyl radical;

$R_6$ is a hydrogen atom or forms a ring including a ring member of a ring formed by $R_3$ and/or $R_4$.

In at least one embodiment, in formula (III):

$A_1$ is chosen from linear and branched alkylene groups $C_nH_{2n}$ containing from 1 to 8 carbon atoms and optionally having at one end a carbonyl group;

$R_1$, $R_2$, $R_3$, $R_4$, $R_6$, and $R_7$, independently of each other, are chosen from hydrogen atoms; $C_6$-$C_{30}$ aryl groups optionally substituted with a group chosen from $C_1$-$C_6$ alkyl, $C_1$-$C_6$ alkoxy and hydroxyl radicals; hydroxyl groups; vinyl groups; pyrrolidino groups; benzoyl($C_1$-$C_6$)alkyl groups; ($C_1$-$C_6$) alkylhalo($C_1$-$C_6$)alkylamino groups; amino groups; di($C_1$-$C_6$)alkylamino groups; dihydroxy($C_1$-$C_6$)alkylamino groups; ($C_1$-$C_6$)alkylhydroxy($C_1$-$C_6$)alkylamino groups; $C_1$-$C_6$ alkoxy groups; linear, branched and cyclic alkyl radicals containing from 1 to 6 carbon atoms, optionally substituted with at least one group chosen from hydroxyl and optionally substituted aryl groups;

$R_3$ and $R_4$ may form with the carbon atoms to which they are attached a ring chosen from a $C_6$-$C_{30}$ aromatic nucleus and a 5- to 30-membered heterocyclic nucleus comprising in total from 1 to 5 heteroatoms; these rings being optionally condensed and optionally substituted with at least one $C_1$-$C_4$ alkyl group. This ring may also form with $R_6$ and the carbon atom bearing it a new saturated or unsaturated 5- to 10-membered ring;

$R_1$ and $R_7$ may also be chosen from groups similar to the part of the molecule condensed on the pyridinium nucleus so as to form a perfectly symmetrical molecule, thus necessarily comprising an acridinium sequence;

$R_5$ is chosen from linear, branched and cyclic alkyl radicals containing from 1 to 10 carbon atoms and $C_6$-$C_{30}$ aryl radicals optionally substituted with at least one radical chosen from $C_1$-$C_4$ alkyl, $C_1$-$C_4$ alkoxy or hydroxyl radicals;

$R_5$ may form with the nitrogen atom bearing it and with $R_1$ and the carbon atom bearing this substituent $R_1$ a 5- to 10-membered ring optionally substituted with an alkyl group. This ring may be optionally condensed with a benzene ring or with a ring formed by $R_1$ and $R_2$ and the carbon atoms bearing them.

In at least one embodiment, in formula (III):

$A_1$ is chosen from alkylene groups containing from 2 to 5 carbon atoms, and optionally having at one end a carbonyl group, and optionally substituted with at least one $C_1$-$C_6$ alkyl group;

T is $CR_4$;

$R_1$, $R_2$ and $R_7$, independently of each other, are chosen from hydrogen atoms and phenyl radicals, or form, together with the carbon atoms bearing them, a $C_6$-$C_{12}$ aromatic ring or a saturated ring with the optional insertion of a carbonyl group into its ring members, these rings being optionally substituted with $C_1$-$C_4$ alkyl groups (for example, methyl);

$R_5$ is chosen from $C_1$-$C_4$ alkyl radicals (for example, methyl or ethyl); $C_6$-$C_{12}$ aryl radicals optionally substituted with at least one radical chosen from $C_1$-$C_4$ alkyl, hydroxyl and $C_1$-$C_4$ alkoxy radicals (for example, methoxy); or forms a ring including a ring member of a ring derived from $R_1$, $R_2$ and/or $R_7$ and from the atoms bearing them;

$R_3$ and $R_6$ are hydrogen atoms;

$R_4$ is chosen from hydrogen atoms, di($C_1$-$C_4$)alkylamino groups (for example, dimethylamino), and ($C_1$-$C_4$)alkylhalo($C_1$-$C_4$)alkylamino groups (for example, ethylchloroethylamino).

In at least one embodiment, in formula (IV):

$A_1$ is chosen from linear and branched alkylene groups $C_nH_{2n}$ containing from 1 to 8 carbon atoms and optionally having at one end a carbonyl group;

$R_1$, $R_2$, $R_3$, $R_4$, $R_6$, and $R_9$, independently of each other, are chosen from hydrogen atoms; $C_6$-$C_{30}$ aryl groups optionally substituted with a group chosen from $C_1$-$C_6$ alkyl, $C_1$-$C_6$ alkoxy and hydroxyl radicals; hydroxyl groups; vinyl groups; pyrrolidino groups; benzoyl($C_1$-$C_6$)alkyl groups; ($C_1$-$C_6$)alkylhalo($C_1$-$C_6$)alkylamino groups; amino groups; di($C_1$-$C_6$)alkylamino groups; dihydroxy($C_1$-$C_6$)alkylamino groups; ($C_1$-$C_6$)alkylhydroxy($C_1$-$C_6$)alkylamino groups; $C_1$-$C_6$ alkoxy groups; linear, branched and cyclic alkyl radicals containing from 1 to 6 carbon atoms, optionally substituted with at least one group chosen from hydroxyl and optionally substituted aryl groups;

$R_3$ and $R_4$ may form with the carbon atoms to which they are attached a ring chosen from a $C_6$-$C_{30}$ aromatic nucleus and a 5- to 30-membered heterocyclic nucleus comprising in total from 1 to 5 heteroatoms; these rings being optionally condensed and optionally substituted with at least one $C_1$-$C_4$ alkyl group. This ring may also form with $R_6$ and the carbon atom bearing it a new saturated or unsaturated 5- to 10-membered ring;

$R_5$ is chosen from linear, branched and cyclic alkyl radicals containing from 1 to 22 carbon atoms and $C_6$-$C_{30}$ aryl radicals optionally substituted with at least one $C_1$-$C_4$ alkyl, $C_1$-$C_4$ alkoxy or hydroxyl radical;

$R_5$ may form with the nitrogen atom bearing it and with $R_1$ and the carbon atom bearing this substituent $R_1$ a 5- to 10-membered ring optionally substituted with an alkyl group. This ring may be optionally condensed with a benzene ring or with a ring formed by $R_1$ and $R_2$ and the carbon atoms bearing them.

In at least one embodiment, in formula (IV):

$A_1$ is chosen from linear and branched alkylene groups $C_nH_{2n}$ containing from 1 to 4 carbon atoms;

T is $CR_4$;

$R_2$, $R_3$ and $R_6$ are hydrogen atoms;

$R_1$ and $R_9$, independently of each other, are chosen from hydrogen atoms $C_6$-$C_{12}$ aryl radical or form, together with the carbon atoms bearing them, an optionally condensed $C_6$-$C_{12}$ aromatic ring, all these rings optionally being substituted;

$R_4$ is chosen from hydrogen atoms, di($C_1$-$C_6$)alkylamino groups (for example, dimethylamino, diethylamino or dihexylamino), dihydroxy($C_1$-$C_6$)alkylamino groups and ($C_1$-$C_6$)alkylhydroxy($C_1$-$C_6$)alkylamino groups;

$R_5$ is chosen from $C_1$-$C_{22}$ alkyl, phenyl and benzyl groups, or forms with $R_1$ and $R_2$ and/or $R_9$ and the atoms bearing them two fused rings.

In at least one embodiment, in formula (V):

$A_2$ is chosen from groups comprising at least one unsaturation, the unsaturation forming part of a benzene nucleus or of a heterocycle optionally substituted with at least one radical chosen from $C_1$-$C_4$ alkyl and $C_6$-$C_{30}$ aryl radicals;

$R_1$, $R_2$, $R_3$, $R_4$, $R_6$, and $R_7$, independently of each other, are chosen from hydrogen atoms; $C_6$-$C_{30}$ aryl groups optionally substituted with a group chosen from $C_1$-$C_6$ alkyl, $C_1$-$C_6$ alkoxy and hydroxyl radicals; hydroxyl groups; vinyl groups; pyrrolidino groups; benzoyl($C_1$-$C_6$)alkyl groups; ($C_1$-$C_6$)alkylhalo($C_1$-$C_6$)alkylamino groups; amino groups; di($C_1$-$C_6$)alkylamino groups; dihydroxy($C_1$-$C_6$)alkylamino groups; ($C_1$-$C_6$)alkylhydroxy($C_1$-$C_6$)alkylamino groups; $C_1$-$C_6$ alkoxy groups; formyl groups; linear, branched and cyclic alkyl radicals containing from 1 to 6 carbon atoms, optionally substituted with at least one group chosen from hydroxyl and optionally substituted aryl groups, $R_3$ and $R_4$ may form with the carbon atoms to which they are attached a ring chosen from a $C_6$-$C_{30}$ aromatic nucleus and a 5- to 30-membered heterocyclic nucleus comprising in total from 1 to 5 heteroatoms; these rings being optionally condensed and optionally substituted with at least one $C_1$-$C_4$ alkyl group. This ring may also form with $R_6$ and the carbon atom bearing it a new saturated or unsaturated 5- to 10-membered ring.

In at least one embodiment, in formula (V), $R_1$, $R_2$, and $R_7$, independently of each other, are chosen from hydrogen atoms and $C_1$-$C_4$ alkyl or vinyl radicals, or form, together with the carbon atoms bearing them, a saturated or unsaturated ring optionally bearing at least one alkyl radical;

$R_6$ is a hydrogen atom;

$R_3$ and $R_4$, independently of each other, are chosen from hydrogen atoms; $C_1$-$C_4$ alkyl groups (for example methyl); dialkylamino groups (for example dimethylamino); $C_1$-$C_4$ alkoxy groups (for example methoxy or ethoxy); hydroxyl radicals; nitro groups; $C_1$-$C_4$ benzoylalkyl radicals; or together form a 5- or 6-membered ring with the carbon atoms bearing them.

If L is $N^+R_5$, $R_5$ is chosen from $C_1$-$C_4$ alkyl radicals and benzoyl($C_1$-$C_4$)alkyl radicals.

If K is $N^+$, $R_9$ is a hydrogen atom.

In at least one example, $A_2$ is chosen from a sequence —C($R_{10}$)=C($R_{11}$)—, a sequence —N=CH—NH— and a pyrazolyl radical;

$R_{10}$ and $R_{11}$, independently of each other, are chosen from $C_1$-$C_4$ alkyl radicals (for example methyl) and phenyl radicals, or together form a benzene nucleus.

The direct dye according to at least one embodiment of the present disclosure is a fluorescent molecule, i.e., a molecule that colors by itself, absorbs light from the visible spectrum and also optionally from the ultraviolet spectrum (wavelengths ranging from 360 to 760 nanometers), but which, contrary to a standard dye, converts part of the absorbed energy into fluorescent light of a wavelength longer than that absorbed, emitted in the visible part of the spectrum.

In addition, the fluorescent dye according to at least one embodiment of the present disclosure is a dye that generates fluorescence on the support onto which it is applied.

According to at least one embodiment of the present disclosure, the direct dye has a solubility in the medium of a composition or at least 1 gram per liter, such as, for example, at least 5 grams per liter at a temperature of 25° C.

It should be noted that $X^-$ may be an anion of mineral origin chosen, for example, from halides, sulfates, bisulfates, nitrates, phosphates, hydrogen phosphates, dihydrogen phosphates, boronates, carbonates and bicarbonates.

The anion $X^-$ may also be of organic origin, and in this case chosen, for example, from those derived from salts of saturated or unsaturated, aromatic or non-aromatic monocarboxylic or polycarboxylic, sulfonic or sulfuric acids, optionally substituted with at least one hydroxyl or amino radical or halogen atoms.

In at least one embodiment, $X^-$ is chosen from chloride, iodide, sulfate, metho-sulfate and ethosulfate.

In accordance with at least one embodiment of the present disclosure, the compound of formula (II) is chosen from one of the following compounds:

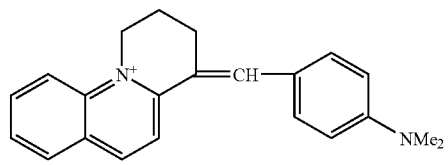

4-[[4-(Dimethylamino)phenyl]methylene]-
1,2,3,4-tetrahydrobenzo[c]quinolizinium
perchlorate

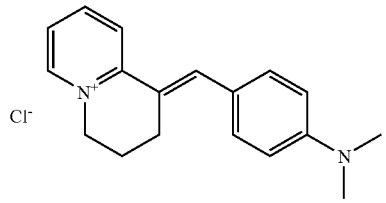

1-(4-Dimethylaminobenzyl-idene)-1,2,3,4-
tetrahydro-quinolizinylium chloride

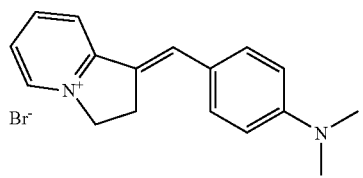

1-(4-Dimethylaminobenzylidene)-2,3-
dihydro-1H-indolizinylium bromide

-continued

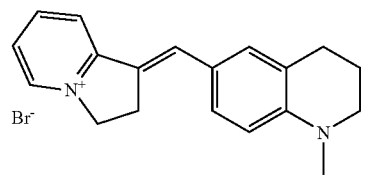

1-(1-Methyl-1,2,3,4-tetrahydro-quinolin-6-
ylmethylene)-2,3-dihydro-1H-
indolizinylium bromide

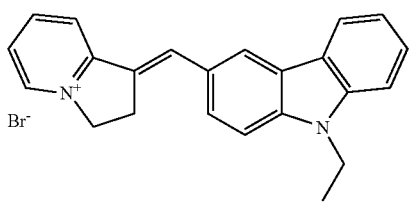

1-(9-Ethyl-9H-carbazol-3-ylmethylene)-
2,3-dihydro-1H-indolizinylium bromide

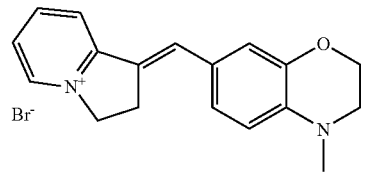

1-(4-Methyl-3,4-dihydro-2H-benzo[1,4]-
oxazin-7-yl-methylene)-2,3-dihydro-1H-
indolizinylium bromide

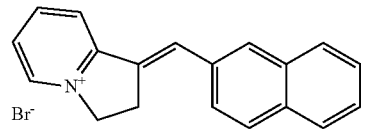

1-Naphthalen-2-ylmethylene-2,3-dihydro-
1H-indolizinylium bromide

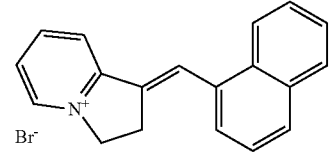

1-Naphthalen-1-ylmethylene-2,3-dihydro-
1H-indolizinylium bromide

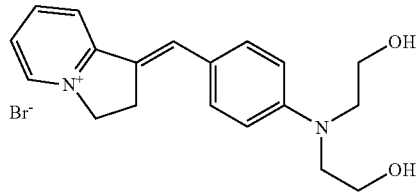

1-{4-[Bis(2-hydroxyethyl)amino]-
benzylidene}-2,3-dihydro-1H-
indolizinylium bromide -continued

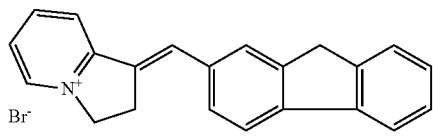

1-(9H-Fluoren-2-ylmethylene)-2,3-dihydro-
1H-indolizinylium bromide

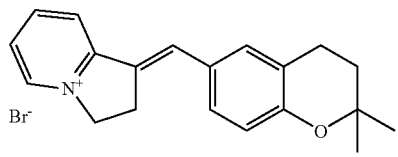

1-(2,2-Dimethylchroman-6-ylmethylene)-
2,3-dihydro-1H-indolizinylium bromide

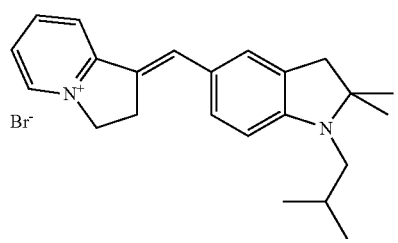

1-(1-Isobutyl-2,2-dimethyl-2,3-dihydro-1H-
indol-5-ylmethylene)-2,3-dihydro-1H-
indolizinylium bromide

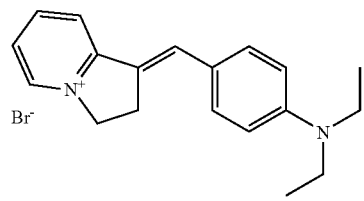

1-(4-Diethylaminobenzylidene)-2,3-
dihydro-1H-indolizinylium bromide

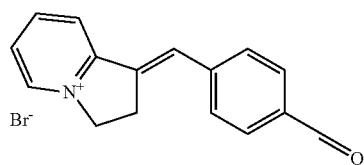

1-(4-Formylbenzylidene)-2,3-dihydro-1H-
indolizinylium bromide

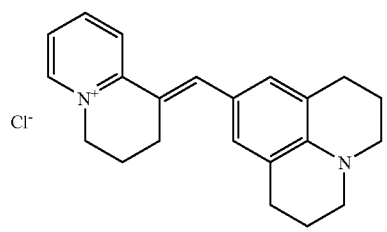

1-(2,3,6,7-Tetrahydro-1H,5H-pyrido[3,2,1-
ij]quinolin-9-ylmethylene)-1,2,3,4-
tetrahydro-quinolizinylium chloride -continued

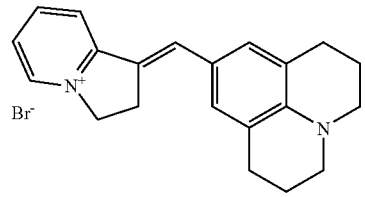

1-(2,3,6,7-Tetrahydro-1H,5H-
pyrido[3,2,1-ij]quinolin-9-ylmethylene)-2,
3-dihydro-1H-indolizinylium bromide

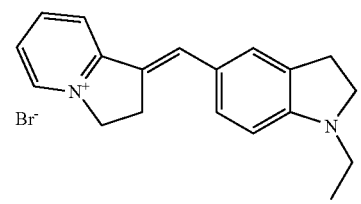

1-(1-Ethyl-2,3-dihydro-1H-indol-5-
ylmethylene)-2,3-dihydro-1H-
indolizinylium bromide

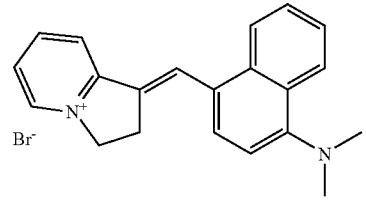

1-(4-Dimethylaminonaphthalen-1-
ylmethylene)-2,3-dihydro-1H-
indolizinylium bromide

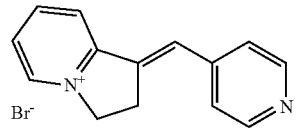

1-Pyridin-4-ylmethylene-2,3-dihydro-1H-
indolizinylium bromide

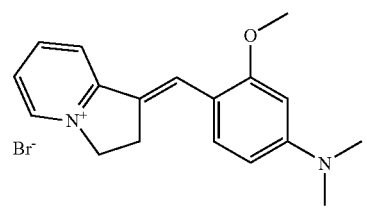

1-(4-Dimethylamino-2-methoxy-
benzylidene)-2,3-dihydro-1H-
indolizinylium bromide

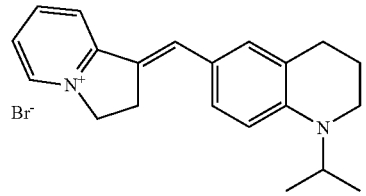

1-(1-Isopropyl-1,2,3,4-tetrahydroquinolin-
6-ylmethylene)-2,3-dihydro-1H-
indolizinylium bromide

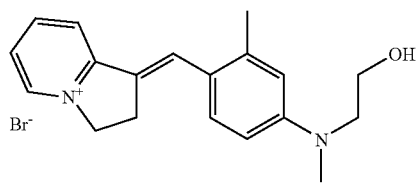

1-{4-[Ethyl(2-hydroxyethyl)amino]-2-
methylbenzylidene}-2,3-dihydro-1H-
indolizinylium bromide

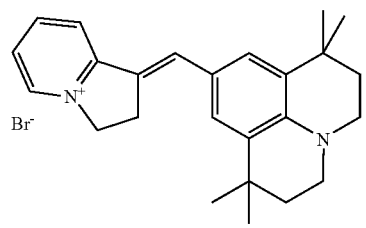

1-(1,1,7,7-Tetramethyl-2,3,6,7-
tetrahydro-1H,5H-pyrido[3,2,1-ij]quinolin-
9-ylmethylene)-2,3-dihydro-1H-
indolizinylium bromide

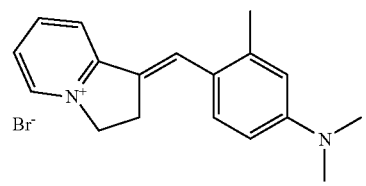

1-(4-Dimethylamino-2-
methylbenzylidene)-2,3-dihydro-1H-
indolizinylium bromide

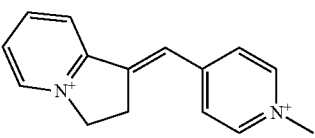

1-Methylpyridinium-4-ylmethylene-2,3-
dihydro-1H-indolizinylium dibromide

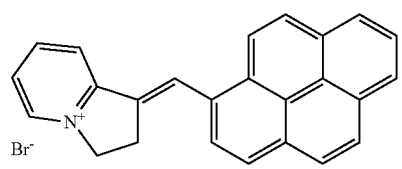

1-Pyren-1-ylmethylene-2,3-dihydro-1H-
indolizinylium bromide

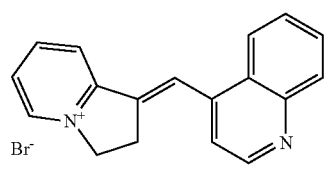

1-Quinolin-4-ylmethylene-2,3-dihydro-
1H-indolizinylium bromide

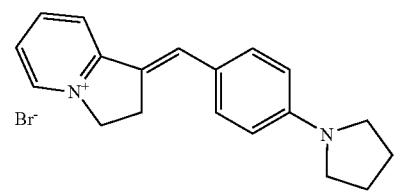

1-(4-Pyrrolidin-1-ylbenzylidene)-2,3-
dihydro-1H-indolizinylium bromide

According to at least one embodiment of the disclosure, the compound of formula (III) is chosen from one of the following compounds:

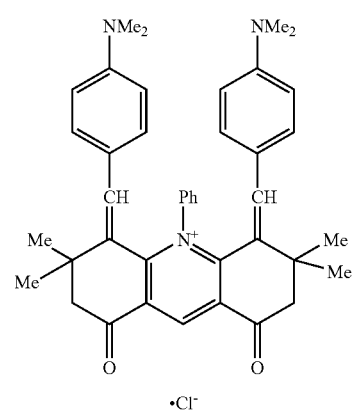

4,5-Bis[[4-(dimethylamino)phenyl]methylene]-
1,2,3,4,5,6,7,8-ootahydro-3,3,6,6-tetramethyl-1,8-
dioxo-10-phenylacridinium chloride

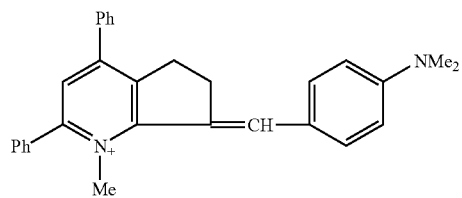

X⁻

7-[[4-(Dimethylamino)-phenyl]-
methylene]-6,7-dihydro-1-methyl-2,4-
diphenyl-5H-cyclopenta[b]-pyridinium
salt

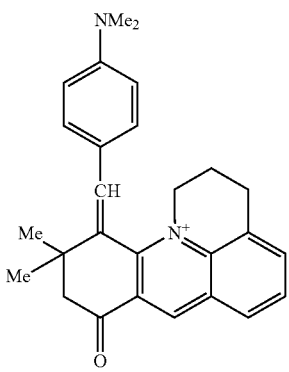

ClO₄⁻

11-[[4-(Dimethylamino)phenyl]-
methylene]-2,3,8,9,10,11-hexahydro-
10,10-dimethyl-8-oxo-1H-pyrido[3,2,1-
de]acridinium perohlorate

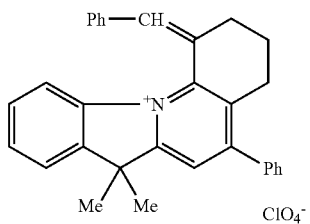

ClO₄⁻

2,3,4,7-Tetrahydro-7,7-dimethyl-5-
phenyl-1-(phenylmethylene)-1H-
indolo[1,2-a]quinolinium perchlorate

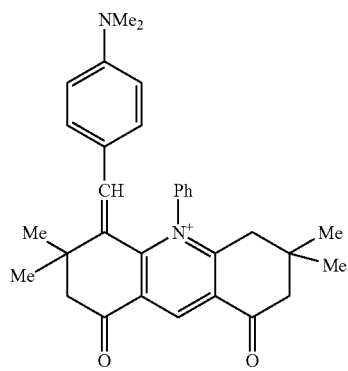

•Cl⁻

4-[[4-(Dimethylamino)phenyl]-
methylene]-1,2,3,4,5,6,7,8-octahydro-
3,3,6,6-tetramethyl-1,8-dioxo-10-
phenylacridinium chloride

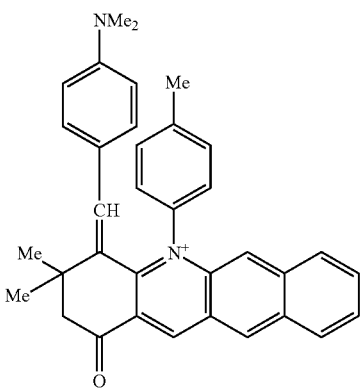

•Br⁻

4-[[4-(Dimethylamino)phenyl]-
methylene]-1,2,3,4-tetrahydro-3,3-
dimethyl-5-(4-methyl-phenyl)-1-
oxobenz[b]acridinium bromide

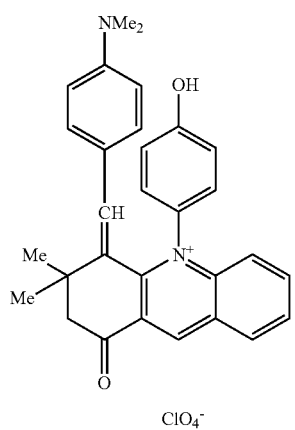

ClO₄⁻

4-[[4-(Dimethylamino)phenyl]-
methylene]-1,2,3,4-tetrahydro-10-(4-
hydroxyphenyl)-3,3-dimethyl-1-
oxoacridinium perchlorate

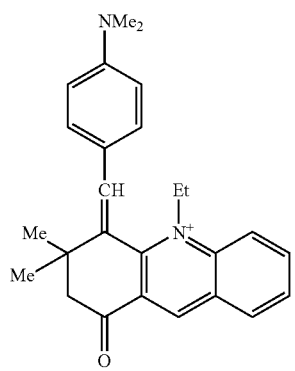

ClO₄⁻

4-[[4-(Dimethylamino)phenyl]-
methylene]-10-ethyl-1,2,3,4-
tetrahydro-3,3-dimethyl-1-
oxoacridinium perchlorate -continued

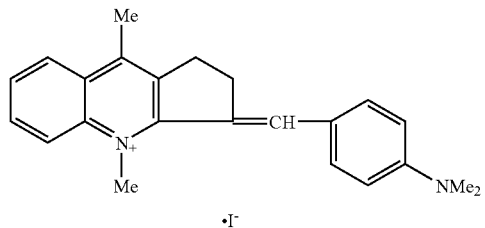

·I⁻

3-[p-(Dimethylamino)-benzylidene]-
2,3-dihydro-4,9-dimethyl-1H-
cyclopenta[b]-quinolinium iodide

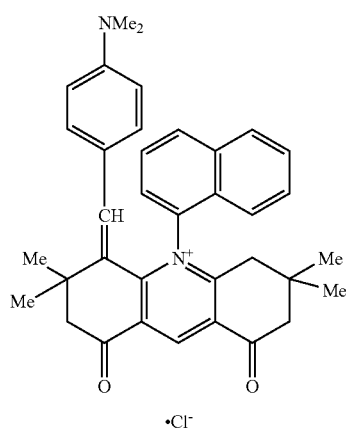

·Cl⁻

4-[[4-(Dimethylamino)phenyl]-
methylene]-1,2,3,4,5,6,7,8-octahydro-
3,3,6,6-tetramethyl-10-(1-naph-
thalenyl)-1,8-dioxoacridinium chloride

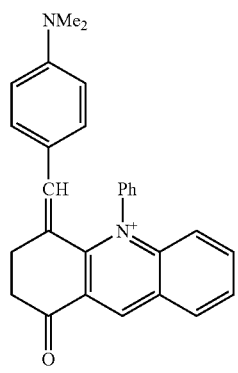

ClO₄⁻

4-[[4-(Dimethylamino)phenyl]-
methylene]-1,2,3,4-tetrahydro-1-oxo-
10-phenylacridinium perchlorate

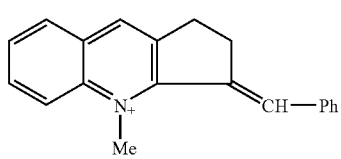

1/2 SO₄²⁻

3-Benzylidene-2,3-dihydro-4-methyl-1H-
cyclopenta[b]-quinolinium methyl sulfate

-continued

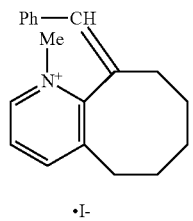

·I⁻

5,6,7,8,9,10-Hexahydro-1-methyl-10-
(phenylmethylene)p-
cycloocta[b]pyridinium iodide

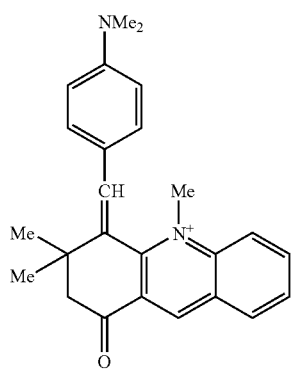

ClO₄⁻

4-[[4-(Dimethylamino)-phenyl]methylene]-
1,2,3,4-tetrahydro-3,3,10-trimethyl-1-
oxoacridinium perchlorate

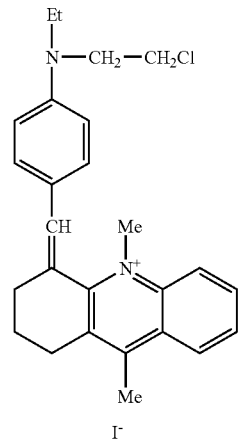

I⁻

4-[[4-[(2-Chloroethyl)ethylamino]phenyl]-
methylene]-1,2,3,4-tetrahydro-9,10-
dimethylacridinium iodide

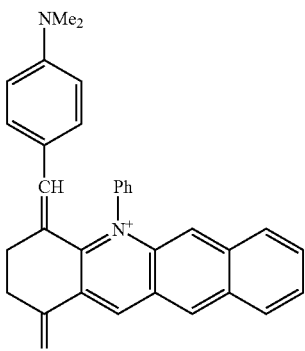

4-[[4-(Dimethylamino)-phenyl]methylene]-
1,2,3,4-tetrahydro-1-oxo-5-
phenylbenz[b]acridinium bromide

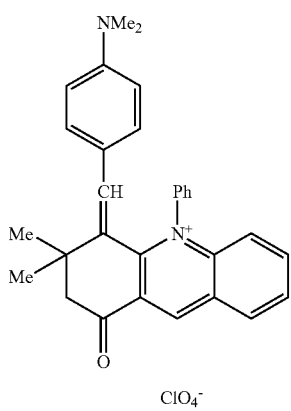

4-[[4-(Dimethylamino)phenyl]-methylene]-
1,2,3,4-tetrahydro-3,3-dimethyl-1-oxo-10-
phenylacridinium perchlorate

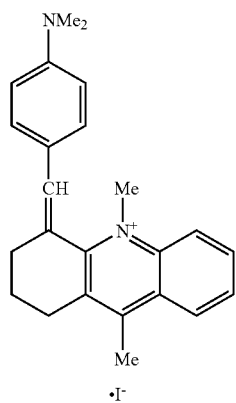

4-[p-(Dimethylamino)benzylidene]-1,2,3,4-
tetrahydro-9,10-dimethylacridinium iodide

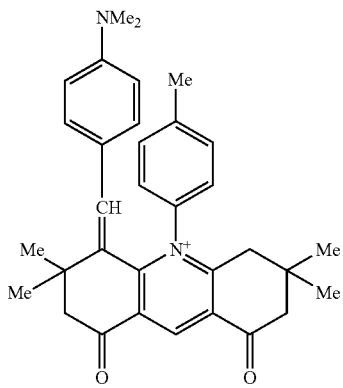

4-[[4-(Dimethylamino)-phenyl]methylene]-
1,2,3,4,5,6,7,8-octahydro-3,3,6,6-
tetramethyl-10-(4-methylphenyl)-1,8-
dioxoacridinium chloride

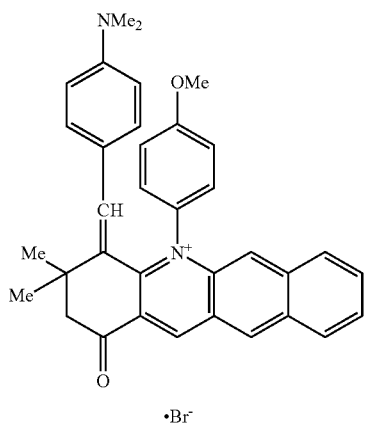

4-[[4-(Dimethylamino)-phenyl]methylene]-
1,2,3,4-tetrahydro-5-(4-methoxyphenyl)-
3,3-dimethyl-1-oxobenz[b]acridinium
bromide

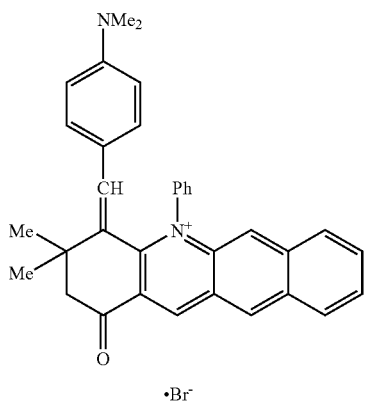

4-[[4-(Dimethylamino)-phenyl]methylene]-
1,2,3,4-tetrahydro-3,3-dimethyl-1-oxo-5-
phenylbenz[b]acridinium bromide In accordance with at least one embodiment of the disclosure, the compound of formula (IV) is chosen from one of the following compounds:

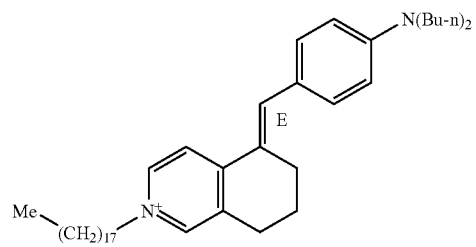

(5E)-5-[[4-(Dibutylamino)phenyl]-
methylene]-5,6,7,8-tetrahydro-2-
octadecyliso-quinolinium salt

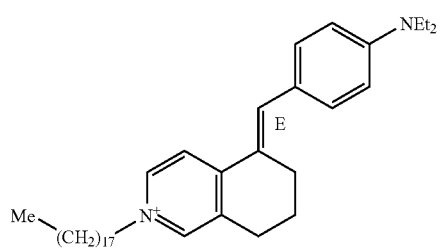

(5E)-5-[(4-(Diethylamino)phenyl]-
methylene]-5,6,7,8-tetrahydro-2-
otadecylisoquinolinium salt

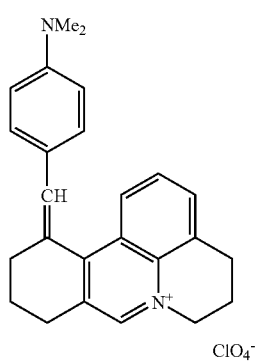

12-[[4-(Dimethylamino)-
phenyl]methylene]-5,6,9,10,11,12-
hexahydro-4H-pyrido[3,2,1-de]phen-
anthridinium perchlorate -continued

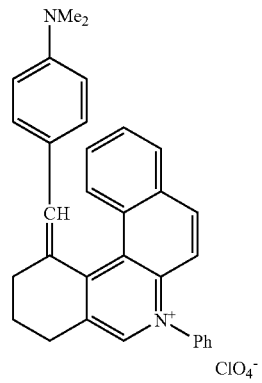

1-[[4-(Dimethylamino)phenyl]-
methylene]-1,2,3,4-tetrahydro-6-
phenylbenzo[a]-phenanthridinium
perchlorate

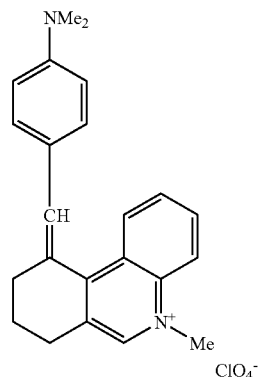

10-[[4-(Dimethylamino)phenyl]-
methylene]-7,8,9,10-tetrahydro-5-
methylphenanthridinium perchlorate

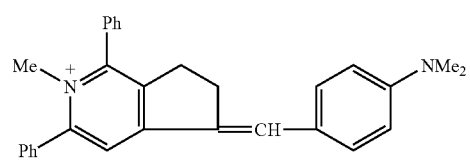

5-[[4-(Dimethylamino)phenyl]methyl-
ene]-6,7-dihydro-2-methyl-1,3-diphenyl-
5H-oyclopenta[c]pyridinium salt -continued

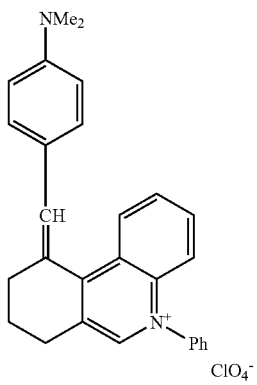

10-[[4-(Dimethylamino)phenyl]-
methylene]-7,8,9,10-tetrahydro-5-
phenylphenanthridinium perchlorate

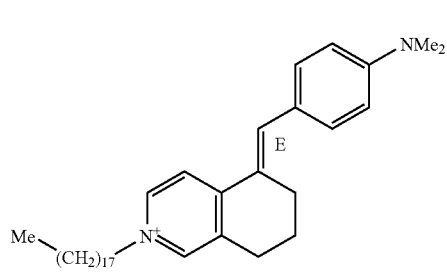

(5E)-5-[[4-(Dimethylamino)phenyl]-
methylene]-5,6,7,8-tetrahydro-2-
octadeoylisoquinolinium salt

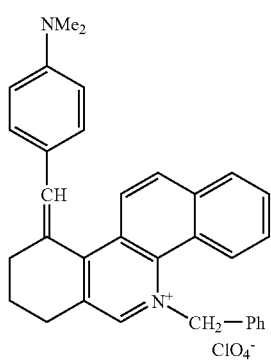

10-[[4-(Dimethylamino)phenyl]-
methylene]-7,8,9,10-tetrahydro-5-
(phenylmethyl)benzo[c]phen-
anthridinium perchlorate -continued

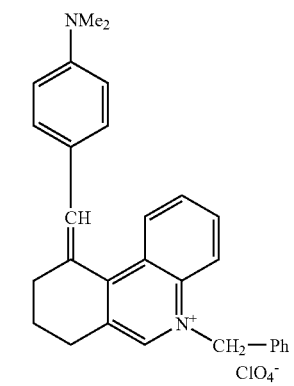

10-[[4-(Dimethylamino)-
phenyl]methylene]-7,8,9,10-tetrahydro-5-
(phenylmethyl)phenanthridinium
perchlorate

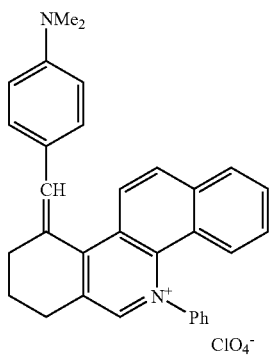

10-[[4-(Dimethylamino)phenyl]-
methylene]-7,8,9,10-tetrahydro-5-phenyl-
benzo[c]phenanthridinium perchlorate

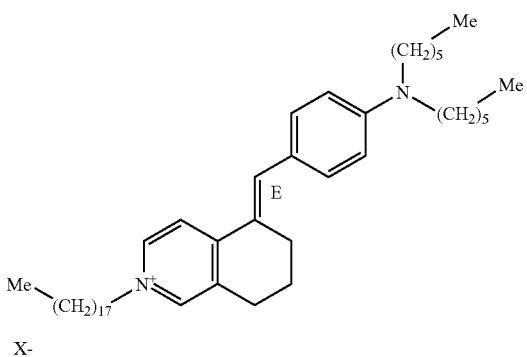

(5E)-5-[[4-(Dihexylamino)phenyl]-
methylene]-5,6,7,8-tetrahydro-2-
octadecyl isoquinolinium salt -continued

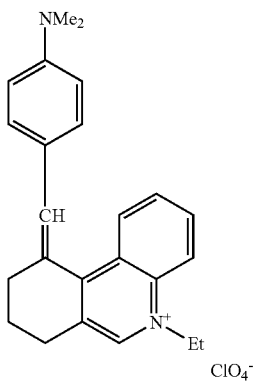

10-[[4-(Dimethylamino)phenyl]-
methylene]-5-ethyl-7,8,9,10-
tetrahydrophenanthridinium perchlorate In accordance with at least one embodiment of the present disclosure, the compound of formula (V) is chosen from one of the following compounds:

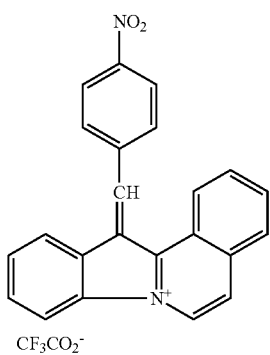

12-[(4-Nitrophenyl)methylene]-12H-
indolo[2,1-a]isoquinolinium
trifluoroacetate

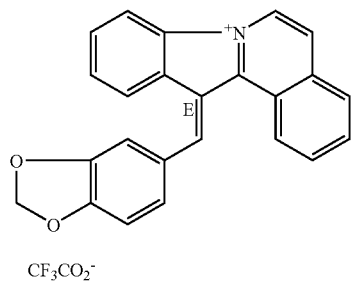

12-(1,3-Benzodioxol-5-ylmethylene-
12H-indolo[2,1-a]isoquinolinium
trifluoroacetate -continued

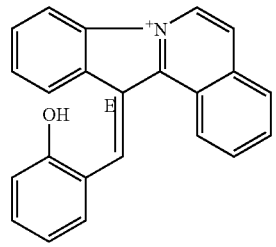

12-[(2-Hydroxyphenyl)-methylene]-
12H-indolo[2,1-a]isoquinolinium
trifluoroacetate

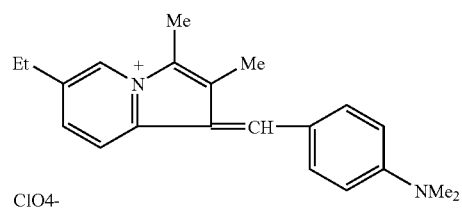

1-[[4-(Dimethylamino)phenyl]-
methylene]-6-ethyl-2,3-dimethyl-1H-
indolizinium perchlorate

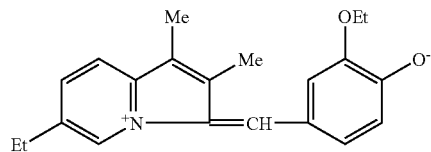

Inner salt of 3-(3-ethoxy-4-
hydroxybenzylidene)-6-ethyl-1,2-
dimethyl-3H-indolizinium hydroxide

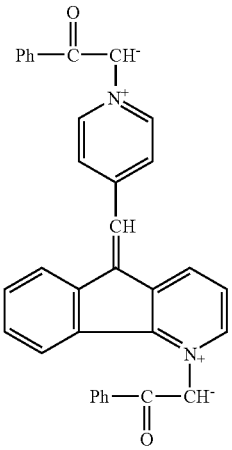

5-[[1-(2-Oxo-2-phenylethyl)pyridinium-
4-yl]methylene]-5H-indeno[1,2-b]
pyridinium bis(2-oxo-2-phenylethylide)

-continued

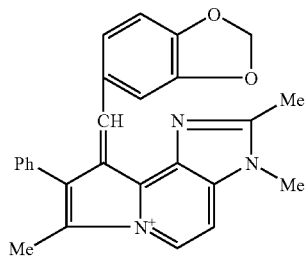

9-(1,3-Benzodioxol-5-ylmethylene)-3,9-dihydro-2,3,7-trimethyl-8-phenyl-imidazo[4,5-g]indolizin-6-ium salt

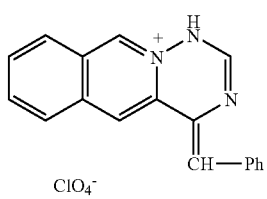

1,4-Dihydro-4-(phenylmethylene)-[1,2,4]triazino[1,6-b]isoquinolin-11-ium perchlorate

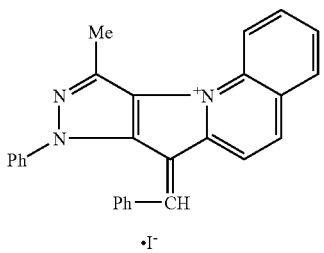

7,8-Dihydro-10-methyl-8-phenyl-7-(phenylmethylene)pyrazolo[3',4':4,5]-pyrrolo[1,2-a]quinolin-11-ium iodide

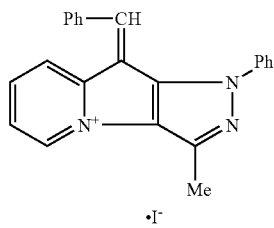

1,9-Dihydro-3-methyl-1-phenyl-9-(phenylmethylene)-pyrazolo[3,4-b]indolizin-4-ium iodide -continued

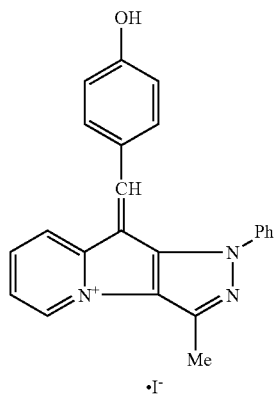

1,9-Dihydro-9-[(4-hydroxyphenyl)-methylene]-3-methyl-1-phenyl-pyrazolo[3,4-b]indolizin-4-ium iodide

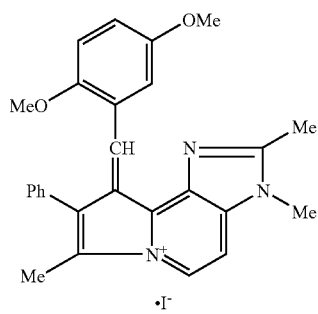

9-[(2,5-Dimethoxyphenyl)methylene]-3,9-dihydro-2,3,7-trimethyl-8-phenyl-imidazo[4,5-g]indolizin-6-ium iodide

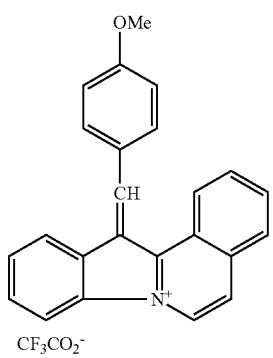

12-[(4-Methoxyphenyl)methylene]-12H-indolo[2,1-a]isoquinolinium trifluoroacetate

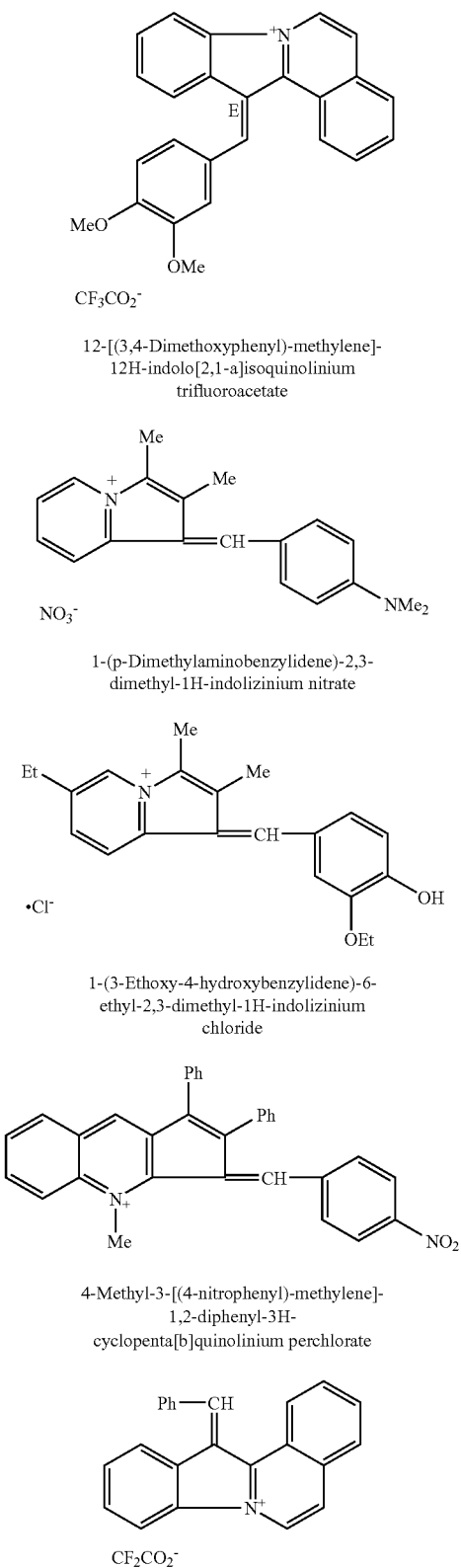

12-[(3,4-Dimethoxyphenyl)-methylene]-
12H-indolo[2,1-a]isoquinolinium
trifluoroacetate 1-(p-Dimethylaminobenzylidene)-2,3-
dimethyl-1H-indolizinium nitrate 1-(3-Ethoxy-4-hydroxybenzylidene)-6-
ethyl-2,3-dimethyl-1H-indolizinium
chloride 4-Methyl-3-[(4-nitrophenyl)-methylene]-
1,2-diphenyl-3H-
cyclopenta[b]quinolinium perchlorate 12-(Phenylmethylene)-12H-indolo[2,1-
a]isoquinolinium trifluoroacetate

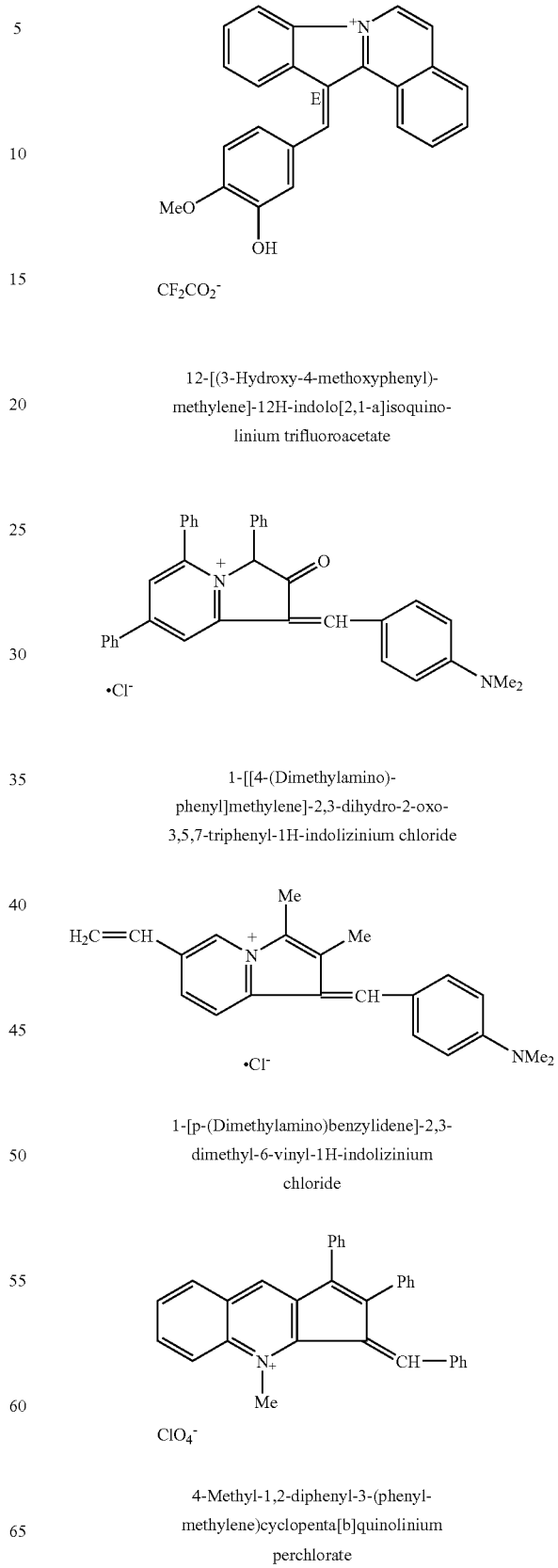

12-[(3-Hydroxy-4-methoxyphenyl)-
methylene]-12H-indolo[2,1-a]isoquino-
linium trifluoroacetate 1-[[4-(Dimethylamino)-
phenyl]methylene]-2,3-dihydro-2-oxo-
3,5,7-triphenyl-1H-indolizinium chloride 1-p-(Dimethylamino)benzylidene]-2,3-
dimethyl-6-vinyl-1H-indolizinium
chloride 4-Methyl-1,2-diphenyl-3-(phenyl-
methylene)cyclopenta[b]quinolinium
perchlorate -continued

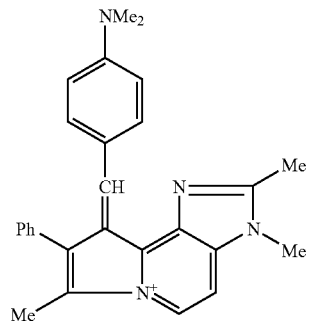

9-[[4-(Dimethylamino)phenyl]-
methylene]-3,9-dihydro-2,3,7-trimethyl-
8-phenylimidazo[4,5-g]indolizin-6-ium
iodide

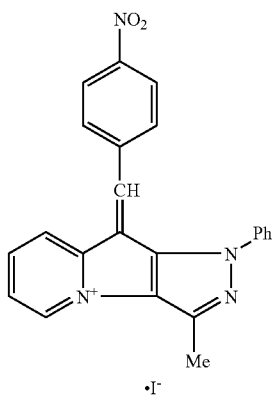

1,9-Dihydro-3-methyl-9-[(4-nitro-
phenyl)methylene]-1-phenyl-
pyrazolo[3,4-b]indolizin-4-ium iodide The anions mentioned in the above table are given merely as examples.

The synthesis of these dyes is known. By way of example, mention may be made of the article Sczepan Phys. Chem. Chem. Phys. 2001, 3, 3555-3561.

The present disclosure also relates to a cosmetic composition comprising the direct dyes of formulae (I) to (V) in a cosmetically acceptable medium, appropriate for the dyeing of keratin fibers, with the exception of the following compounds:

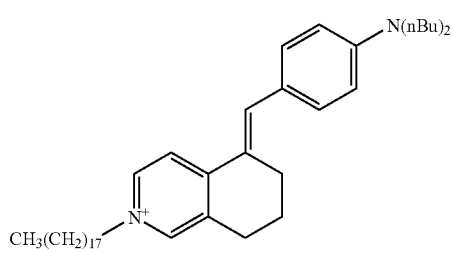

-continued

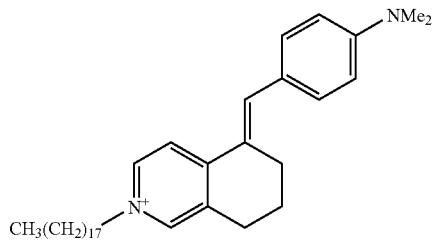

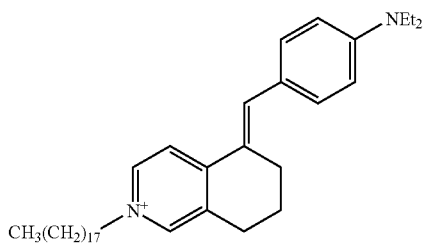

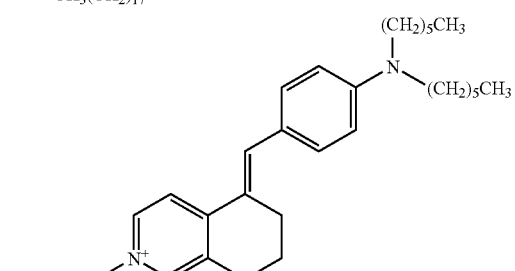

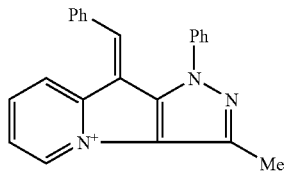

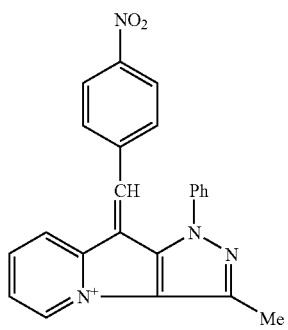

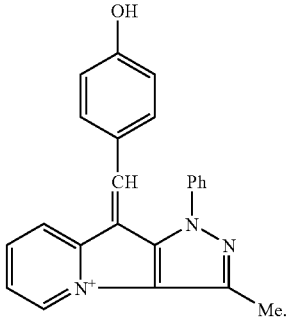

In at least one embodiment, the compositions of the disclosure contain at least one surfactant and/or at least one thickening polymer.

According to at least one embodiment of the present disclosure, the at least one direct dye of formulae (I) to (V) is present in the cosmetic composition in an amount ranging from 0.001% to 20% by weight, such as, for example, from 0.01% to 5% by weight relative to the total weight of the composition.

In at least one embodiment, the cosmetically acceptable medium comprises water or a mixture of water and at least one organic solvent.

Non-limiting examples of organic solvents that may be mentioned include $C_1$-$C_4$ linear or branched alkanols such as ethanol and isopropanol; glycerol; glycols and glycol ethers, for instance 2-butoxyethanol, propylene glycol, dipropylene glycol, propylene glycol monomethyl ether, diethylene glycol monomethyl ether and monoethyl ether, and also aromatic alcohols, for instance benzyl alcohol or phenoxyethanol, similar products and mixtures thereof.

According to at least one embodiment of the present disclosure, the at least one solvent may be present in an amount ranging from 1% to 40% by weight, such as, for example, from 5% to 30% by weight, relative to the total weight of the dye composition.

The pH of the composition in accordance with the disclosure may range from 3 to 12, such as, for example, from 5 to 11. The pH may be adjusted to the desired value by means of acidifying or basifying agents usually used in the dyeing of human keratin fibers.

Non-limiting examples of acidifying agents that may be mentioned include mineral or organic acids, for instance hydrochloric acid, orthophosphoric acid, sulfuric acid, carboxylic acids, for instance acetic acid, tartaric acid, citric acid and lactic acid, and sulfonic acids.

Non-limiting examples of basifying agents that may be mentioned include aqueous ammonia, alkaline carbonates, alkanolamines such as monoethanolamine, diethanolamine and triethanolamine and derivatives thereof, sodium hydroxide, potassium hydroxide and the compounds of formula (VI) below:

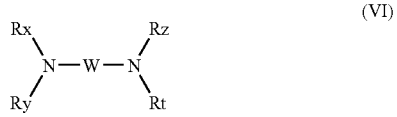

(VI)

wherein:

W is a propylene residue optionally substituted with a hydroxyl group or a $C_1$-$C_6$ alkyl radical; and $R_x$, $R_y$, $R_z$ and $R_t$, which may be identical or different, are chosen from hydrogen atoms, $C_1$-$C_6$ alkyl radicals, and $C_1$-$C_6$ hydroxyalkyl radicals.

The cosmetic composition may also comprise at least one additional direct dye of nonionic, cationic or anionic nature, such as, for example, cationic or nonionic, or combinations thereof.

In at least one embodiment, these direct dyes are chosen from nitrobenzene dyes, azo, azomethine, methine, anthraquinone, naphthoquinone, benzoquinone, phenothiazine, indigoid, xanthene, phenanthridine, phthalocyanin, triarylmethane-based dyes and natural dyes, alone or as mixtures.

The at least one additional direct dye may be chosen, for example, from the following red or orange nitrobenzene dyes:

1-hydroxy-3-nitro-4-N-(γ-hydroxypropyl)aminobenzene,
N-(β-hydroxyethyl)amino-3-nitro-4-aminobenzene,
1-amino-3-methyl-4-N-(β-hydroxyethyl)amino-6-nitrobenzene,
1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitro-para-phenylenediamine,
1-amino-2-nitro-4-(β-hydroxyethyl)amino-5-chlorobenzene,
2-nitro-4-aminodiphenylamine,
1-amino-3-nitro-6-hydroxybenzene,
1-(β-aminoethyl)amino-2-nitro-4-(β-hydroxyethyloxy) benzene,
1-(β,γ-dihydroxypropyl)oxy-3-nitro-4-(β-hydroxyethyl) aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene,
2-nitro-4'-hydroxydiphenylamine, and
1-amino-2-nitro-4-hydroxy-5-methylbenzene.

The composition employed in the case of this embodiment may also comprise, in addition to or instead of these nitrobenzene dyes, at least one additional direct dye chosen from yellow, green-yellow, blue or violet nitrobenzene dyes, azo dyes, anthraquinone dyes, naphthoquinone dyes, benzoquinone dyes, indigoid dyes, and triarylmethane-based dyes.

These additional direct dyes may be basic dyes, among which non-limiting mention may be made of the dyes known in the Color Index, 3rd edition, under the names "Basic Brown 16," "Basic Brown 17," "Basic Yellow 57," "Basic Red 76," "Basic Violet 10," "Basic Blue 26" and "Basic Blue 99," or acidic direct dyes, among which mention may be made of the dyes known in the Color Index, 3rd edition, under the names "Acid Orange 7," "Acid Orange 24," "Acid Yellow 36," "Acid Red 33," "Acid Red 184," "Acid Black 2," "Acid Violet 43" and "Acid Blue 62", or alternatively cationic direct dyes such as those described in International Patent Application Nos. WO 95/01772 and WO 95/15144 and European Patent No. EP 714 954, the content of which forms an integral part of the present disclosure.

Among the additional yellow and green-yellow nitrobenzene direct dyes that may be used according to at least one embodiment of the present disclosure, non-limiting mention may be made, for example, of the compounds chosen from:

1-β-hydroxyethyloxy-3-methylamino-4-nitrobenzene,
1-methylamino-2-nitro-5-(β,γ-dihydroxypropyl)oxybenzene,
1-(β-hydroxyethyl)amino-2-methoxy-4-nitrobenzene,
1-(β-aminoethyl)amino-2-nitro-5-methoxybenzene,
1,3-di(β-hydroxyethyl)amino-4-nitro-6-chlorobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrobenzenesulfonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-(β-ureidoethyl)amino-4-nitrobenzene,
1,3-diamino-4-nitrobenzene,
1-hydroxy-2-amino-5-nitrobenzene,
1-amino-2-[tris(hydroxymethyl)methyl]amino-5-nitrobenzene,
1-(β-hydroxyethyl)amino-2-nitrobenzene, and
4-(β-hydroxyethyl)amino-3-nitrobenzamide.

Among the additional blue or violet nitrobenzene direct dyes that may be used according to at least one embodiment, non-limiting mention may be made, for example, of the compounds chosen from:

1-(β-hydroxyethyl)amino-4-N,N-bis(β-hydroxyethyl) amino-2-nitrobenzene,
1-(γ-hydroxypropyl)amino-4,N,N-bis(β-hydroxyethyl) amino-2-nitrobenzene,
1-(β-hydroxyethyl)amino-4-(N-methyl-N-β-hydroxyethyl)amino-2-nitrobenzene,
1-(β-hydroxyethyl)amino-4-(N-ethyl-N-β-hydroxyethyl) amino-2-nitrobenzene,
1-(β,γ-dihydroxypropyl)amino-4-(N-ethyl-N-β-hydroxyethyl)amino-2-nitrobenzene,
2-nitro-para-phenylenediamines having the following formula:

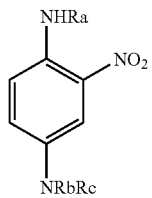

wherein:
$R_b$ is chosen from $C_1$-$C_4$ alkyl radicals, β-hydroxyethyl, β-hydroxypropyl, and γ-hydroxypropyl radicals;
$R_a$ and $R_c$, which may be identical or different, are chosen from β-hydroxyethyl, β-hydroxypropyl, γ-hydroxypropyl and β,γ-dihydroxypropyl radicals, wherein at least one of the radicals $R_b$, $R_c$ or $R_a$ is a γ-hydroxypropyl radical and $R_b$ and $R_c$ are not simultaneously β-hydroxyethyl radicals when $R_b$ is a γ-hydroxypropyl radical, such as those described in French Patent No. FR 2 692 572.

Among the natural direct dyes that may be used according to at least one embodiment, non-limiting mention may be made, inter alia, of henna, camomile and indigo.

When present, the at least one additional direct dye is present in an amount ranging from 0.0005% to 12% by weight, such as, for example, from 0.005% to 6% by weight, relative to the total weight of the composition.

In embodiments where the cosmetic composition is used for oxidation dyeing, the cosmetic composition in accordance with the present disclosure may comprise, in addition, at least one oxidation base chosen from the oxidation bases conventionally used for oxidation dyeing and among which non-limiting mention may be made of para-phenylenediamines, bis(phenyl)alkylenediamines, para-aminophenols, ortho-aminophenols and heterocyclic bases, and the addition salts thereof with an acid or with an alkaline agent.

Among the para-phenylenediamines that may be used according to at least one embodiment, non-limiting mention may be made, for example, of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxy-propyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine and 4'-aminophenyl-1-(3-hydroxy)pyrrolidine, and the addition salts thereof with an acid or with an alkaline agent.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid or with an alkaline agent are used according to at least one embodiment.

Among the bis(phenyl)alkylenediamines that may be used according to at least one embodiment, non-limiting mention may be made, for example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)-tetramethylenediamine, N,N'-bis(4-methylaminophenyl)tetramethylenediamine, N,N'-bis-(ethyl)-N,N'-bis(4'-amino-3'-methylphenyl)ethylenediamine and 1,8-bis(2,5-diaminophenoxy)-3,5-dioxaoctane, and the addition salts thereof with an acid or with an alkaline agent.

Among the para-aminophenols that may be used according to at least one embodiment, non-limiting mention may be made, for example, of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid or with an alkaline agent.

Among the ortho-aminophenols that may be used according to at least one embodiment, non-limiting mention may be made, for example, of 2-aminophenol, 2-amino-5-methylphenol, 2-amino-6-methylphenol and 5-acetamido-2-aminophenol, and the addition salts thereof with an acid or with an alkaline agent.

Among the heterocyclic bases that may be used according to at least one embodiment, non-limiting mention may be made, for example, of pyridine derivatives, pyrimidine derivatives and pyrazole derivatives, and the addition salts thereof with an acid or with an alkaline agent.

When they are used, the at least one oxidation base may be present in an amount ranging from 0.0005% to 12% by weight, such as, for example, from 0.005% to 6% by weight, relative to the total weight of the composition.

In embodiments using the cosmetic composition for oxidation dyeing, the composition in accordance with the present disclosure may also comprise at least one coupler so as to modify or to enrich with glints the shades obtained using the direct dyes and the at least one oxidation base.

The at least one coupler that may be used may be chosen from the couplers conventionally used in oxidation dyeing, and among which non-limiting mention may be made, for example, of meta-phenylenediamines, meta-aminophenols, meta-diphenols and heterocyclic couplers, and the addition salts thereof with an acid or with an alkaline agent.

In at least one embodiment, the at least one coupler is chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, and the addition salts thereof with an acid or with an alkaline agent.

When present, the at least one coupler is present in an amount ranging from 0.0001% to 10% by weight, such as, for example, from 0.005% to 5% by weight, relative to the total weight of the composition.

In at least one embodiment, the addition salts with an acid that may be used in the context of the compositions of the present disclosure (oxidation bases and couplers) are chosen from the hydrochlorides, hydrobromides, sulfates, citrates, succinates, tartrates, tosylates, benzenesulfonates, lactates and acetates.

The addition salts with an alkaline agent that may be used in the context of the compositions of at least one embodiment of the present disclosure (oxidation bases and couplers) are chosen from the addition salts with alkali metals or alkaline-earth metals, with ammonia and with organic amines, including alkanolamines and the compounds of formula (VI).

The composition according to the present disclosure makes it possible to obtain colorations lighter than the original color of the keratin fibers, when it is applied to dark fibers, without the presence of an oxidizing agent being necessary. However, of course, the composition according to the present disclosure may also comprise such an agent.

The cosmetic composition in accordance with the present disclosure may also comprise various adjuvants conventionally used in cosmetic compositions, including those for dyeing human keratin fibers, such as anionic, cationic, nonionic, amphoteric or zwitterionic polymers or mixtures thereof, mineral thickeners, antioxidants, penetrating agents, sequestering agents, fragrances, buffers, dispersants, conditioners, for instance cations, cationic or amphoteric polymers, chitosans, volatile or non-volatile, modified or unmodified silicones, film-forming agents, ceramides, preserving agents, stabilizers and opacifiers.

According to at least one embodiment, the composition may further comprise at least one surfactant. The at least one surfactant may be chosen without preference, alone or as mixtures, from anionic, amphoteric, nonionic, zwitterionic and cationic surfactants.

Among surfactants that may be used according to the present disclosure, non-limiting may be made of the following:

(i) Anionic Surfactants:

By way of example of anionic surfactants that can be used, alone or as mixtures, in the context of the present disclosure, non-limiting mention may be made of salts (for example, alkali metal salts, such as sodium salts, ammonium salts, amine salts, amino alcohol salts or magnesium salts) of the following compounds: alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; ($C_6$-$C_{24}$)alkyl sulfosuccinates, ($C_6$-$C_{24}$)alkyl ether sulfosuccinates, ($C_6$-$C_{24}$)alkylamide sulfosuccinates; ($C_6$-$C_{24}$)alkyl sulfoacetates; ($C_6$-$C_{24}$)acyl sarcosinates; and ($C_6$-$C_{24}$)acyl glutamates. It is also possible to use ($C_6$-$C_{24}$)alkylpolyglycoside carboxylic esters such as alkylglucoside citrates, alkylpolyglycoside tartrates and alkylpolyglycoside sulfosuccinates, alkylsulfosuccinamates; acyl isethionates and N-acyl taurates, the alkyl or acyl radical of all of these different compounds containing, for example, from 12 to 20 carbon atoms and the aryl radical denoting, for example, a phenyl or benzyl group. Among the anionic surfactants which can also be used, non-limiting mention may also be made of fatty acid salts such as oleic, ricinoleic, palmitic and stearic acid salts, coconut oil acid or hydrogenated coconut oil acid; acyl lactylates in which the acyl radical contains 8 to 20 carbon atoms. It is also possible to use alkyl D-galactoside uronic acids and their salts, polyoxyalkylenated ($C_6$-$C_{24}$)alkyl ether carboxylic acids, polyoxyalkylenated ($C_6$-$C_{24}$)alkylaryl ether carboxylic acids, polyoxyalkylenated ($C_6$-$C_{24}$)alkylamido ether carboxylic acids and their salts, such as those containing from 2 to 50 alkylene oxide groups, including ethylene oxide groups, and mixtures thereof.

(ii) Nonionic Surfactants:

The nonionic surfactants also include compounds that are well known per se (see for example "Handbook of Surfactants" by M. R. Porter, published by Blackie & Son (Glasgow and London), 1991, pp. 116-178) and their nature is not a critical factor in the context of the present disclosure. Thus, they can be chosen, for example, from polyethoxylated or polypropoxylated, alkylphenols, alpha-diols or alcohols, having a fatty chain containing, for example, 8 to 18 carbon atoms, it being possible for the number of ethylene oxide or propylene oxide groups to range, for example, from 2 to 50. Non-limiting mention may also be made of copolymers of ethylene oxide and of propylene oxide, condensates of ethylene oxide and of propylene oxide with fatty alcohols; polyethoxylated fatty amides having, for example, from 2 to 30 mol of ethylene oxide, polyglycerolated fatty amides containing on average 1 to 5, such as 1.5 to 4, glycerol groups; polyethoxylated fatty amines having, for example, from 2 to 30 mol of ethylene oxide; oxyethylenated fatty acid esters of sorbitan having, for example, from 2 to 30 mol of ethylene oxide; fatty acid esters of sucrose, fatty acid esters of polyethylene glycol, alkylpolyglycosides, N-alkylglucamine derivatives, and amine oxides such as ($C_{10}$-$C_{14}$)alkylamine oxides or N-acylaminopropylmorpholine oxides.

(iii) Amphoteric or Zwitterionic Surfactants:

The amphoteric or zwitterionic surfactants may be chosen, for example, from aliphatic secondary or tertiary amine derivatives in which the aliphatic radical is a linear or branched chain containing 8 to 18 carbon atoms and containing at least one water-solubilizing anionic group (for example carboxylate, sulfonate, sulfate, phosphate or phosphonate); non-limiting mention may also be made of ($C_8$-$C_{20}$)alkylbetaines, sulfobetaines, ($C_8$-$C_{20}$)alkylamido($C_1$-$C_6$)alkylbetaines or ($C_8$-$C_{20}$)alkyl-amido($C_1$-$C_6$)alkylsulfobetaines.

Among the amine derivatives, non-limiting mention may be made of the products sold under the name MIRANOL, as described in U.S. Pat. Nos. 2,528,378 and 2,781,354 and classified in the CTFA dictionary, 3rd edition, 1982, under the names Amphocarboxyglycinates and Amphocarboxypropionates, with the respective structures:

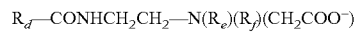

wherein:
$R_d$ is chosen from alkyl radicals of an acid $R_d$—COOH present in hydrolyzed coconut oil, a heptyl, nonyl or undecyl radical, $R_e$ is a beta-hydroxyethyl group and $R_f$ is a carboxymethyl group;

and

wherein:
B is chosen from —CH$_2$CH$_2$OX, C is chosen from —(CH$_2$)$_z$—Y, with z=1 or 2, X is chosen from a —CH$_2$CH$_2$—COOH group and a hydrogen atom, Y is chosen from —COOH and —CH$_2$—CHOH—SO$_3$H radicals, and R$_g$ is chosen from alkyl radicals of an acid R$_h$—COOH present in coconut oil or in hydrolyzed linseed oil, a saturated radical or a radical comprising at least one unsaturation, such as, for example, C$_7$ to C$_{17}$, including a C$_9$, C$_{11}$, C$_{13}$ or C$_{17}$ alkyl radical or its iso form, or an unsaturated C$_{17}$ radical.

These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylamphodipropionate, Disodium Capryloamphodipropionate, Lauroamphodipropionic acid and Cocoamphodipropionic acid.

By way of example, non-limiting mention may be made of the cocoamphodiacetate sold under the trade name Miranol® C$_2$M concentrate by the company Rhodia Chimie.

(iv) Cationic Surfactants:

Among the cationic surfactants, non-limiting mention may be made of: salts of optionally polyoxyalkylenated primary, secondary or tertiary fatty amines; quaternary ammonium salts such as tetraalkylammonium, alkylamidoalkyltrialkylammonium, trialkylbenzylammonium, trialkylhydroxyalkylammonium, or alkylpyridinium, chlorides or bromides; imidazoline derivatives; or amine oxides of cationic nature.

In at least one embodiment, the at least one surfactant is nonionic, anionic or amphoteric.

According to at least one embodiment, the at least one surfactant is present in an amount ranging from 0.01% and 50% by weight, such as, for example, from 0.1% to 25% by weight, relative to the total weight of the composition.

The composition may also comprise at least one thickening polymer. The at least one thickening polymer may be ionic or nonionic, and associative or non-associative.

As regards the at least one non-associative thickening polymer, it is first of all recalled that, for the purposes of the present disclosure, non-associative thickening polymers are thickening polymers not containing a C$_{10}$-C$_{30}$ fatty chain.

Among the at least one non-associative thickening polymers present, non-limiting mention may be made of crosslinked acrylic acid homopolymers, crosslinked 2-acrylamido-2-methylpropanesulfonic acid homopolymers and the crosslinked acrylamide copolymers thereof, ammonium acrylate homopolymers or copolymers of ammonium acrylate and of acrylamide, nonionic guar gums, biopolysaccharide gums of microbial origin, gums originating from plant exudates, hydroxypropyl- or carboxymethyl celluloses; pectins and alginates, alone or as mixtures.

According to at least one embodiment, suitable non-associative thickening polymers include crosslinked acrylic acid homopolymers.

Among the homopolymers of this type that may be used according to at least one embodiment, non-limiting mentioned may be made of those crosslinked with an allylic ether of an alcohol of the sugar series, for instance the products sold under the names CARBOPOL 980, 981, 954, 2984 and 5984 by the company Noveon, or the products sold under the names SYNTHALEN M and SYNTHALEN K by the company 3 VSA.

Non-associative thickening polymers may also be chosen from crosslinked 2-acrylamido-2-methylpropanesulfonic acid homopolymers and the crosslinked acrylamide copolymers thereof.

Among these homopolymers and copolymers, which may be partially or totally neutralized, non-limiting mention may be made of polymers comprising from 90% to 99.9% by weight, relative to the total weight of polymer, of units of formula (j) below:

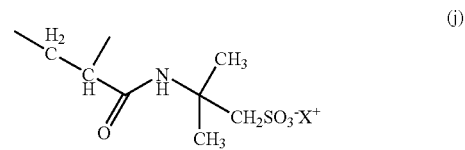

(j)

wherein X$^+$ is a cation or a mixture of cations, or a proton.

In at least one embodiment, the cations are chosen from alkali metals (for instance sodium, or potassium), ammonium ions optionally substituted with 1 to 3 alkyl radicals, which may be identical or different, containing from 1 to 6 carbon atoms, optionally bearing at least one hydroxyl radical, cations derived from N-methylglucamine or from basic amino acids, for instance arginine and lysine. In at least one embodiment, the cation is an ammonium or sodium ion.

According to at least one embodiment, the polymer comprises from 0.01% to 10% by weight, relative to the total weight of the polymer, of crosslinking units derived from at least one monomer containing at least two ethylenic unsaturations (carbon-carbon double bond).

Crosslinking monomers containing at least two ethylenic unsaturations are chosen, for example, from diallyl ether, triallyl cyanurate, diallyl maleate, allyl (meth)acrylate, dipropylene glycol diallyl ether, polyglycol diallyl ethers, triethylene glycol divinyl ether, hydroquinone diallyl ether, tetraallyloxyethane, tetra- or diethylene glycol di(meth)acrylate, triallylamine, tetraallylethylenediamine, trimethylolpropanediallyl ether, trimethylolpropane triacrylate, methylenebis(meth)acrylamide or divinylbenzene, allylic ethers of alcohols of the sugar series, or other allylic or vinyl ethers of polyfunctional alcohols, and also allylic esters of phosphoric and/or vinylphosphonic acid derivatives, or mixtures of these compounds.

For further details regarding these polymers, reference may be made to European Patent No. EP 815 828.

Among the partially or totally neutralized crosslinked copolymers of 2-acrylamido-2-methylpropanesulfonic acid and of acrylamide, non-limiting mention may be made of the product described in Example 1 of European Patent No. EP 503 853, and reference may be made to the document as regards these polymers.

The composition may also comprise, as non-associative thickening polymers, ammonium acrylate homopolymers or copolymers of ammonium acrylate and of acrylamide.

Among the ammonium, acrylate homopolymers that may be used according to at least one embodiment, non-limiting mention may be made of the product sold under the name MICROSAP PAS 5193 by the company Hoechst. Among the copolymers of ammonium, acrylate and of acrylamide that may be used according to at least one embodiment, non-limiting mention may be made of the product sold under the name BOZEPOL C NOUVEAU or the product PAS 5193 sold by the company Hoechst. Reference may also be made to French Patent No. FR 2 416 723, and U.S. Pat. Nos. 2,798,053 and 2,923,692 as regards the description and preparation of such compounds.

The composition may also comprise dimethylaminoethyl methacrylate homopolymers quaternized with methyl chloride or dimethylaminoethyl methacrylate copolymers quaternized with methyl chloride and acrylamide.

Among the homopolymers of this type, non-limiting mention may be made of the products sold under the names SALCARE 95 and SALCARE 96 by the company Ciba-Allied Colloids. Among the copolymers of this family, non-limiting mention may be made of the product SALCARE SC92 sold by Ciba-Allied Colloids or the product PAS 5194 sold by Hoechst. These polymers are described and prepared in European Patent No. EP 395 282, to which reference may be made.

The composition may also comprise nonionic guar gums, for instance the unmodified nonionic guar gums sold under the name VIDOGUM GH 175 by the company Unipectine and under the name JAGUAR C by the company Meyhall.

The nonionic guar gums that may be used according to at least one embodiment of the present disclosure may be modified with $C_1$-$C_6$ hydroxyalkyl groups. Among the hydroxyalkyl groups that may be mentioned, for example, are hydroxymethyl, hydroxyethyl, hydroxypropyl and hydroxybutyl groups.

These guar gums are well known in the prior art and can be prepared, for example, by reacting the corresponding alkene oxides such as, for example, propylene oxides, with the guar gum so as to obtain a guar gum modified with hydroxypropyl groups.

In at least one embodiment, the degree of hydroxyalkylation, which corresponds to the number of alkylene oxide molecules consumed by the number of free hydroxyl functions present on the guar gum, ranges from 0.4 to 1.2.

Such nonionic guar gums optionally modified with hydroxyalkyl groups are sold, for example, under the trade names JAGUAR HP8, JAGUAR HP60 and JAGUAR HP120, JAGUAR DC 293 and JAGUAR HP 105 by the company Meyhall or under the name GALACTASOL 4H4FD2 by the company Aqualon.

As examples of suitable non-associative thickening polymers, non-limiting mention may also be made of biopolysaccharide gums of microbial origin, such as scleroglucan gum or xanthan gum.

Gums derived from plant exudates, such as gum arabic, ghatti gum, karaya gum and gum tragacanth; hydroxypropyl- or carboxymethyl celluloses; pectins and alginates, are also suitable.

These polymers are well known to those skilled in the art and are described in Robert L. Davidson's book entitled "Handbook of Water soluble gums and resins" published by the McGraw-Hill Book Company (1980).

Among the thickeners that are used according to at least one embodiment, non-limiting mention may be made of thickening systems based on associative polymers that are well known to those skilled in the art, such as those of non-ionic, anionic, cationic or amphoteric nature.

As defined herein, associative polymers are hydrophilic polymers capable, in an aqueous medium, of reversibly associating with each other or with other molecules. In at least one embodiment, their chemical structure comprises at least one hydrophilic region and at least one hydrophobic region. In the context of the present disclosure, the term "hydrophobic group" means a radical or polymer containing a saturated or unsaturated, linear or branched, hydrocarbon-based chain containing at least 10 carbon atoms, such as, for example, from 10 to 30 carbon atoms, from 12 to 30 carbon atoms or from 18 to 30 carbon atoms. In at least one embodiment, the hydrocarbon-based group originates from a monofunctional compound. By way of example, the hydrophobic group may be derived from a fatty alcohol such as stearyl alcohol, dodecyl alcohol or decyl alcohol. It may also denote a hydrocarbon-based polymer, for instance polybutadiene.

The composition may thus comprise at least one associative polymer chosen from associative polyurethanes, which may be, for example, cationic or nonionic, associative cellulose derivatives, which can be cationic or nonionic, associative vinyllactams, associative unsaturated polyacids, associative aminoplast-ethers, associative polymers or copolymers comprising at least one ethylenically unsaturated monomer containing a sulfonic group, alone or as mixtures.

Among the associative thickening polymers that may be used according to at least one embodiment, non-limiting mention may be made of associative polyurethane derivatives, for instance those obtained by polymerization:

about 20% to 70% by weight of an α,β-monoethylenically unsaturated carboxylic acid, about 20% to 80% by weight of a non-surfactant α,β-monoethylenically unsaturated monomer, which is different from the previous monomer, about 0.5% to 60% by weight of a nonionic monourethane, which is the product of reaction of a monohydroxylated surfactant with a monoethylenically unsaturated monoisocyanate.

Such polymers are described, for example, in European Patent No. EP 173 109, including Example 3. This polymer is a methacrylic acid/methyl acrylate/dimethyl meta-isopropenyl benzyl isocyanate terpolymer of ethoxylated behenyl alcohol (40 EO) as an aqueous 25% dispersion. This product is sold under the name VISCOPHOBE DB1000 by the company Amerchol.

Cationic associative polyurethanes, the family of which has been described in French Patent Application No. FR 00/09609, now issued as French Patent No. 2 811 993, are also suitable for use. It may be represented, for example, by the formula (A) below:

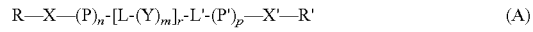

$$R—X—(P)_n-[L-(Y)_m]_r-L'-(P')_p—X'—R' \quad (A)$$

wherein:

R and R', which may be identical or different, are chosen from hydrophobic groups and hydrogen atoms;

X and X', which may be identical or different, are chosen from groups comprising an amine function optionally bearing a hydrophobic group, or alternatively a group L";

L, L' and L", which may be identical or different, are chosen from groups derived from a diisocyanate;

P and P', which may be identical or different, are chosen from groups comprising an amine function optionally bearing a hydrophobic group;

Y is chosen from hydrophilic groups;

r is an integer ranging from 1 to 100, such as, for example, from 1 and 50 or from 1 to 25;

n, m and p each range, independently of each other, from 0 to 1000;

the molecule containing at least one protonated or quaternized amine function and at least one hydrophobic group.

In at least one embodiment of these polyurethanes, the only hydrophobic groups are the groups R and R' at the chain ends.

According to at least one embodiment, the associative polyurethane corresponds to formula (A) in which R and R' both independently represent a hydrophobic group; X and X' are each chosen from a group L"; n and p range from 1 to 1000, and L, L', L", P, P', Y and m have the meaning given as in formula (A).

According to at least one embodiment of the present disclosure, the associative polyurethane corresponds to formula (A) in which R and R' both independently are chosen from hydrophobic groups, X and X' are each chosen from group L", n and p are 0, and L, L', L", Y and m have the meaning as in formula (A) indicated previously.

The fact that n and p are 0 means that these polymers do not comprise units derived from a monomer containing an amine function, incorporated into the polymer during the polycondensation. The protonated amine functions of these polyurethanes result from the hydrolysis of excess isocyanate functions, at the chain end, followed by alkylation of the primary amine functions formed with alkylating agents containing a hydrophobic group, i.e., compounds of the type RQ or R'Q, wherein R and R' are as defined above and Q is a leaving group such as a halide, a sulfate, etc.

In accordance with at least one embodiment of the present disclosure, the associative polyurethane corresponds to formula (A) wherein R and R' both independently are chosen from hydrophobic groups; X and X' both independently are chosen from groups comprising a quaternary amine; n and p are zero and L, L', Y and m have the meaning indicated in formula (A).

In at least one embodiment, the number-average molecular mass of the cationic associative polyurethanes ranges from 400 to 500,000, such as, for example, from 1000 to 400,000 or from 1000 to 300,000 g/mol.

When X and/or X' are chosen from groups comprising a tertiary or quaternary amine, X and/or X' may be chosen from one of the following formulae:

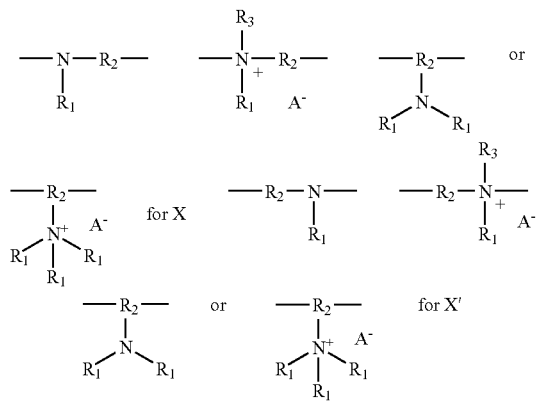

wherein:
$R_2$ is chosen from linear and branched alkylene radicals comprising from 1 to 20 carbon atoms, optionally comprising a saturated or unsaturated ring, or an arylene radical, at least one of the carbon atoms optionally being replaced with a hetero atom chosen from N, S, O and P;
$R_1$ and $R_3$, which may be identical or different, are chosen from linear and branched $C_1$-$C_{30}$ alkyl and alkenyl radicals and aryl radicals, at least one of the carbon atoms optionally being replaced with a heteroatom chosen from N, S, O and P;
$A^-$ is a physiologically acceptable counterion.

The groups L, L' and L" are chosen from groups of formula:

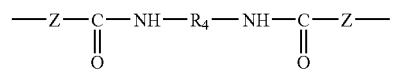

wherein:
Z is chosen from —O—, —S— and —NH—; and $R_4$ is chosen from linear and branched alkylene radicals comprising from 1 to 20 carbon atoms, optionally comprising a saturated or unsaturated ring, or an arylene radical, at least one of the carbon atoms optionally being replaced with a hetero atom chosen from N, S, O and P.

The groups P and P' comprising an amine function may be chosen from at least one of the following formulae:

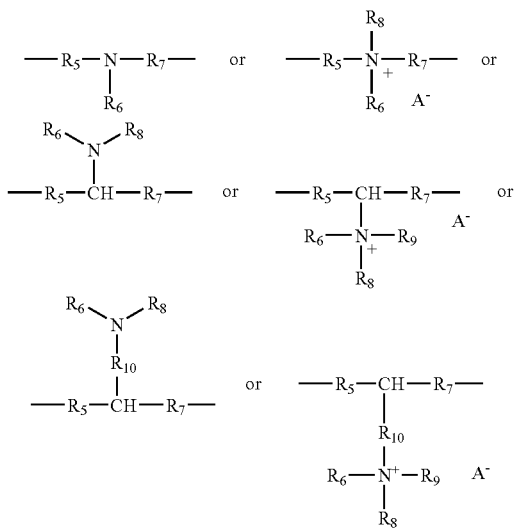

wherein:
$R_5$ and $R_7$ have the same meanings as $R_2$ defined above;
$R_6$, $R_8$ and $R_9$ have the same meanings as $R_1$ and $R_3$ defined above;
$R_{10}$ is chosen from linear and branched, optionally unsaturated alkylene groups optionally comprising at least one hetero atom chosen from N, O, S and P; and
$A^{31}$ is a cosmetically acceptable counterion.

In the context of the present disclosure, in the meaning of Y, the term "hydrophilic group" means a polymeric or non-polymeric water-soluble group. By way of example, when it is not a polymer, non-limiting mention may be made of ethylene glycol, diethylene glycol and propylene glycol. When it is a hydrophilic polymer, in accordance with at least one embodiment, non-limiting mention may be made, for example, of polyethers, sulfonated polyesters, sulfonated polyamides or a mixture of these polymers. In at least one embodiment, the hydrophilic compound is a polyether, such as poly(ethylene oxide) or poly(propylene oxide).

The associative polyurethanes of formula (A) are formed from diisocyanates and from various compounds with functions containing a labile hydrogen. The functions containing a labile hydrogen may be alcohol, primary or secondary amine or thiol functions, giving, after reaction with the diisocyanate functions, polyurethanes, polyureas and polythioureas, respectively. The expression "polyurethanes" which can be used according to the present disclosure encompasses these three types of polymer, namely polyurethanes per se, polyureas and polythioureas, and also copolymers thereof.

A first type of compound included in the preparation of the polyurethane of formula (A) is a compound comprising at least one unit containing an amine function. This compound may be multifunctional, but in at least one embodiment, the compound is difunctional, that is to say that this compound comprises two labile hydrogen atoms borne, for example, by a hydroxyl, primary amine, secondary amine or thiol function. A mixture of multifunctional and difunctional compounds in which the percentage of multifunctional compounds is low may also be used.

As mentioned above, this compound may comprise more than one unit containing an amine function. In this case, it is a polymer bearing a repetition of the unit containing an amine function.

Compounds of this type may be represented by one of the following formulae:

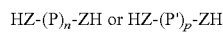

wherein Z, P, P', n and p are as defined above.

Examples of compounds containing an amine function that may be mentioned include N-methyldiethanolamine, N-tert-butyldiethanolamine and N-sulfoethyldi-ethanolamine.

The second compound included in the preparation of the polyurethane of formula (A) is a diisocyanate corresponding to the formula O=C=N—$R_4$—N=C=O, wherein $R_4$ is as defined above.

Non-limiting mention may be made of methylenediphenyl diisocyanate, methylenecyclohexane diisocyanate, isophorone diisocyanate, toluene diisocyanate, naphthalene diisocyanate, butane diisocyanate and hexane diisocyanate.

A third compound included in the preparation of the polyurethane of formula (A) is a hydrophobic compound intended to form the terminal hydrophobic groups of the polymer of formula (A). This compound comprises a hydrophobic group and a function comprising a labile hydrogen, for example a hydroxyl, primary or secondary amine, or thiol function. By way of example, this compound may be a fatty alcohol such as, for example, stearyl alcohol, dodecyl alcohol or decyl alcohol. When this compound comprises a polymeric chain, it may be, for example, α-hydroxylated hydrogenated polybutadiene.

The hydrophobic group of the polyurethane of formula (A) may also result from the quaternization reaction of the tertiary amine of the compound comprising at least one tertiary amine unit. Thus, the hydrophobic group is introduced via the quaternizing agent. This quaternizing agent is a compound of the type RQ or R'Q, wherein R and R' are as defined above and Q is chosen from leaving groups such as a halide, a sulfate, etc.

The cationic associative polyurethane may also comprise a hydrophilic block. This block is provided by a fourth type of compound involved in the preparation of the polymer. This compound may be multifunctional. In at least one embodiment, the compound is difunctional. It is also possible to have a mixture in which the percentage of multifunctional compound is low.

The functions containing a labile hydrogen may be alcohol, primary or secondary amine or thiol functions. This compound may be a polymer terminated at the chain ends with one of these functions containing a labile hydrogen.

By way of example, when it is not a polymer, non-limiting mention may be made of ethylene glycol, diethylene glycol and propylene glycol.

When it is a hydrophilic polymer, non-limiting mention may be made, for example, of polyethers, sulfonated polyesters and sulfonated polyamides, or a mixture of these polymers.

In at least one embodiment, the hydrophilic compound is a polyether, such as poly(ethylene oxide) or poly(propylene oxide).

The hydrophilic group termed Y in formula (A) is optional. In at least one embodiment, the units containing a quaternary amine or protonated function may suffice to provide the solubility or water-dispersibility required for this type of polymer in an aqueous solution.

Although the presence of a hydrophilic group Y is optional, cationic associative polyurethanes comprising such a group are used in at least one embodiment.

The associative polyurethane derivatives used in at least one embodiment of the present disclosure may also be nonionic polyurethane polyethers. According to at least one embodiment, the polymers comprise in their chain both hydrophilic blocks usually of polyoxyethylenated nature, and hydrophobic blocks that may be aliphatic chains alone and/or cycloaliphatic and/or aromatic chains.

In at least one embodiment, these polyurethane polyethers comprise at least two hydrocarbon-based lipophilic chains, comprising from 6 to 30 carbon atoms, separated by a hydrophilic block, the hydrocarbon-based chains possibly being pendent chains or chains at the end of a hydrophilic block. In at least one embodiment, it is possible for at least one pendent chain to be provided. In addition, the polymer may comprise a hydrocarbon-based chain at one or both ends of a hydrophilic block.

The polyurethane polyethers may be multiblock, such as triblock form. The hydrophobic blocks may be at each end of the chain (for example, triblock copolymer containing a hydrophilic central block) or distributed both at the ends and in the chain (for example, multiblock copolymer). These same polymers may also be graft polymers or starburst polymers.

The fatty-chain nonionic polyurethane polyethers may be triblock copolymers whose hydrophilic block is a polyoxyethylenated chain comprising from 50 to 1000 oxyethylenated groups.

The nonionic polyurethane polyethers comprise a urethane bond between the hydrophilic blocks, whence arises the name.

By extension, the hydrophobic-chain nonionic polyurethane polyethers may also be chosen from those whose hydrophilic blocks are linked to the hydrophobic blocks via other chemical bonds.

As examples of hydrophobic-chain nonionic polyurethane polyethers that may be used in the present disclosure, non-limiting mention may also be made of Rheolate 205® containing a urea function, sold by the company Rheox, or alternatively Rheolates® 208, 204 or 212 or Acrysol RM 184®.

Non-limiting mention may also be made of the product Elfacos T210® containing a $C_{12-14}$ alkyl chain and the product Elfacos T212® containing a $C_{18}$ alkyl chain, from Akzo.

The product DW 1206B® from Rohm & Haas containing a $C_{20}$ alkyl chain and a urethane linkage, sold at a solids content of 20% in water, may also be used.

It is also possible to use solutions or dispersions of these polymers, such as in water or in aqueous-alcoholic medium. Non-limiting examples of such polymers that may be mentioned are Rheolate® 255, Rheolate® 278 and Rheolate® 244 sold by the company Rheox. The products DW 1206F and DW 1206J sold by the company Rohm & Haas may also be used.

The polyurethane polyethers that may be used may also be chosen from those described in the article by G. Formum, J. Bakke and Fk. Hansen—Colloid Polym. Sci. 271, 380-389 (1993).

According to at least one embodiment of the present disclosure, use may be made of a polyurethane polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold, for example, by the company Rohm & Haas under the names Aculyn 46® and Aculyn 44® (Aculyn 46® is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44® is a polycondensate of polyethylene glycol containing 150 or 180 mol of ethylene oxide, of decyl alcohol and of methylenebis(4-cyclohexylisocyanate) (SMDI), at 35% by weight in a mixture of propylene glycol (39%) and water (26%)).

The composition may also comprise polymers derived from associative celluloses, such as:
  quaternized cationic celluloses modified with groups comprising at least one hydrophobic chain, such as alkyl, arylalkyl or alkylaryl groups containing at least 8 carbon atoms, or mixtures thereof,
  quaternized cationic hydroxyethylcelluloses modified with groups comprising at least one hydrophobic chain, such as alkyl, arylalkyl or alkylaryl groups containing at least 8 carbon atoms, or mixtures thereof.

In at least one embodiment, the alkyl radicals borne by the above quaternized celluloses or hydroxyethylcelluloses contain from 8 to 30 carbon atoms. According to at least one embodiment, the aryl radicals are chosen from phenyl, benzyl, naphthyl and anthryl groups.

Non-limiting examples of quaternized alkylhydroxyethylcelluloses containing $C_8$-$C_{30}$ hydrophobic chains that may be mentioned include the products Quatrisoft LM 200®, Quatrisoft LM-X 529-18-A®, Quatrisoft LM-X 529-18B® ($C_{12}$ alkyl) and Quatrisoft LM-X 529-8® ($C_{18}$ alkyl) sold by the company Amerchol, and the products Crodacel QM®, Crodacel QL® ($C_{12}$ alkyl) and Crodacel QS® ($C_{18}$ alkyl) sold by the company Croda.
  nonionic cellulose derivatives such as hydroxyethyl celluloses modified with groups comprising at least one hydrophobic chain, such as alkyl, arylalkyl or alkylaryl groups, or mixtures thereof, and in which the alkyl groups are, for example, of $C_8$-$C_{22}$, for instance the product Natrosol Plus Grade 330 CS® ($C_{16}$ alkyls) sold by the company Aqualon, or the product Bermocoll EHM 100® sold by the company Berol Nobel,
  cellulose derivatives modified with polyalkylene glycol alkylphenol ether groups, such as the product Amercell Polymer HM-1500® sold by the company Amerchol.

Regarding the associative polyvinyllactams, non-limiting examples that may be mentioned include the polymers described, for example, in French Patent Application No. FR 01/01106, now issued as French Patent No. 2,820,032. In at least one embodiment, the polymers are cationic polymers and comprise:
  a) at least one monomer of vinyllactam or alkylvinyllactam type;
  b) at least one monomer of structure (a) or (b) below:

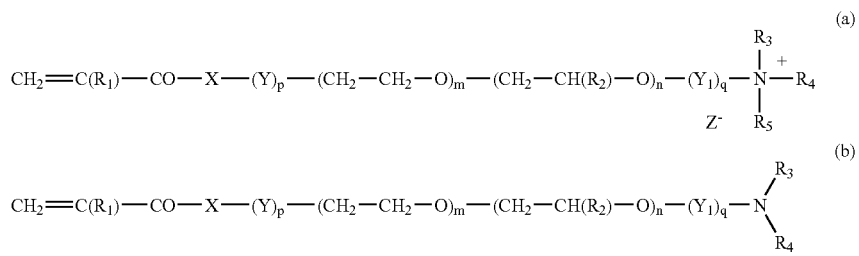

wherein:
X is chosen from oxygen atoms and radicals $NR_6$,
$R_1$ and $R_6$ are chosen from, independently of each other, hydrogen atoms and linear and branched $C_1$-$C_5$ alkyl radicals,
$R_2$ is chosen from linear and branched $C_1$-$C_4$ alkyl radicals,
$R_3$, $R_4$ and $R_5$ are chosen from, independently of each other, hydrogen atoms, linear and branched $C_1$-$C_{30}$ alkyl radicals and radicals of formula (c):

Y, $Y_1$ and $Y_2$ are chosen from, independently of each other, linear and branched $C_2$-$C_{16}$ alkylene radicals,
$R_7$ is chosen from hydrogen atoms, linear and branched $C_1$-$C_4$ alkyl radicals, and linear and branched $C_1$-$C_4$ hydroxyalkyl radicals,
$R_8$ is chosen from hydrogen atoms and linear and branched $C_1$-$C_{30}$ alkyl radicals,
p, q and r are chosen from, independently of each other, either the value 0 or the value 1,
m and n are chosen from, independently of each other, integers ranging from 0 to 100,
x is an integer ranging from 1 to 100,
Z is chosen from organic and mineral acid anions,
with the proviso that:
at least one of the substituents $R_3$, $R_4$, $R_5$ or $R_8$ is chosen from linear and branched $C_9$-$C_{30}$ alkyl radicals,
if m or n is other than zero, then q is equal to 1,
if m or n is equal to zero, then p or q is equal to 0.

The poly(vinyllactam) polymers may be crosslinked or non-crosslinked and may also be block polymers.

In at least one embodiment, the counterion $Z^-$ of the monomers of formula (b) is chosen from halide ions, phosphate ions, the methosulfate ion and the tosylate ion.

In at least one embodiment, $R_3$, $R_4$ and $R_5$ are chosen from, independently of each other, hydrogen atoms and linear and branched $C_1$-$C_{30}$ alkyl radicals.

According to at least one embodiment, the monomer b) is a monomer of formula (b) for which m and n are equal to zero.

In at least one embodiment, the vinyllactam or alkylvinyllactam monomer is a compound of structure (d):

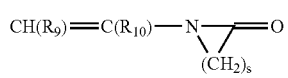

wherein:
s is an integer ranging from 3 to 6,
$R_9$ is chosen from hydrogen atoms and $C_1$-$C_5$ alkyl radicals,
$R_{10}$ is chosen from hydrogen atoms and $C_1$-$C_5$ alkyl radicals,
with the proviso that at least one of the radicals $R_9$ and $R_{10}$ is a hydrogen atom.

In at least one embodiment, the monomer (d) is vinylpyrrolidone.

The poly(vinyllactam) polymers may also contain at least one additional monomer, such as, for example, cationic or nonionic monomers.

As compounds that are used according to at least one embodiment of the present disclosure, non-limiting mention may be made of the following terpolymers comprising at least:
  a) one monomer of formula (d),
  b) one monomer of formula (a) in which p=1, q=0, $R_3$ and $R_4$ are chosen from, independently of each other, hydrogen atoms and $C_1$-$C_5$ alkyl radicals and $R_5$ is chosen from $C_9$-$C_{24}$ alkyl radicals, and
  c) a monomer of formula (b) in which $R_3$ and $R_4$ are chosen from, independently of each other, hydrogen atoms and $C_1$-$C_5$ alkyl radicals.

In at least one embodiment, terpolymers comprising, by weight, 40% to 95% of monomer (d), 0.1% to 55% of monomer (a) and 0.25% to 50% of monomer (b) are used.

Such polymers are described, for example, in International Patent Application No. WO 00/68282, which is incorporated by reference herein.

As poly(vinyllactam) polymers, vinylpyrrolidone/dimethylaminopropyl-methacrylamide/dodecyldimethyl-methacrylamidopropylammonium, tosylate terpolymers, vinylpyrrolidone/dimethylaminopropylmethacrylamide/cocoyldimethylmethacrylamido-propylammonium, tosylate terpolymers, vinylpyrrolidone/dimethylaminopropyl-methacryl-amide/lauryidimethylmethacrylami-dopropylammonium, tosylate or chloride terpolymers are used in at least one embodiment. The vinylpyrrolidone/dimethylaminopropylmethacryl-amide/lauryldimethyl-methacrylamidopropylammonium, chloride terpolymer is sold at a concentration of 20% in water by the company ISP under the name STYLEZE W20.

The associative polyvinyllactam derivatives of the disclosure may also be nonionic copolymers of vinylpyrrolidone and of hydrophobic monomers comprising a hydrophobic chain, among which non-limiting mention may be made, for example, of:
  the products Antaron V216® or Ganex V216® vinylpyrrolidone/hexadecene copolymer) sold by the company ISP,
  the products Antaron V220® or Ganex V220® (vinylpyrrolidone/eicosene copolymer) sold by the company ISP.

Among the associative unsaturated polyacid derivatives that may be used according to at least one embodiment, non-limiting mention may be made of those comprising at least one hydrophilic unit of unsaturated olefinic carboxylic acid type, and at least one hydrophobic unit of unsaturated carboxylic acid ($C_{10}$-$C_{30}$) alkyl ester type.

According to at least one embodiment, these polymers are chosen from those in which the hydrophilic unit of unsaturated olefinic carboxylic acid type corresponds to the monomer of formula (e) below:

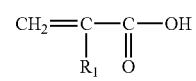

wherein $R_1$ is chosen from H, $CH_3$ and $C_2H_5$, i.e., acrylic acid, methacrylic acid or ethacrylic acid units, and wherein the hydrophobic unit of the type ($C_{10}$-$C_{30}$) alkyl ester of an unsaturated carboxylic acid corresponds to the monomer of formula (f) below:

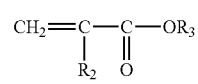

wherein $R_2$ is chosen from H, $CH_3$ and $C_2H_5$ (i.e., acrylate, methacrylate or ethacrylate units), such as, for example, H (acrylate units) or $CH_3$ (methacrylate units), and $R_3$ is chosen from $C_{10}$-$C_{30}$ alkyl radicals, such as, for example, $C_{12}$-$C_{22}$ alkyl radicals.

($C_{10}$-$C_{30}$)Alkyl esters of unsaturated carboxylic acids comprise, for example, lauryl acrylate, stearyl acrylate, decyl acrylate, isodecyl acrylate, and dodecyl acrylate, and the corresponding methacrylates, lauryl methacrylate, stearyl methacrylate, decyl methacrylate, isodecyl methacrylate and dodecyl methacrylate.

Anionic polymers of this type are disclosed and prepared, for example, according to U.S. Pat. Nos. 3,915,921 and 4,509,949.

Among anionic associative polymers of this type, at least one embodiment makes use of polymers formed from a mixture of monomers comprising:
  essentially acrylic acid,
  an ester of formula (f) described above, wherein $R_2$ is chosen from H and $CH_3$, and $R_3$ is chosen from alkyl radicals comprising from 12 to 22 carbon atoms, and
  a crosslinking agent, which is a well-known copolymerizable polyethylenic unsaturated monomer, for instance diallyl phthalate, allyl (meth)acrylate, divinylbenzene, (poly)ethylene glycol dimethacrylate or methylenebisacrylamide.

Among the anionic associative polymers of this type that may be used according to at least one embodiment, non-limiting mention may be made of those comprising from 95% to 60% by weight of acrylic acid (hydrophilic unit), 4% to 40% by weight of $C_{10}$-$C_{30}$ alkyl acrylate (hydrophobic unit) and 0% to 6% by weight of crosslinking polymerizable monomer, or alternatively those comprising from 98% to 96% by weight of acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer such as those described above.

Among the above polymers, at least one embodiment uses the products chosen from those sold by the company Goodrich under the trade names Pemulen TR[1]®, Pemulen TR[2]® and Carbopol 1382®, such as, for example, Pemulen TR[1]®, and the product sold by the company SEPPIC under the name Coatex SX®.

Among the associative unsaturated polyacid derivatives that may also be used in at least one embodiment, non-limiting mention may be made of those comprising among their monomers an α,β-monoethylenically unsaturated carboxylic acid and an ester of an α,β-monoethylenically unsaturated carboxylic acid and of an oxyalkylenated fatty alcohol.

These compounds may comprise as monomer an ester of an α,β-mono-ethylenically unsaturated carboxylic acid and of a $C_1$-$C_4$ alcohol.

A non-limiting example of compounds of this type that may be mentioned is Aculyn 22® sold by the company Rohm & Haas, which is a methacrylic acid/ethyl acrylate/oxyalkylenated stearyl methacrylate terpolymer.

Among the thickening polymers of the aminoplast-ether type, non-limiting mention may be made of any product derived from the condensation of an aldehyde with an amine or an amide, and any structural unit formed from an aminoplast residue and from a divalent hydrocarbon-based residue linked to the aminoplast residue via an ether bond.

The polymers with an aminoplast-ether skeleton used in at least one embodiment are chosen from those containing at least one unit of structure (g) below:

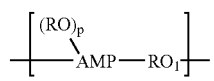

(g)

wherein:
AMP is an aminoplast residue with alkylene units (or divalent alkyl),
R is chosen from hydrogen atoms, $C_1$-$C_4$ alkyl radicals and $C_1$-$C_4$ acyl radicals,
$RO_1$ is a divalent alkyleneoxy residue,
p is a positive integer,
the group(s) OR being linked to the alkylene units of the AMP residue.

In at least one embodiment, the polymers with an aminoplast-ether skeleton are chosen from those containing at least one unit of structure (h) below:

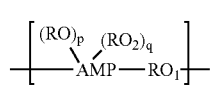

(h)

wherein:
AMP, R, $RO_1$ and p have the same meaning as above,
$RO_2$ is a group other than RO linked to AMP via a hetero atom and comprising at
least two carbon atoms, and
q is a positive integer.

In at least one embodiment, the polymers correspond to formulae (m) and (n) below:

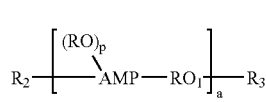

(m)

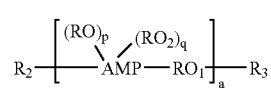

(n)

wherein:
AMP, R, $RO_1$, $RO_2$, p and q have the same meaning as above,
$R_2$ or $R_3$, which may be identical or different, are chosen from end groups that can denote a hydrogen atom, a group $RO_1H$, a group $RO_2H$, a group AMP(OR)p or any monofunctional group such as alkyl, cycloalkyl, aryl, aralkyl, alkylaryl, alkyloxyalkyl, aryloxyalkyl or cycloalkoxyalkyl,
a is a number greater than 1, such as, for example, greater than 2.

The aminoplast residues bearing the groups OR thereof integrated into the polymers may be chosen, in a non-limiting manner, from structures (1) to (12) below:

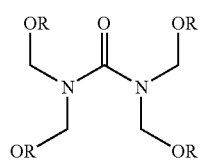

(1)

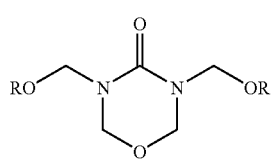

(2)

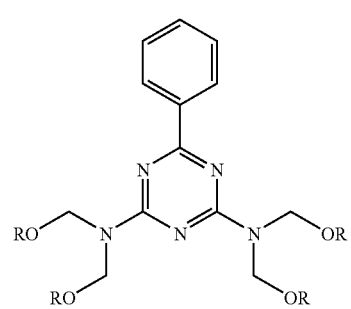

(3)

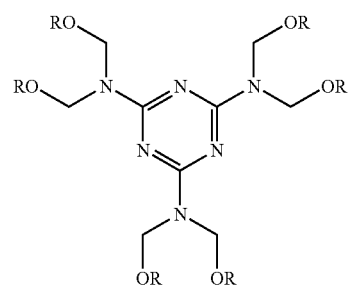

(4)

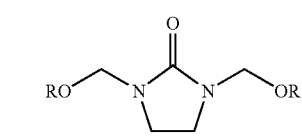

(5)

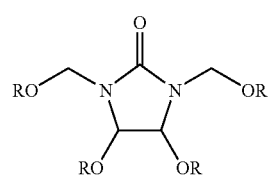

(6)

-continued

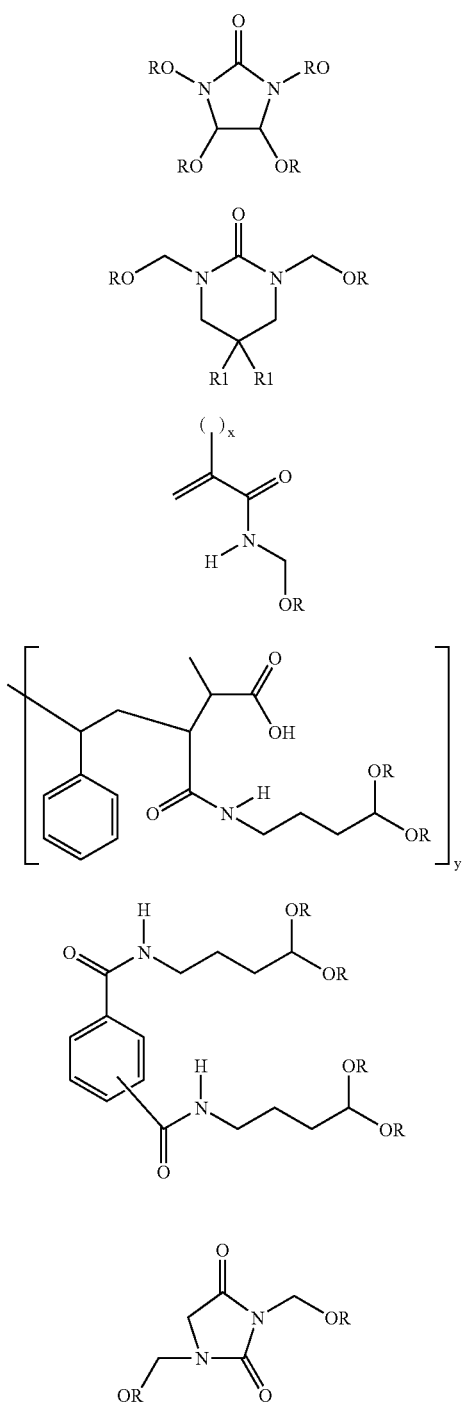

wherein:

R has the same meaning as above, $R_1$ is chosen from $C_1$-$C_4$ alkyl radicals, y is a number at least equal to 2, x is 0 or 1.

In at least one embodiment, the at least one aminoplast residue bearing the groups OR thereof is chosen from those of structure (13) below:

wherein R, p and x have the same meanings as above.

In at least one embodiment, the divalent alkyleneoxy residues are those corresponding to the diols of formula (14) below:

$$HO\text{-}(ZO)_{y'}\text{-}(Z_1(Z_2O)_w)_t\text{-}(Z'O)_{y'}\text{-}Z_3OH \tag{14},$$

y and y' are numbers ranging from 0 to 1000, t and w are numbers ranging from 0 to 10, Z, Z', $Z_2$ and $Z_3$ are chosen from $C_2$-$C_4$ alkylene radicals, such as, for example, radicals —$CH_2$—$CH(Z_4)$- and —$CH_2$—$CH(Z_4)$—$CH_2$—, $Z_1$ is chosen from linear and cyclic, branched and unbranched, aromatic and non-aromatic radicals optionally comprising at least one hetero atom and comprising from 1 to 40 carbon atoms, $Z_4$ is chosen from a hydrogen atoms, $C_1$-$C_4$ alkyl radicals and $C_1$-$C_3$ acyl radicals, it being understood that at least one of the radicals $Z_4$ of the radicals Z, Z', $Z_2$ and $Z_3$ is other than an acyl radical.

In at least one embodiment, $Z_4$ is chosen from a hydrogen atom and a methyl radical.

According to at least one embodiment, t=0 and Z, Z' and $Z_3$ are chosen from —$CH_2CH_2$—, and at least one of the groups from among y and y' is other than 0. The compounds of formula (14) are then polyethylene glycols.

The aminoplast-ether polymers of formula (g) are described, for example, in U.S. Pat. No. 5,914,373, to which reference may be made for further details.

As polymers with an aminoplast-ether skeleton of formula (g), non-limiting mention may be made of the products Pure-Thix® L (PEG-180/Octoxynol-40/TMMG Copolymer (INCI name)), Pure-Thix M® (PEG-180/Laureth-50/TMMG Copolymer (INCI name)) and Pure-Thix® HH (Polyether-1 (INCI name)); Pure-Thix TX-1442® (PEG-18/dodoxynol-5/PEG-25 tristyrylphenol/tetramethoxy methyl glycoluril copolymer), sold by the company Süd-Chemie.

The thickening polymers included as ingredient in the composition according to the present disclosure may also be chosen from associative polymers comprising at least one ethylenically unsaturated monomer containing a sulfonic group, in free or partially or totally neutralized form and comprising at least one hydrophobic portion.

In at least one embodiment, the polymers are partially or totally neutralized with a mineral base (sodium hydroxide, potassium hydroxide or aqueous ammonia) or an organic base such as monoethanolamine, diethanolamine, triethanolamine, an aminomethylpropanediol, N-methylglucamine and basic amino acids, for instance arginine and lysine, and mixtures of these compounds.

These associative polymers may or may not be crosslinked, and, in at least one embodiment, are crosslinked polymers. In this case, the crosslinking agents are derived from at least one monomer containing at least two ethylenic unsaturations (carbon-carbon double bond).

The crosslinking monomers containing at least two ethylenic unsaturations may be chosen, for example, from diallyl ether, triallyl cyanurate, diallyl maleate, allyl (meth)acrylate, dipropylene glycol diallyl ether, polyglycol diallyl ethers, triethylene glycol divinyl ether, hydroquinone diallyl ether, tetraallyloxyethane, diethylene glycol di(meth)-acrylate or tetraethylene glycol di(meth)acrylate, triallylamine, tetraallylethylenediamine, trimethylolpropane diallyl ether, trimethylolpropane triacrylate, methylenebis-(meth)acrylamide or divinylbenzene, allylic ethers of alcohols of the sugar series, or other allyl or vinyl ethers of polyfunctional alcohols, and also allylic esters of phosphoric and/or vinylphosphonic acid derivatives, or mixtures of these compounds.

In at least one embodiment, methylenebisacrylamide, allyl methacrylate or trimethylolpropane triacrylate is used. According to at least one embodiment, the degree of crosslinking ranges from 0.01 mol % to 10 mol % relative to the polymer.

In at least one embodiment, the ethylenically unsaturated monomers containing a sulfonic group are chosen from vinylsulfonic acid, styrenesulfonic acid, (meth)acrylamido($C_1$-$C_{22}$)alkylsulfonic acids, and N—($C_1$-$C_{22}$)alkyl(meth)acrylamido($C_1$-$C_{22}$)alkylsulfonic acids, for instance undecylacrylamidomethanesulfonic acid, and also partially or totally neutralized forms thereof.

(Meth)acrylamido($C_1$-$C_{22}$)alkylsulfonic acids such as, for example, acrylamidomethanesulfonic acid, acrylamidoethanesulfonic acid, acrylamidopropanesulfonic acid, 2-acrylamido-2-methylpropanesulfonic acid, methacrylamido-2-methylpropanesulfonic acid, 2-acrylamido-n-butanesulfonic acid, 2-acrylamido-2,4,4-trimethylpentanesulfonic acid, 2-methacrylamidododecylsulfonic acid or 2-acrylamido-2,6-dimethyl-3-heptanesulfonic acid, and also partially or totally neutralized forms thereof, may be used according to at least one embodiment.

In at least one embodiment, 2-acrylamido-2-methylpropanesulfonic acid (AMPS), and also partially or totally neutralized forms thereof, is used.

The amphiphilic polymers present in the composition according to at least one embodiment of the present disclosure may also be chosen from random amphiphilic AMPS polymers modified by reaction with a $C_6$-$C_{22}$ n-monoalkylamine or di-n-alkylamine, and such as those described in International Patent Application No. WO 00/31154.

In at least one embodiment, the hydrophobic monomers that constitute the hydrophobic portion of the polymer are chosen from the acrylates or acrylamides of formula (k) below:

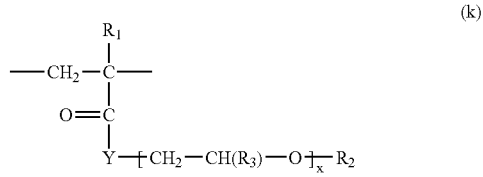

wherein $R_1$ and $R_3$, which may be identical or different, are chosen from hydrogen atoms and linear and branched $C_1$-$C_6$ alkyl radicals (for example, methyl); Y is chosen from O and NH; $R_2$ is chosen from hydrophobic hydrocarbon-based radicals as defined previously; x denotes a number of moles of alkylene oxide and ranges from 0 to 100.

The radical $R_2$, in at least one embodiment, is chosen from linear $C_6$-$C_{18}$ alkyl radicals (for example, n-hexyl, n-octyl, n-decyl, n-hexadecyl and n-dodecyl) and branched and cyclic $C_6$-$C_{18}$ alkyl radicals (for example, cyclododecane ($C_{12}$) or adamantane ($C_{10}$)); $C_6$-$C_{18}$ alkylperfluoro radicals (for example the group of formula —($CH_2$)$_2$—($CF_2$)$_9$—$CF_3$); the cholesteryl radical ($C_{27}$) or a cholesterol ester residue, for instance the cholesteryl oxyhexanoate group; aromatic polycyclic groups, for instance naphthalene or pyrene. In at least one embodiment, $R_2$ is chosen from linear alkyl radicals, such as, for example, the n-dodecyl radical.

According to at least one embodiment of the present disclosure, the monomer of formula (k) comprises at least one alkylene oxide unit (x≧1) and a polyoxyalkylenated chain. In at least one embodiment, the polyoxyalkylenated chain comprises ethylene oxide units and/or of propylene oxide units and, in a further embodiment, consists of ethylene oxide units. In at least one embodiment, the number of oxyalkylene units ranges from 3 to 100, such as, for example, from 3 to 50 or from 7 to 25.

The copolymers may also contain other ethylenically unsaturated hydrophilic monomers, chosen, for example, from (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

These copolymers are described, for example, in European Patent No. EP 750 899 and U.S. Pat. No. 5,089,578 and in the following publications from Yotaro Morishima:

"Self-assembling amphiphilic polyelectrolytes and their nanostructures—Chinese Journal of Polymer Science Vol. 18, No. 40, (2000), 323-336";

"Micelle formation of random copolymers of sodium 2-(acrylamido)-2-methylpropanesulfonate and a nonionic surfactant macromonomer in water as studied by fluorescence and dynamic light scattering—Macromolecules 2000, Vol. 33, No. 10-3694-3704";

"Solution properties of micelle networks formed by nonionic moieties covalently bound to a polyelectrolyte: salt effects on rheological behaviour—Langmuir, 2000, Vol. 16, No. 12, 5324-5332";

"Stimuli responsive amphiphilic copolymers of sodium 2-(acrylamido)-2-methylpropanesulfonate and associative macromonomers—Polym. Preprint, Div. Polym. Chem. 1999, 40(2), 220-221".

The distribution of the monomers in the copolymer may be in random or block form.

Among the polymers of this type, non-limiting mention may be made of:

crosslinked or non-crosslinked, neutralized or non-neutralized copolymers comprising from 15% to 60% by weight of AMPS units and from 40% to 85% by weight of ($C_8$-$C_{16}$)alkyl(meth)acrylamide units or of ($C_8$-$C_{16}$) alkyl(meth)acrylate units, relative to the polymer, such as those described in European Patent Application No. EP-A-750 899;

terpolymers comprising from 10 mol % to 90 mol % of acrylamide units, from 0.1 mol % to 10 mol % of AMPS units and from 5 mol % to 80 mol % of n-($C_6$-$C_{18}$) alkylacrylamide units, such as those described in U.S. Pat. No. 5,089,578;

copolymers of totally neutralized AMPS and of dodecyl methacrylate, and also crosslinked and non-crosslinked copolymers of AMPS and of n-dodecylmethacrylamide, such as those described in the Morishima articles mentioned above.

Non-limiting mention may also be made more of the copolymers consisting of AMPS units of formula (I) below:

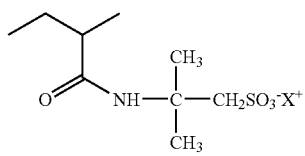 (I)

wherein X⁺ has the same definition as previously, and of units of formula (p) below:

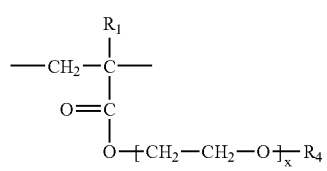 (p)

wherein x is an integer ranging from 3 to 100, such as, for example, from 5 to 80 or from 7 to 25; $R_1$ has the same meaning as that given above in formula (j) and $R_4$ is chosen from linear and branched $C_6$-$C_{22}$ alkyl radicals, such as, for example, $C_{10}$-$C_{22}$ alkyl radicals.

The polymers that are used according to at least one embodiment are those for which x=25, $R_1$ is methyl and $R_4$ is n-dodecyl; they are described in the Morishima articles mentioned above.

The polymers for which X⁺ is sodium or ammonium are used in at least one embodiment.

Polymers of the Genapol® range from the company Hoechst/Clariant may be used in the composition according to the present disclosure.

The concentration of associative or non-associative thickening polymer present in the composition according to at least one embodiment of the present disclosure may range from 0.01% to 10% by weight, such as, for example, from 0.1% to 5% or from 0.5% to 5% by weight, relative to the weight of the composition.

Needless to say, a person skilled in the art will take care to select this or these optional additional compound(s) such that the advantageous properties intrinsically associated with the composition in accordance with the present disclosure are not, or are not substantially, adversely affected by the envisaged addition(s).

The composition according to the disclosure may be in various forms, such as in the form of liquids, shampoos, creams or gels, or in any other suitable form.

One form that is used according to at least one embodiment of the present disclosure is a dyeing and/or lightening shampoo comprising, in a cosmetically acceptable aqueous medium, at least one direct dye as defined above, and at least one surfactant.

According to at least one embodiment, the composition of the present disclosure may contain at least one oxidizing agent chosen, for example, from hydrogen peroxide, urea peroxide, alkali metal bromates, persalts such as perborates and persulfates, and enzymes such as peroxidases and two-electron or four-electron oxidoreductases. Hydrogen peroxide or enzymes is used in at least one embodiment.

The present disclosure also relates to a process for treating keratin fibers, such as, for example, human keratin fibers.

According to at least one embodiment, a composition as defined is applied to wet or dry fibers, for a sufficient time, after which the fibers are rinsed, optionally washed with shampoo, rinsed again and dried, or the resulting fibers are left to dry. This process may be used for compositions of any type, whether or not they comprise an oxidizing agent and/or a direct dye and/or an oxidation base optionally combined with a coupler.

According to at least one embodiment of the process, a composition as defined is applied to wet or dry fibers without final rinsing. This process may be used, for example, with compositions not comprising an oxidation dye (oxidation base and optionally coupler) or an oxidizing agent.

In at least one embodiment of the process, the application time is usually sufficient to develop the desired coloration and/or lightening.

For example, the application time for the composition is from 5 to 60 minutes, such as from 15 to 60 minutes.

The temperature at which the process according to at least one embodiment of the present disclosure is performed ranges from room temperature (15 to 25° C.) to 200° C., such as, for example, from 15 to 60° C.

When the composition comprises an oxidizing agent, the process according to at least one embodiment of the present disclosure comprises a preliminary step that comprises separately storing, on the one hand, a composition comprising, in a cosmetically acceptable medium, at least one direct dye corresponding to formula (I), optionally at least one additional direct dye and/or optionally at least one oxidation base optionally combined with at least one coupler, and, on the other hand, a composition comprising, in a cosmetically acceptable medium, at least one oxidizing agent, and then in mixing them together at the time of use. Once this has been performed, the process according to the present disclosure is carried out in accordance with the indications mentioned previously.

The present disclosure also relates to a multi-compartment device, comprising at least one compartment containing a composition comprising at least one direct dye corresponding to formula (I), and at least one other compartment containing a composition comprising at least one oxidizing agent. This device may be equipped with a means for applying the desired mixture to the hair, such as the devices described in French Patent No. FR 2 586 913.

In embodiments where the composition contains at least one additional direct dye and/or at least one oxidation base optionally combined with at least one coupler, according to at least one embodiment, this or these compound(s) is (are) in the first compartment of the device previously described. According to at least one further embodiment, the additional direct dye and/or the oxidation base/coupler are stored in a third compartment.

It is pointed out that it would not be excluded to have a further embodiment combining the previous embodiments, in which the additional direct dye and/or the oxidation base and optionally the coupler would be partly in the first compartment, with the direct compound corresponding to formula (I), and partly in a third compartment.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding the numerical ranges and parameters setting forth the broad scope of the invention as approximations, the numerical values set forth in the specific examples are reported as precisely as possible. Any numerical value, however, inherently contains certain errors necessarily resulting from the standard deviation found in its respective testing measurement.

The examples that follow are intended to illustrate the disclosure without, however, limiting its scope.

Examples of Compositions According to the Present Disclosure:

Dye Composition

| Compound of the present disclosure | Amount |
|---|---|
| Methine direct dye of formula A, B, C, D or E | $10^{-3}$ mol % |
| Hydroxyethylcellulose sold by the company Aqualon under the name NATROSOL 250MR | 0.384% |
| Mixture of methyl, ethyl, propyl, butyl and isobutyl p-hydroxybenzoates sold by the company NIPA under the name NIPA Ester 82121 | 0.032% |
| (50/50 C8/C10)Alkyl polyglucoside sold by the company SEPPIC under the name ORAMIX CG110 | 5% |
| Benzyl alcohol | 4% |
| Propylene glycol (8 EO) | 6% |
| Demineralized water qs | 100 |

Compound (A) had the following structure:

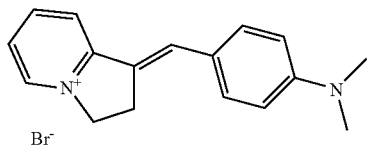

1-(4-Dimethylaminobenzylidene)-2,3-dihydro-1H-indolizinylium bromide

This dye composition was applied to natural hair containing 90% white hairs. The temperature and the action time were, respectively, 33° C. and 30 minutes.

After rinsing, shampooing and drying under a hood for 30 minutes, the hair had a very attractive orange-yellow coloration. The color obtained was shampoo-fast and the composition was stable on storage.

Compound (B) had the following structure:

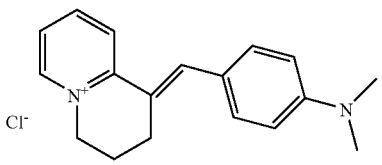

1-(4-Dimethylaminobenzylidene)-1,2,3,4-tetrahydroquinolizinylium chloride

This dye composition was applied to natural hair containing 90% white hairs. The temperature and the action time were, respectively, 33° C. and 30 minutes.

After rinsing, shampooing and drying under a hood for 30 minutes, the hair had a very attractive orange coloration. The color obtained was shampoo-fast. The composition was stable on storage.

Compound (C) had the following structure:

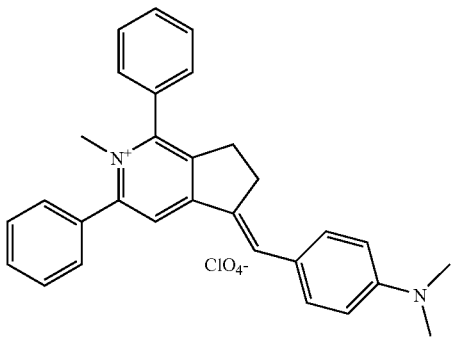

5-[[4-(Dimethylamino)phenyl]methylene]-6,7-dihydro-2-methyl-1,3-diphenyl-5H cyclopenta[c]pyridinium perchlorate The composition was applied to natural grey hair for 20 minutes at room temperature (25° C.). After dyeing, the locks were rinsed and dried.

The orange color obtained was shampoo-fast. The composition was stable on storage.

Compound (D) had the following structure:

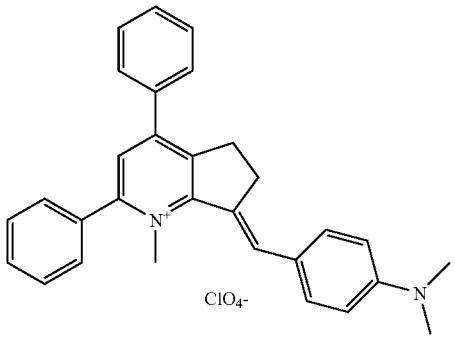

7-[[4-(Dimethylamino)phenyl]methylene]-6,7-dihydro-1-methyl-2,4-diphenyl-5H-cyclopenta[b]pyridinium perchlorate The composition was applied to natural grey hair containing 90% white hairs, for 20 minutes at room temperature. After dyeing, the locks were rinsed and dried.

The orange color obtained was shampoo-fast. The composition was stable on storage.

Compound (E) had the following structure:

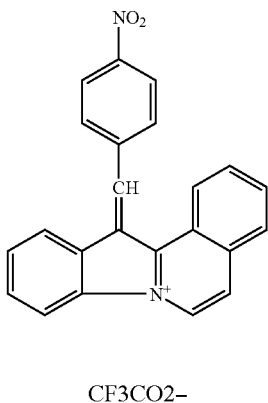

CF3CO2−

12-[(4-Nitrophenyl)methylene]-12H-indolo[2,1-a]isoquinolinium trifluoroacetate

The composition was applied to natural grey hair for 20 minutes at room temperature (25° C.). After dyeing, the locks were rinsed and dried.

The orange-yellow color obtained was shampoo-fast. The composition was stable on storage.

What is claimed is:

1. A process for dyeing and/or optically lightening keratin fibers, comprising:
applying to said keratin fibers a composition comprising at least one compound of formula (I):

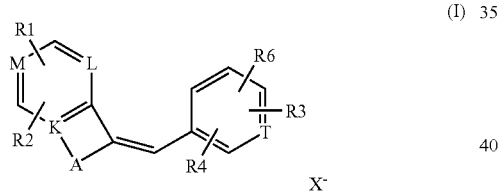

wherein:
M and L, independently of each other, are chosen from $CR_7$, $CR_9$ and $N^+R_5$;
K is chosen from a carbon atom and a quaternized nitrogen atom $N^+$;
T is chosen from groups $N^+R_5$, groups $CR_4$ and a nitrogen atom;
A is chosen from linear and branched alkylene groups $C_nH_{2n}$ comprising from 1 to 8 carbon atoms and optionally having at one end an oxygen atom or a carbonyl group; a group comprising at least one unsaturation, the unsaturation forming part of a benzene nucleus or of a heterocycle optionally substituted with at least one radical chosen from $C_1$-$C_4$ alkyl and $C_6$-$C_{30}$ aryl radicals;
$R_1$, $R_2$, $R_3$, $R_4$, $R_6$, $R_7$ and $R_9$, independently of each other, are chosen from hydrogen atoms; halogen atoms; $C_6$-$C_{30}$ aryl groups; hydroxyl groups; cyano groups; nitro groups; sulfo groups; amino groups; acylamino groups; di($C_1$-$C_6$)alkylamino groups; dihydroxy($C_1$-$C_6$)alkylamino groups; ($C_1$-$C_6$)alkylhydroxy($C_1$-$C_6$)alkylamino groups; ($C_1$-$C_6$)alkoxy groups; ($C_1$-$C_6$)alkoxycarbonyl groups; carboxy($C_1$-$C_6$)alkoxy groups; piperidinosulfonyl groups; pyrrolidino groups; ($C_1$-$C_6$)alkylhalo($C_1$-$C_6$)alkylamino groups; benzoyl($C_1$-$C_6$) alkyl groups; vinyl groups; formyl groups; $C_6$-$C_{30}$ aryl radicals optionally substituted with at least one group chosen from hydroxyl, linear, branched and cyclic $C_1$-$C_6$ alkoxy and linear, branched and cyclic alkyl groups comprising from 1 to 22 carbon atoms, itself being optionally substituted with at least one group chosen from hydroxyl, amino and $C_1$-$C_6$ alkoxy groups; linear, branched and cyclic alkyl radicals comprising from 1 to 22 carbon atoms, optionally substituted with at least one group chosen from hydroxyl, amino, linear, branched and cyclic $C_1$-$C_6$ alkoxy, optionally substituted aryl, carboxyl and sulfo groups and halogen atoms, this alkyl radical optionally being interrupted with a heteroatom;
wherein two of the substituents $R_1$, $R_2$, $R_7$ and $R_9$, when M and L, respectively, are $CR_7$ and $CR_9$, may form with the carbon atoms to which they are attached a ring chosen from aromatic or non-aromatic $C_6$-$C_{30}$ rings and from 5- to 30-membered heterocyclic rings comprising from 1 to 5 heteroatoms; these rings being optionally condensed, with the optional insertion of a carbonyl group, and being optionally substituted with at least one group chosen from $C_1$-$C_4$ alkyl, ($C_1$-$C_4$)alkoxy($C_1$-$C_4$)alkyl, amino, di($C_1$-$C_4$)alkylamino, halogen, phenyl, carboxyl and tri($C_1$-$C_4$)alkylammonio($C_1$-$C_4$)alkyl groups;
$R_1$, $R_2$, $R_7$, and $R_9$ may also be chosen from groups identical to the part of the molecule condensed on the pyridinium nucleus so as to form a perfectly symmetrical molecule, thus comprising an acridinium sequence;
two of the substituents $R_3$, $R_4$ and $R_6$ may form with the carbon atoms to which they are attached a ring chosen from a $C_6$-$C_{30}$ aromatic nucleus and a 5- to 30-membered heterocyclic nucleus comprising in total from 1 to 5 heteroatoms and being optionally condensed, wherein this ring may be optionally substituted with at least one group chosen from $C_1$-$C_4$ alkyl, ($C_1$-$C_4$)alkoxy($C_1$-$C_4$) alkyl, amino, di($C_1$-$C_4$)alkylamino, halogen, phenyl, carboxyl and tri($C_1$-$C_4$)alkylammonio($C_1$-$C_4$)alkyl groups and may optionally form with the optional substituent and the carbon atom bearing it a saturated or unsaturated, 5- to 10-membered ring;
$R_5$ is chosen from linear, branched and cyclic alkyl radicals comprising from 1 to 22 carbon atoms, optionally substituted with at least one group chosen from hydroxyl, linear, branched or cyclic $C_1$-$C_6$ alkoxy, optionally substituted aryl, carboxyl and sulfo groups and halogen atoms, this alkyl radical being optionally interrupted with a heteroatom; and $C_6$-$C_{30}$ aryl radicals optionally substituted with at least one $C_1$-$C_4$ alkyl, $C_1$-$C_4$ alkoxy or hydroxyl radical;
$R_5$ may form with the nitrogen atom bearing it and with one of the substituents $R_1$, $R_2$, $R_7$ and $R_9$ and the carbon atom bearing this substituent a 5- to 10-membered ring optionally substituted with an alkyl group; this ring may be optionally condensed with a benzene ring or with a ring formed by two of the remaining substituents and the carbon atoms bearing them;
$X^-$ is chosen from organic and mineral anions;
wherein only one from among K, L and M can be $N^+R_5$ or $N^+$.

2. The process according to claim 1, wherein
$R_1$, $R_2$, $R_3$, $R_4$, $R_6$, $R_7$, and $R_9$, independently of each other, are chosen from hydrogen atoms; $C_6$-$C_{30}$ aryl groups optionally substituted with a group chosen from $C_1$-$C_6$ alkyl, $C_1$-$C_6$ alkoxy and hydroxyl radicals; hydroxyl groups; nitro groups; vinyl groups; pyrrolidino groups; benzoyl($C_1$-$C_6$)alkyl groups; ($C_1$-$C_6$)alkylhalo($C_1$-$C_6$)

alkylamino groups; amino groups; di($C_1$-$C_6$)alkylamino groups; dihydroxy($C_1$-$C_6$)alkylamino groups; ($C_1$-$C_6$)alkylhydroxy($C_1$-$C_6$)alkylamino groups; $C_1$-$C_6$ alkoxy groups; formyl groups; linear, branched or cyclic alkyl radicals comprising from 1 to 6 carbon atoms, optionally substituted with at least one group chosen from hydroxyl and optionally substituted aryl groups;

$R_1$, $R_2$, $R_7$, and $R_9$ may form with the carbon atoms to which they are attached a ring chosen from aromatic or non-aromatic $C_6$-$C_{30}$ rings and from 5- to 30-membered heterocyclic rings comprising in total from 1 to 5 heteroatoms; these rings being optionally condensed, with optional insertion of a carbonyl group, and being optionally substituted with at least one group chosen from $C_1$-$C_4$ alkyl, ($C_1$-$C_4$)alkoxy($C_1$-$C_4$)alkyl, amino, di($C_1$-$C_4$)alkylamino and phenyl groups;

$R_1$, $R_2$, $R_7$, and $R_9$ may also be chosen from groups identical to the part of the molecule condensed on the pyridinium nucleus so as to form a perfectly symmetrical molecule, thus comprising an acridinium sequence;

$R_3$ and $R_4$ may form with the carbon atoms to which they are attached a ring chosen from a $C_6$-$C_{30}$ aromatic nucleus and a 5- to 30-membered heterocyclic nucleus comprising in total from 1 to 5 heteroatoms; wherein this ring may be optionally condensed and optionally substituted with at least one $C_1$-$C_4$ alkyl group and may also form with $R_6$ and the carbon atom bearing it a new saturated or unsaturated 5- to 10-membered ring;

$R_5$ is chosen from linear, branched and cyclic alkyl radicals comprising from 1 to 22 carbon atoms and $C_6$-$C_{30}$ aryl radicals optionally substituted with at least one $C_1$-$C_4$ alkyl, $C_1$-$C_4$ alkoxy or hydroxyl radicals;

$R_5$ may form with the nitrogen atom bearing it and with $R_1$ and the carbon atom bearing this substituent $R_1$ a 5- to 10-membered ring optionally substituted with an alkyl group; this ring may be optionally condensed with a benzene ring or with a ring formed by $R_1$ and $R_2$ and the carbon atoms bearing them.

3. The process according to claim 1, wherein the compounds of formula (I) are chosen from the compounds of formulae (II) to (V) below:

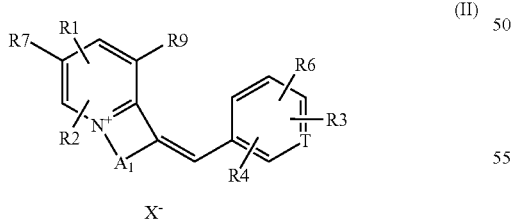

(II)

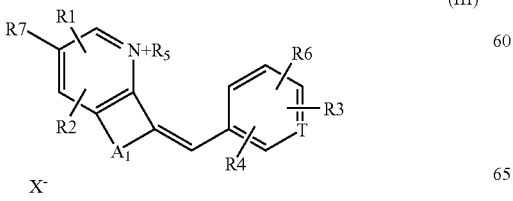

(III)

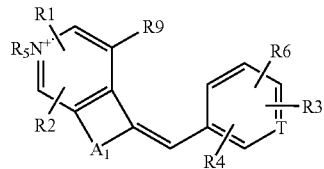

(IV)

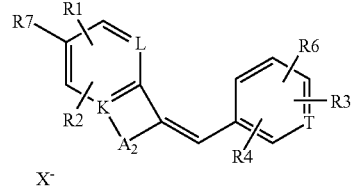

(V)

wherein:

$R_1$, $R_2$, $R_3$, $R_4$, $R_5$, $R_6$, $R_7$, $R_9$, K, L, X and T have the same meanings as defined above for formula (I) and wherein:

$A_1$ is chosen from linear and branched alkylene groups $C_nH_{2n}$ comprising from 1 to 8 carbon atoms and optionally having at one end an oxygen atom or a carbonyl group;

$A_2$ is chosen from groups comprising at least one unsaturation, the unsaturation forming part of a benzene nucleus or of a heterocycle optionally substituted with at least one $C_1$-$C_4$ alkyl or $C_6$-$C_{30}$ aryl radical;

wherein only one of the groups K and L can be $N^+$ or a group $N^+R_5$.

4. The process according to claim 3, wherein, in formula (II):

$A_1$ is chosen from linear and branched alkylene groups $C_nH_{2n}$ comprising from 1 to 8 carbon atoms and optionally having at one end a carbonyl group;

$R_1$, $R_2$, $R_3$, $R_4$, $R_6$, $R_7$, and $R_9$, independently of each other, are chosen from hydrogen atoms; $C_6$-$C_{30}$ aryl groups optionally substituted with a group chosen from $C_1$-$C_6$ alkyl, $C_1$-$C_6$ alkoxy and hydroxyl radicals; hydroxyl groups; vinyl groups; pyrrolidino groups; benzoyl($C_1$-$C_6$)alkyl groups; ($C_1$-$C_6$)alkylhalo($C_1$-$C_6$)alkylamino groups; amino groups; di($C_1$-$C_6$)alkylamino groups; dihydroxy($C_1$-$C_6$)alkylamino groups; ($C_1$-$C_6$)alkylhydroxy($C_1$-$C_6$)alkylamino groups; $C_1$-$C_6$ alkoxy groups; formyl groups; linear, branched or cyclic alkyl radicals comprising from 1 to 6 carbon atoms, optionally substituted with at least one group chosen from hydroxyl and optionally substituted aryl groups, $R_3$ and $R_4$ may form with the carbon atoms to which they are attached a ring chosen from a $C_6$-$C_{30}$ aromatic nucleus and a 5- to 30-membered heterocyclic nucleus comprising in total from 1 to 5 heteroatoms; wherein this ring may be optionally condensed and optionally substituted with at least one $C_1$-$C_4$ alkyl group and may also form with $R_6$ and the carbon atom bearing it a new saturated or unsaturated 5- to 10-membered ring.

5. The process according to claim 4, wherein $A_1$ is chosen from alkylene groups comprising from 2 to 4 carbon atoms, T is chosen from $CR_4$, $N^+R_5$, and N, $R_1$, $R_2$, $R_7$, and $R_9$ are hydrogen atoms, $R_3$ and $R_4$, independently of each other, are chosen from hydrogen atoms; $C_1$-$C_4$ alkyl radicals; $C_1$-$C_4$ alkoxy radicals; di($C_1$-$C_4$)alkylamino groups; dihydroxy($C_1$-

$C_4$)alkylamino groups; ($C_1$-$C_4$)alkylhydroxy($C_1$-$C_4$) alkylamino groups; pyrrolidino groups, formyl groups, or form, together with the carbon atoms bearing them, a 5- or 6-membered ring optionally comprising at least one heteroatom, this ring being optionally condensed, and the whole being optionally substituted with at least one $C_1$-$C_6$ alkyl radical, $R_6$ is a hydrogen atom or forms a ring including a ring member of a ring formed by $R_3$ and/or $R_4$.

6. The process according to claim 5, wherein $R_1$ and $R_2$, independently of each other are chosen from, methyl radicals, methoxy radicals, dimethylamino radicals, diethylamino radicals, dihydroxyethylamino radicals, and methylhydroxyethylamino radicals.

7. The process according to claim 3, wherein, in formula (III):

$A_1$ is chosen from linear and branched alkylene groups $C_nH_{2n}$ comprising from 1 to 8 carbon atoms and optionally having at one end a carbonyl group;

$R_1$, $R_2$, $R_3$, $R_4$, $R_6$, and $R_7$, independently of each other, are chosen from hydrogen atoms; $C_6$-$C_{30}$ aryl groups optionally substituted with a group chosen from $C_1$-$C_6$ alkyl, $C_1$-$C_6$ alkoxy and hydroxyl radicals; hydroxyl groups; vinyl groups; pyrrolidino groups; benzoyl($C_1$-$C_6$)alkyl groups; ($C_1$-$C_6$)alkylhalo($C_1$-$C_6$)alkylamino groups; amino groups; di($C_1$-$C_6$)alkylamino groups; dihydroxy($C_1$-$C_6$)alkylamino groups; ($C_1$-$C_6$)alkylhydroxy($C_1$-$C_6$)alkylamino groups; $C_1$-$C_6$ alkoxy groups; linear, branched or cyclic alkyl radicals comprising from 1 to 6 carbon atoms, optionally substituted with at least one group chosen from hydroxyl and optionally substituted aryl groups, $R_3$ and $R_4$ may form with the carbon atoms to which they are attached a ring chosen from a $C_6$-$C_{30}$ aromatic nucleus and a 5- to 30-membered heterocyclic nucleus comprising in total from 1 to 5 heteroatoms; wherein this ring may be optionally condensed and optionally substituted with at least one $C_1$-$C_4$ alkyl group and may also form with $R_6$ and the carbon atom bearing it a new saturated or unsaturated 5- to 10-membered ring;

$R_1$ and $R_7$ may also be chosen from groups identical to the part of the molecule condensed on the pyridinium nucleus so as to form a perfectly symmetrical molecule, thus comprising an acridinium sequence;

$R_5$ is chosen from linear, branched and cyclic alkyl radicals containing from 1 to 10 carbon atoms and $C_6$-$C_{30}$ aryl radicals optionally substituted with at least one $C_1$-$C_4$ alkyl, $C_1$-$C_4$ alkoxy or hydroxyl radical;

$R_5$ may form with the nitrogen atom bearing it and with $R_1$ and the carbon atom bearing this substituent $R_1$ a 5- to 10-membered ring optionally substituted with an alkyl group; this ring may be optionally condensed with a benzene ring or with a ring formed by $R_1$ and $R_2$ and the carbon atoms bearing them.

8. The process according to claim 7, wherein:

$A_1$ is chosen from alkylene groups comprising from 2 to 5 carbon atoms, and optionally having at one end a carbonyl group, and optionally substituted with at least one $C_1$-$C_6$ alkyl group;

T is $CR_4$;

$R_1$, $R_2$, and $R_7$, independently of each other, are chosen from hydrogen atoms and phenyl radicals or form, together with the carbon atoms bearing them, a $C_6$-$C_{12}$ aromatic ring or a saturated ring optionally inserting a carbonyl group into its ring members, these rings being optionally substituted with $C_1$-$C_4$ alkyl groups;

$R_5$ is chosen from $C_1$-$C_4$ alkyl radicals and $C_6$-$C_{12}$ aryl radicals optionally substituted with a $C_1$-$C_4$ alkyl, hydroxyl or $C_1$-$C_4$ alkoxy radical; or forms a ring including a ring member of a ring derived from $R_1$, $R_2$, and/or $R_7$ and from the atoms bearing them;

$R_3$ and $R_6$ are hydrogen atoms;

$R_4$ is chosen from a hydrogen atom, di($C_1$-$C_4$)alkylamino groups and ($C_1$-$C_4$)alkylhalo($C_1$-$C_4$)alkylamino groups.

9. The process according to claim 8, wherein:

$R_4$ is chosen from dimethylamino and ethylchloroethylamino groups; and $R_5$ is chosen from methyl and ethyl radicals.

10. The process according to claim 3, wherein, in formula (IV):

$A_1$ is chosen from linear and branched alkylene groups $C_nH_{2n}$ comprising from 1 to 8 carbon atoms and optionally having at one end a carbonyl group;

$R_1$, $R_2$, $R_3$, $R_4$, $R_6$, and $R_9$, independently of each other, are chosen from hydrogen atoms; $C_6$-$C_{30}$ aryl groups optionally substituted with a group chosen from $C_1$-$C_6$ alkyl, $C_1$-$C_6$ alkoxy and hydroxyl radicals; hydroxyl groups; vinyl groups; pyrrolidino groups; benzoyl($C_1$-$C_6$)alkyl groups; ($C_1$-$C_6$)alkylhalo($C_1$-$C_6$)alkylamino groups; amino groups; di($C_1$-$C_6$)alkylamino groups; dihydroxy($C_1$-$C_6$)alkylamino groups; ($C_1$-$C_6$)alkylhydroxy($C_1$-$C_6$)alkylamino groups; $C_1$-$C_6$ alkoxy groups; linear, branched and cyclic alkyl radicals comprising from 1 to 6 carbon atoms, optionally substituted with at least one group chosen from hydroxyl and optionally substituted aryl groups, $R_3$ and $R_4$ may form with the carbon atoms to which they are attached a ring chosen from a $C_6$-$C_{30}$ aromatic nucleus and a 5- to 30-membered heterocyclic nucleus comprising in total from 1 to 5 heteroatoms; wherein this ring may be optionally condensed and optionally substituted with at least one $C_1$-$C_4$ alkyl group and may also form with $R_6$ and the carbon atom bearing it a new saturated or unsaturated 5- to 10-membered ring;

$R_5$ is chosen from linear, branched and cyclic alkyl radicals containing from 1 to 22 carbon atoms and $C_6$-$C_{30}$ aryl radicals optionally substituted with at least one $C_1$-$C_4$ alkyl, $C_1$-$C_4$ alkoxy or hydroxyl radical;

$R_5$ may form with the nitrogen atom bearing it and with $R_1$ and the carbon atom bearing this substituent $R_1$ a 5- to 10-membered ring optionally substituted with an alkyl group; this ring may be optionally condensed with a benzene ring or with a ring formed by $R_1$ and $R_2$ and the carbon atoms bearing them.

11. The process according to claim 10, wherein:

$A_1$ is chosen from linear and branched alkylene groups $C_nH_{2n}$ comprising from 1 to 4 carbon atoms;

T is $CR_4$;

$R_2$, $R_3$, and $R_6$ are hydrogen atoms;

$R_1$ and $R_9$, independently of each other, are chosen from hydrogen atoms and $C_6$-$C_{12}$ aryl radicals, or form, together with the carbon atoms bearing them, an optionally condensed $C_6$-$C_{12}$ aromatic ring, all these rings optionally being substituted;

$R_4$ is chosen from a hydrogen atom, di($C_1$-$C_6$)alkylamino groups, dihydroxy($C_1$-$C_6$)alkylamino groups and ($C_1$-$C_6$)alkylhydroxy($C_1$-$C_6$)alkylamino groups;

$R_5$ is chosen from $C_1$-$C_{22}$ alkyl, phenyl and benzyl groups, or forms with $R_1$, $R_2$, and/or $R_9$ and the atoms bearing them two fused rings.

12. The process according to claim 11, wherein $R_4$ is chosen from dimethylamino, diethylamino and dihexylamino groups.

13. The process according to claim 3, wherein, in formula (V):
- $A_2$ is chosen from groups comprising at least one unsaturation, the unsaturation forming part of a benzene nucleus or of a heterocycle optionally substituted with at least one $C_1$-$C_4$ alkyl or $C_6$-$C_{30}$ aryl radical;
- $R_1$, $R_2$, $R_3$, $R_4$, $R_6$, and $R_7$, independently of each other, are chosen from hydrogen atoms; $C_6$-$C_{30}$ aryl groups optionally substituted with a group chosen from $C_1$-$C_6$ alkyl, $C_1$-$C_6$ alkoxy and hydroxyl radicals; hydroxyl groups; vinyl groups; pyrrolidino groups; benzoyl($C_1$-$C_6$)alkyl groups; ($C_1$-$C_6$)alkylhalo($C_1$-$C_6$)alkylamino groups; amino groups; di($C_1$-$C_6$)alkylamino groups; dihydroxy($C_1$-$C_6$)alkylamino groups; ($C_1$-$C_6$)alkylhydroxy($C_1$-$C_6$)alkylamino groups; $C_1$-$C_6$ alkoxy groups; formyl groups; linear, branched or cyclic alkyl radicals comprising from 1 to 6 carbon atoms, optionally substituted with at least one group chosen from hydroxyl and optionally substituted aryl groups,
- $R_3$ and $R_4$ may form with the carbon atoms to which they are attached a ring chosen from a $C_6$-$C_{30}$ aromatic nucleus and a 5- to 30-membered heterocyclic nucleus comprising in total from 1 to 5 heteroatoms; wherein this ring may be optionally condensed and optionally substituted with at least one $C_1$-$C_4$ alkyl group and may also form with $R_6$ and the carbon atom bearing it a new saturated or unsaturated 5- to 10-membered ring.

14. The process according to claim 13, wherein:
- $R_1$, $R_2$ and $R_7$, independently of each other, are chosen from hydrogen atoms and $C_1$-$C_4$ alkyl and vinyl radicals, or form, together with the carbon atoms bearing them, a saturated or unsaturated ring optionally bearing at least one alkyl radical,
- $R_6$ is a hydrogen atom,
- $R_3$ and $R_4$, independently of each other, are chosen from hydrogen atoms; $C_1$-$C_4$ alkyl groups; dialkylamino groups; $C_1$-$C_4$ alkoxy groups; hydroxyl radicals; nitro groups; $C_1$-$C_4$ benzoylalkyl radicals; or together form a 5- or 6-membered ring with the carbon atoms bearing them;
- with the proviso that if L is $N^+R_5$, then $R_5$ is chosen from $C_1$-$C_4$ alkyl radicals and benzoyl($C_1$-$C_4$)alkyl radicals, and if K is $N^+$, then $R_9$ is a hydrogen atom.

15. The process according to claim 14, wherein $R_3$ and $R_4$, independently of each other, are chosen from methyl, dimethylamino, methoxy, and ethoxy radicals.

16. The process according to claim 13, wherein
- $A_2$ is chosen from —C($R_{10}$)=C($R_{11}$)—, —N=CH—NH— and a pyrazolyl radical,
- $R_{10}$ and $R_{11}$, independently of each other, are chosen from $C_1$-$C_4$ alkyl radicals and phenyl radicals, or together form a benzene nucleus,
- $R_{12}$ and $R_{13}$ are chosen from $C_1$-$C_4$ alkyl radicals and phenyl radicals.

17. The process according to claim 1, wherein the anion of mineral origin is chosen from halides, sulfates, bisulfates, nitrates, phosphates, hydrogen phosphates, dihydrogen phosphates, boronates, carbonates and bicarbonates; and the anion of organic origin is chosen from those originating from salts of saturated or unsaturated, aromatic or non-aromatic monocarboxylic or polycarboxylic, sulfonic or sulfuric acids, optionally substituted with at least one hydroxyl or amino radical or halogen atoms.

18. The process according to claim 17, wherein the anion is chosen from chloride, iodide, sulfate, methosulfate and ethosulfate.

19. The process according to claim 1, wherein the at least one compound is chosen from:
- 4-[[4-(Dimethylamino)phenyl]methylene]-1,2,3,4-tetrahydrobenzo[c]quinolizinium perchlorate;
- 1-(4-Dimethylaminobenzylidene)-1,2,3,4-tetrahydroquinolizinylium chloride;
- 1-(2,3,6,7-Tetrahydro-1H,5H-pyrido[3,2,1-ij]quinolin-9-ylmethylene)-1,2,3,4-tetrahydroquinolizinylium chloride;
- 1-(4-Dimethylaminobenzylidene)-2,3-dihydro-1H-indolizinylium bromide;
- 1-(2,3,6,7-Tetrahydro-1H,5H-pyrido[3,2,1-ij]quinolin-9-ylmethylene)-2,3-dihydro-1H-indolizinylium bromide;
- 1-(1-Methyl-1,2,3,4-tetrahydroquinolin-6-ylmethylene)-2,3-dihydro-1H-indolizinylium bromide;
- 1-(1-Ethyl-2,3-dihydro-1H-indol-5-ylmethylene)-2,3-dihydro-1H-indolizinylium bromide;
- 1-(4-Pyrrolidin-1-ylbenzylidene)-2,3-dihydro-1H-indolizinylium dibromide;
- 1-(4-Dimethylaminonaphthalen-1-ylmethylene)-2,3-dihydro-1H-indolizinylium bromide;
- 1-(9-Ethyl-9H-carbazol-3-ylmethylene)-2,3-dihydro-1H-indolizinylium bromide;
- 1-(4-Methyl-3,4-dihydro-2H-benzo[1,4]oxazin-7-ylmethylene)-2,3-dihydro-1H-indolizinylium bromide;
- 1-Pyridin-4-ylmethylene-2,3-dihydro-1H-indolizinylium bromide;
- 1-(4-Dimethylamino-2-methoxy-benzylidene)-2,3-dihydro-1H-indolizinylium bromide;
- 1-Naphthalen-2-ylmethylene-2,3-dihydro-1H-indoliziny-lium bromide;
- 1-(1-Isopropyl-1,2,3,4-tetrahydroquinolin-6-ylmethylene)-2,3-dihydro-1H-indolizinylium bromide;
- 1-Naphthalen-1-ylmethylene-2,3-dihydro-1H-indoliziny-lium bromide;
- 1-{4-[Ethyl-(2-hydroxyethyl)amino]-2-methylbenzylidene}-2,3-dihydro-1H-indolizinylium bromide;
- 1-(4-Formylbenzylidene)-2,3-dihydro-1H-indolizinylium bromide;
- 1-{4-[Bis(2-hydroxyethyl)amino]benzylidene}-2,3-dihydro-1H-indolizinylium bromide;
- 1-(1,1,7,7-Tetramethyl-2,3,6,7-tetrahydro-1H,5H-pyrido[3,2,1-ij]quinolin-9-ylmethylene)-2,3-dihydro-1H-indolizinylium bromide;
- 1-(9H-Fluoren-2-ylmethylene)-2,3-dihydro-1H-indolizinylium bromide;
- 1-(4-Dimethylamino-2-methylbenzylidene)-2,3-dihydro-1H-indolizinylium bromide;
- 1-(2,2-Dimethylchroman-6-ylmethylene)-2,3-dihydro-1H-indolizinylium bromide;
- 1-Methylpyridinium-4-ylmethylene-2,3-dihydro-1H-indolizinylium bromide;
- 1-(1-Isobutyl-2,2-dimethyl-2,3-dihydro-1H-indol-5-ylmethylene)-2,3-dihydro-1H-indolizinylium bromide;
- 1-Pyren-1-ylmethylene-2,3-dihydro-1H-indolizinylium bromide;
- 1-(4-Diethylaminobenzylidene)-2,3-dihydro-1H-indolizinylium bromide;
- 1-Quinolin-4-ylmethylene-2,3-dihydro-1H-indoliziny-lium bromide;
- 4,5-Bis[[4-(dimethylamino)phenyl]methylene]-1,2,3,4,5,6,7,8-octahydro-3,3,6,6--tetramethyl -1,8-dioxo-10-phenylacridinium chloride;
- 7-[[4-(Dimethylamino)phenyl]methylene]-6,7-dihydro-1-methyl-2,4-diphenyl-5H-cyclopenta[b]pyridinium salt;
- 3-Benzylidene-2,3-dihydro-4-methyl-1H-cyclopenta[b]quinolinium methyl sulfate;

5,6,7,8,9,10-Hexahydro-1-methyl-10-(phenylmethylene)cycloocta[b]pyridinium iodide;

11-[[4-(Dimethylamino)phenyl]methylene]-2,3,8,9,10,11-hexahydro-10,10-dimethyl-8-oxo-1H-pyrido[3,2,1-de]acridinium perchlorate;

4-[[4-(Dimethylamino)phenyl]methylene]-1,2,3,4-tetrahydro-3,3,10-trimethyl-1-oxoacridinium perchlorate;

2,3,4,7-Tetrahydro-7,7-dimethyl-5-phenyl-1-(phenylmethylene)-1H-indolo[1,2-a]quinolinium perchlorate 4-[[4-(Dimethylamino)phenyl]methylene]-1,2,3,4,5,6,7,8-octahydro-3,3,6,6-tetramethyl-1,8-dioxo-10-phenylacridinium chloride;

4-[[4-[(2-Chloroethyl)ethylamino]phenyl]methylene]-1,2,3,4-tetrahydro-9,10-dimethylacridinium iodide 4-[[4-(Dimethylamino)phenyl]methylene]-1,2,3,4-tetrahydro-3,3-dimethyl-5-(4-methylphenyl)-1-oxobenz[b]acridinium bromide;

4-[[4-(Dimethylamino)phenyl]methylene]-1,2,3,4-tetrahydro-1-oxo-5-phenylbenz[b]acridinium bromide;

4-[[4-(Dimethylamino)phenyl]methylene]-1,2,3,4-tetrahydro-10-(4-hydroxyphenyl)-3,3-dimethyl-1-oxoacridinium perchlorate;

4-[[4-(Dimethylamino)phenyl]methylene]-1,2,3,4-tetrahydro-3,3-dimethyl-1-oxo-10-phenylacridinium perchlorate;

4-[[4-(Dimethylamino)phenyl]methylene]-10-ethyl-1,2,3,4-tetrahydro-3,3-dimethyl-1-oxoacridinium perchlorate;

3-[p-(Dimethylamino)benzylidene]-2,3-dihydro-4,9-dimethyl-1H-cyclopenta[b]quinolinium iodide;

4-[[4-(Dimethylamino)phenyl]methylene]-1,2,3,4,5,6,7,8-octahydro-3,3,6,6-tetramethyl-10-(4-methylphenyl)-1,8-dioxoacridinium chloride;

4-[[4-(Dimethylamino)phenyl]methylene]-1,2,3,4,5,6,7,8-octahydro-3,3,6,6-tetramethyl-10-(1-naphthalenyl)-1,8-dioxoacridinium chloride;

4-[[4-(Dimethylamino)phenyl]methylene]-1,2,3,4-tetrahydro-5-(4-methoxyphenyl)-3,3-dimethyl-1-oxobenz[b]acridinium bromide;

4-[[4-(Dimethylamino)phenyl]methylene]-1,2,3,4-tetrahydro-1-oxo-10-phenylacridinium perchlorate;

4-[[4-(Dimethylamino)phenyl]methylene]-1,2,3,4-tetrahydro-3,3-dimethyl-1-oxo-5-phenylbenz[b]acridinium bromide;

4-[p-(Dimethylamino)benzylidene]-1,2,3,4-tetrahydro-9,10-dimethylacridinium iodide (5E)-5-[[4-(Dibutylamino)phenyl]methylene]-5,6,7,8-tetrahydro-2-octadecylisoquinolinium salt;

(5E)-5-[[4-(Diethylamino)phenyl]methylene]-5,6,7,8-tetrahydro-2-octadecylisoquinolinium salt;

(5E)-5-[[4-(dimethylamino)phenyl]methylene]-5,6,7,8-tetrahydro-2-octadecylisoquinolinium sulfate;

12-[[4-(Dimethylamino)phenyl]methylene]-5,6,9,10,11,12-hexahydro-4H-pyrido[3,2,1-de]phenanthridinium perchlorate;

10-[[4-(Dimethylamino)phenyl]methylene]-7,8,9,10-tetrahydro-5-(phenylmethyl)benzo[c]phenanthridinium perchlorate;

1-[[4-(Dimethylamino)phenyl]methylene]-1,2,3,4-tetrahydro-6-phenylbenzo[a]phenanthridinium perchlorate;

10-[[4-(Dimethylamino)phenyl]methylene]-7,8,9,10-tetrahydro-5-(phenylmethyl)phenanthridinium perchlorate;

10-[[4-(Dimethylamino)phenyl]methylene]-7,8,9,10-tetrahydro-5-methylphenanthridinium perchlorate;

5-[[4-(Dimethylamino)phenyl]methylene]-6,7-dihydro-2-methyl-1,3-diphenyl-5H-cyclopenta[c]pyridinium salt;

(5E)-5-[[4-(Dihexylamino)phenyl]methylene]-5,6,7,8-tetrahydro-2-octadecylisoquinolinium salt;

10-[[4-(Dimethylamino)phenyl]methylene]-7,8,9,10-tetrahydro-5-phenylphenanthridinium perchlorate;

10-[[4-(Dimethylamino)phenyl]methylene]-7,8,9,10-tetrahydro-5-phenylbenzo[c]phenanthridinium perchlorate;

10-[[4-(Dimethylamino)phenyl]methylene]-5-ethyl-7,8,9,10-tetrahydrophenanthridinium perchlorate;

12-[(4-Nitrophenyl)methylene]-12H-indolo[2,1-a]isoquinolinium trifluoroacetate;

12-[(4-Methoxyphenyl)methylene]-12H-indolo[2,1-a]isoquinolinium trifluoroacetate;

12-[(1,3-Benzodioxol-5-ylmethylene]-12H-indolo[2,1-a]isoquinolinium trifluoroacetate;

12-[(3,4-Dimethoxyphenyl)methylene]-12H-indolo[2,1-a]isoquinolinium trifluoroacetate;

12-[(2-Hydroxyphenyl)methylene]-12H-indolo[2,1-a]isoquinolinium trifluoroacetate;

1-(p-Dimethylaminobenzylidene)-2,3-dimethyl-1H-indolizinium nitrate;

1-[[4-(Dimethylamino)phenyl]methylene]-6-ethyl-2,3-dimethyl-1H-indolizinium perchlorate;

1-(3-Ethoxy-4-hydroxybenzylidene)-6-ethyl-2,3-dimethyl-1H-indolizinium chloride;

inner salt of 3-(3-ethoxy-4-hydroxybenzylidene)-6-ethyl-1,2-dimethyl-3H-indolizinium hydroxide;

4-Methyl-3-[(4-nitrophenyl)methylene]-1,2-diphenyl-3H-cyclopenta[b]quinolinium perchlorate;

5-[[1-(2-Oxo-2-phenylethyl)pyridinium-4-yl]methylene]-5H-indeno [1,2-b]pyridinium bis(2-oxo-2-phenylethylide), 12-(Phenylmethylene)-12H-indolo[2,1-a]isoquinolinium trifluoroacetate;

9-(1,3-Benzodioxol-5-ylmethylene)-3,9-dihydro-2,3,7-trimethyl-8-phenylimidazo[4,5-g]indolizin-6-ium salt;

12-[(3-Hydroxy-4-methoxyphenyl)methylene]-12H-indolo[2,1-a]isoquinolinium trifluoroacetate;

1,4-Dihydro-4-(phenylmethylene)[1,2,4]triazino[1,6-b]isoquinolin-11-ium perchlorate;

1-[[4-(Dimethylamino)phenyl]methylene]-2,3-dihydro-2-oxo-3,5,7-triphenyl-1H-indolizinium chloride;

7,8-Dihydro-10-methyl-8-phenyl-7-(phenylmethylene)-pyrazolo-[3',4':4,5]pyrrolo[1,2-a]quinolin-11-ium iodide;

1-[p-(Dimethylamino)benzylidene]-2,3-dimethyl-6-vinyl-1H-indolizinium chloride;

1,9-Dihydro-3-methyl-1-phenyl-9-(phenylmethylene)-pyrazolo[3,4-b]indolizin-4-ium iodide;

4-Methyl-1,2-diphenyl-3-(phenylmethylene)-cyclopenta[b]quinolinium perchlorate;

1,9-Dihydro-9-[(4-hydroxyphenyl)methylene]-3-methyl-1-phenylpyrazolo[3,4-b]indolizin-4-ium iodide;

9-[[4-(Dimethylamino)phenyl]methylene]-3,9-dihydro-2,3,7-trimethyl-8-phenylimidazo[4,5-g]indolizin-6-ium iodide;

9-[(2,5-dimethoxyphenyl)methylene]-3,9-dihydro-2,3,7-trimethyl-8-phenylimidazo[4,5-g]indolizin-6-ium iodide;

1,9-Dihydro-3-methyl-9-[(4-nitrophenyl)methylene]-1-phenyl-pyrazolo[3,4-b]indolizin-4-ium iodide.

20. The process according to claim 1, wherein said keratin fibers are human keratin fibers.

21. The process according to claim 20, wherein said composition is applied to wet or dry human keratin fibers for a time sufficient to develop a desired coloration, after which the fibers are rinsed, optionally washed with shampoo, rinsed again and dried, or the resulting fibers are left to dry.

22. The process according to claim 20, wherein said composition is applied to wet or dry human keratin fibers without final rinsing.

23. A composition comprising:
a cosmetically acceptable medium suitable for dyeing keratin fibers; and
in said medium, at least one direct dye of formula (I):

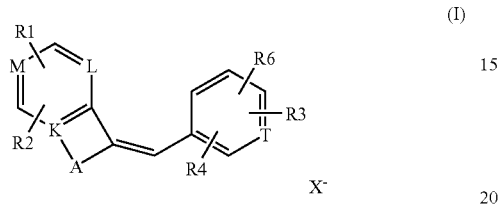

(I)

wherein:
M and L, independently of each other, are chosen from $CR_7$, $CR_9$ and $N^+R_5$;
K is chosen from a carbon atom and a quaternized nitrogen atom $N^+$;
T is chosen from groups $N^+R_5$, groups $CR_4$ and a nitrogen atom;
A is chosen from linear and branched alkylene groups $C_nH_{2n}$ comprising from 1 to 8 carbon atoms and optionally having at one end an oxygen atom or a carbonyl group; a group comprising at least one unsaturation, the unsaturation forming part of a benzene nucleus or of a heterocycle optionally substituted with at least one radical chosen from $C_1$-$C_4$ alkyl and $C_6$-$C_{30}$ aryl radicals;
$R_1$, $R_2$, $R_3$, $R_4$, $R_6$, $R_7$ and $R_9$, independently of each other, are chosen from hydrogen atoms; halogen atoms; $C_6$-$C_{30}$ aryl groups; hydroxyl groups; cyano groups; nitro groups; sulfo groups; amino groups; acylamino groups; di($C_1$-$C_6$)alkylamino groups; dihydroxy($C_1$-$C_6$)alkylamino groups; ($C_1$-$C_6$)alkylhydroxy($C_1$-$C_6$) alkylamino groups; ($C_1$-$C_6$)alkoxy groups; ($C_1$-$C_6$) alkoxycarbonyl groups; carboxy($C_1$-$C_6$)alkoxy groups; piperidinosulfonyl groups; pyrrolidino groups; ($C_1$-$C_6$) alkylhalo($C_1$-$C_6$)alkylamino groups; benzoyl($C_1$-$C_6$) alkyl groups; vinyl groups; formyl groups; $C_6$-$C_{30}$ aryl radicals optionally substituted with at least one group chosen from hydroxyl, linear, branched and cyclic $C_1$-$C_6$ alkoxy and linear, branched and cyclic alkyl groups comprising from 1 to 22 carbon atoms, itself being optionally substituted with at least one hydroxyl, amino or $C_1$-$C_6$ alkoxy group; linear, branched and cyclic alkyl radicals comprising from 1 to 22 carbon atoms, optionally substituted with at least one group chosen from hydroxyl, amino, linear, branched and cyclic $C_1$-$C_6$ alkoxy, optionally substituted aryl, carboxyl and sulfo groups and halogen atoms, this alkyl radical optionally being interrupted with a heteroatom;
wherein two of the substituents $R_1$, $R_2$, $R_7$ and $R_9$, when M and L, respectively, are $CR_7$ and $CR_9$, may form with the carbon atoms to which they are attached a ring chosen from aromatic or non-aromatic $C_6$-$C_{30}$ rings and 5- to 30-membered heterocyclic rings comprising from 1 to 5 heteroatoms; these rings being optionally condensed, with optional insertion of a carbonyl group, and being optionally substituted with at least one group chosen from $C_1$-$C_4$ alkyl, ($C_1$-$C_4$)alkoxy($C_1$-$C_4$)alkyl, amino, di($C_1$-$C_4$)alkylamino, halogen, phenyl, carboxyl and tri ($C_1$-$C_4$)alkylammonio($C_1$-$C_4$)alkyl groups;

$R_1$, $R_2$, $R_7$, and $R_9$ may also be chosen from groups identical to the part of the molecule condensed on the pyridinium nucleus so as to form a perfectly symmetrical molecule, thus comprising an acridinium sequence;

two of the substituents $R_3$, $R_4$ and $R_6$ may form with the carbon atoms to which they are attached a ring chosen from a $C_6$-$C_{30}$ aromatic nucleus and a 5- to 30-membered heterocyclic nucleus comprising in total from 1 to 5 heteroatoms; wherein this ring is optionally condensed and is optionally substituted with at least one group chosen from $C_1$-$C_4$ alkyl, ($C_1$-$C_4$)alkoxy($C_1$-$C_4$)alkyl, amino, di($C_1$-$C_4$)alkylamino, halogen, phenyl, carboxyl and tri($C_1$-$C_4$)alkylammonio($C_1$-$C_4$)alkyl groups and optionally forms with the optional substituent and the carbon atom bearing it a saturated or unsaturated, 5- to 10-membered ring;

$R_5$ is chosen from linear, branched and cyclic alkyl radicals comprising from 1 to 22 carbon atoms, optionally substituted with at least one group chosen from hydroxyl, linear, branched or cyclic $C_1$-$C_6$ alkoxy, optionally substituted aryl, carboxyl and sulfo groups and halogen atoms, this alkyl radical being optionally interrupted with a heteroatom; and $C_6$-$C_{30}$ aryl radicals optionally substituted with at least one $C_1$-$C_4$ alkyl, $C_1$-$C_4$ alkoxy or hydroxyl radical;

$R_5$ may form with the nitrogen atom bearing it and with one of the substituents $R_1$, $R_2$, $R_7$ and $R_9$ and the carbon atom bearing this substituent a 5- to 10-membered ring optionally substituted with an alkyl group; this ring may be optionally condensed with a benzene ring or with a ring formed by two of the remaining substituents and the carbon atoms bearing them;

$X^-$ is chosen from organic and mineral anions;

wherein only one from among K, L and M can be $N^+R_5$ or $N^+$, with the exception of the following compounds:

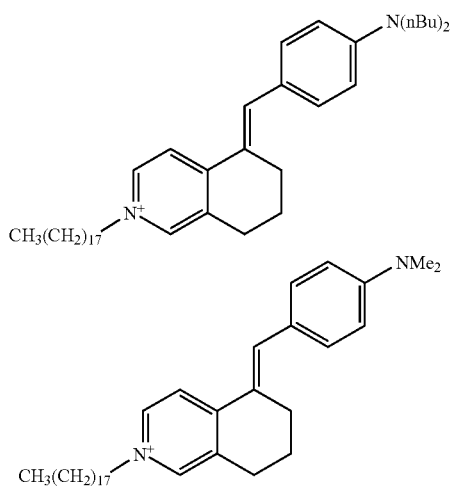

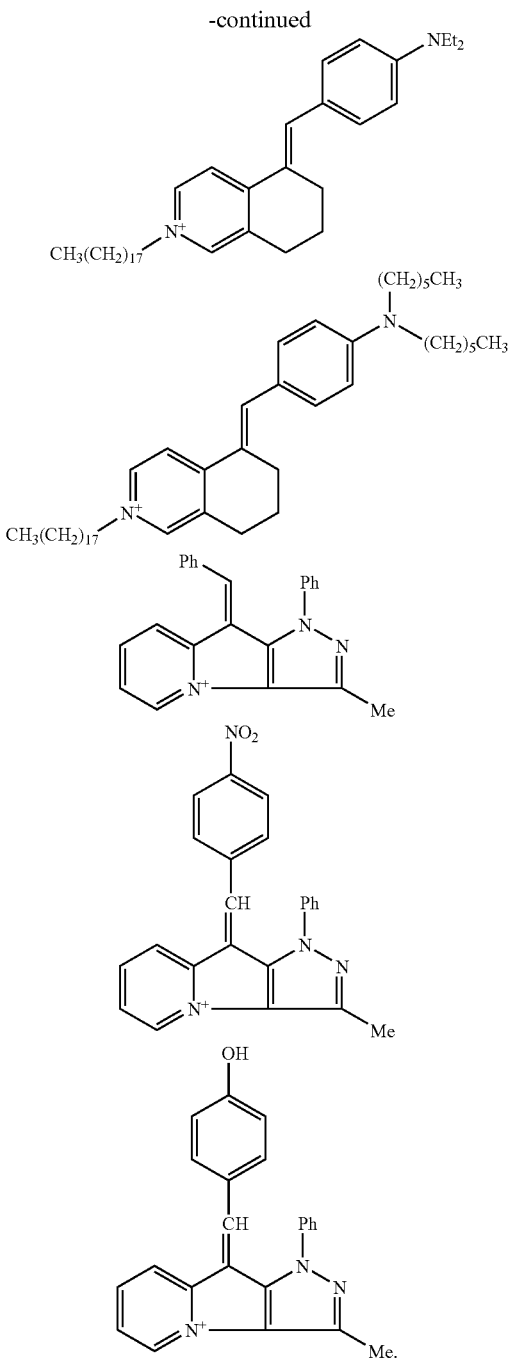

wherein the composition further comprises at least one surfactant.

24. The composition according to claim 23, wherein the at least one direct dye is present in an amount ranging from 0.01% to 20% by weight relative to the total weight of the composition.

25. The composition according to claim 24, wherein the at least one direct dye is present in an amount ranging from 0.1% to 5% by weight relative to the total weight of the composition.

26. The composition according to claim 23, wherein the cosmetically acceptable medium comprises water or a mixture of water and at least one organic solvent.

27. The composition according to claim 23, further comprising at least one additional direct dye of nonionic, cationic or anionic nature.

28. The composition according to claim 27, wherein the at least one additional direct dye is chosen from nitrobenzene dyes, azo dyes, anthraquinone, naphthoquinone or benzoquinone dyes, indigoid dyes, triarylmethane-based dyes and natural dyes, and mixtures thereof.

29. The composition according to claim 27, wherein the at least one additional direct dye is present in an amount ranging from 0.0005% to 12% by weight relative to the total weight of the composition.

30. The composition according to claim 23, further comprising at least one surfactant is nonionic.

31. The composition according to claim 23, wherein the at least one surfactant is present in an amount ranging from 0.01% to 50% by weight relative to the total weight of the composition.

32. The composition according to claim 23, further comprising at least one non-associative thickening polymer.

33. The composition according to claim 32, wherein the at least one non-associative thickening polymer is chosen from crosslinked acrylic acid homopolymers, crosslinked 2-acrylamido-2-methylpropanesulfonic acid homopolymers and the crosslinked acrylamide copolymers thereof, ammonium acrylate homopolymers or copolymers of ammonium acrylate and of acrylamide, nonionic guar gums, biopolysaccharide gums of microbial origin, gums originating from plant exudates, hydroxypropyl- or carboxymethylcelluloses; pectins and alginates, alone or as mixtures.

34. The composition according to claim 23, further comprising at least one associative thickening polymer.

35. The composition according to claim 34, wherein the at least one associative thickening polymer is chosen from associative polyurethanes, associative cellulose derivatives, associative vinyllactams, associative unsaturated polyacids, associative aminoplast-ethers, crosslinked 2-acrylamido-2-methylpropanesulfonic acid homopolymers and crosslinked acrylamide copolymers thereof, associative polymers or copolymers comprising at least one ethylenically unsaturated monomer containing a sulfonic group, alone or as mixtures.

36. The composition according to claim 35, wherein the at least one associative thickening polymer is chosen from cationic and nonionic polyurethanes and cationic and nonionic associative cellulose derivatives.

37. The composition according to claim 23, further comprising at least one associative or non-associative thickening polymer in an amount ranging from 0.01% to 10% by weight relative to the weight of the composition.

38. The composition according to claim 37, wherein the at least one associative or non-associative thickening polymer is present in an amount ranging from 0.1% to 5% by weight relative to the weight of the composition.

39. The composition according to claim 23, wherein the composition in the form of a coloring shampoo.

40. The composition according to claim 23, further comprising at least one oxidation base optionally combined with at least one coupler.

41. The composition according to claim 40, wherein the at least one oxidation base is chosen from para-phenylenediamines, bis-phenylalkylenediamines, para-aminophenols, ortho-aminophenols and heterocyclic bases, and the addition salts thereof with an acid or with an alkaline agent.

42. The composition according to claim 41, wherein the at least one oxidation base is present in an amount ranging from 0.0005% to 12% by weight relative to the total weight of the composition.

43. The composition according to claim 40, wherein the at least one coupler is chosen from meta-phenylenediamines, meta-aminophenols, meta-diphenols and heterocyclic couplers, and the addition salts thereof with an acid or with an alkaline agent.

44. The composition according to claim 43, wherein the at least one coupler is present in an amount ranging from 0.0001% to 10% by weight relative to the total weight of the dye composition.

45. The composition according to claim 23, further comprising at least one oxidizing agent.

46. The composition according to claim 45, wherein the at least one oxidizing agent is chosen from hydrogen peroxide, urea peroxide, alkali metal bromates, persalts, and enzymes.

47. The composition according to claim 46, wherein the at least one persalt is chosen from perborates and persulfates.

48. A multi-compartment device for dyeing and lightening the hair, comprising at least one compartment containing a composition, wherein the composition comprises:
  a cosmetically acceptable medium; and
in said medium, at least one direct dye or formula (I):
wherein:
  M and L, independently of each other, are chosen from $CR_7$, $CR_9$ and $N^+R_5$;
  K is chosen from a carbon atom and a quaternized nitrogen atom $N^+$;
  T is chosen from groups $N^+R_5$, groups $CR_4$ and a nitrogen atom;
  A is chosen from linear and branched alkylene groups $C_nH_{2n}$ comprising from 1 to 8 carbon atoms and optionally having at one end an oxygen atom or a carbonyl group; a group comprising at least one unsaturation, the unsaturation forming part of a benzene nucleus or of a heterocycle optionally substituted with at least one $C_1$-$C_4$ alkyl or $C_6$-$C_{30}$ aryl radical;
  $R_1$, $R_2$, $R_3$, $R_4$, $R_6$, $R_7$ and $R_9$, independently of each other, are chosen from hydrogen atoms; halogen atoms; $C_6$-$C_{30}$ aryl groups; hydroxyl groups; cyano groups; nitro groups; sulfo groups; amino groups; acylamino groups; di($C_1$-$C_6$)alkylamino groups; dihydroxy($C_1$-$C_6$)alkylamino groups; ($C_1$-$C_6$)alkylhydroxy($C_1$-$C_6$)alkylamino groups; ($C_1$-$C_6$)alkoxy groups; ($C_1$-$C_6$)alkoxycarbonyl groups; carboxy($C_1$-$C_6$)alkoxy groups; piperidinosulfonyl groups; pyrrolidino groups; ($C_1$-$C_6$)alkylhalo($C_1$-$C_6$)alkylamino groups; benzoyl($C_1$-$C_6$) alkyl groups; vinyl groups; formyl groups; $C_6$-$C_{30}$ aryl radicals optionally substituted with at least one group chosen from hydroxyl, linear, branched and cyclic $C_1$-$C_6$ alkoxy and linear, branched and cyclic alkyl groups comprising from 1 to 22 carbon atoms, itself being optionally substituted with at least one hydroxyl, amino or $C_1$-$C_6$ alkoxy group; linear, branched and cyclic alkyl radicals comprising from 1 to 22 carbon atoms, optionally substituted with at least one group chosen from hydroxyl, amino, linear, branched and cyclic $C_1$-$C_6$ alkoxy, optionally substituted aryl, carboxyl and sulfo groups and halogen atoms, this alkyl radical optionally being interrupted with a heteroatom;
  wherein two of the substituents $R_1$, $R_2$, $R_7$ and $R_9$, when M and L, respectively, are $CR_7$ and $CR_9$, may form with the carbon atoms to which they are attached an aromatic or non-aromatic $C_6$-$C_{30}$ ring or a 5- to 30-membered heterocyclic ring comprising from 1 to 5 heteroatoms; these rings being optionally condensed, optionally inserting a carbonyl group, and being optionally substituted with at least one group chosen from $C_1$-$C_4$ alkyl, ($C_1$-$C_4$)alkoxy ($C_1$-$C_4$)alkyl, amino, di($C_1$-$C_4$)alkylamino, halogen, phenyl, carboxyl and tri($C_1$-$C_4$)alkylammonio($C_1$-$C_4$) alkyl groups;
  $R_1$, $R_2$, $R_7$, and $R_9$ may also be chosen from groups identical to the part of the molecule condensed on the pyridinium nucleus so as to form a perfectly symmetrical molecule, thus comprising an acridinium sequence;
  two of the substituents $R_3$, $R_4$ and $R_6$ may form with the carbon atoms to which they are attached a ring chosen from a $C_6$-$C_{30}$ aromatic nucleus and a 5- to 30-membered heterocyclic nucleus comprising in total from 1 to 5 heteroatoms; this ring being optionally condensed, being optionally substituted with at least one group chosen from $C_1$-$C_4$ alkyl, ($C_1$-$C_4$)alkoxy($C_1$-$C_4$)alkyl, amino, di($C_1$-$C_4$)alkylamino, halogen, phenyl, carboxyl and tri($C_1$-$C_4$)-alkylammonio($C_1$-$C_4$)alkyl groups; and optionally forms with the optional substituent and the carbon atom bearing it a saturated or unsaturated, 5- to 10-membered ring;
  $R_5$ is chosen from linear, branched and cyclic alkyl radicals comprising from 1 to 22 carbon atoms, optionally substituted with at least one group chosen from hydroxyl, linear, branched or cyclic $C_1$-$C_6$ alkoxy, optionally substituted aryl, carboxyl and sulfo groups and halogen atoms, this alkyl radical being optionally interrupted with a heteroatom; and $C_6$-$C_{30}$ aryl radicals optionally substituted with at least one $C_1$-$C_4$ alkyl, $C_1$-$C_4$ alkoxy or hydroxyl radical;
  $R_5$ may form with the nitrogen atom bearing it and with one of the substituents $R_1$, $R_2$, $R_7$ and $R_9$ and the carbon atom bearing this substituent a 5- to 10-membered ring optionally substituted with an alkyl group; this ring may be optionally condensed with a benzene ring or with a ring formed by two of the remaining substituents and the carbon atoms bearing them;
  $X^-$ is chosen from organic and mineral anions;
wherein only one from among K, L and M can be $N^+R_5$ or $N^+$, and
at least one other compartment containing a composition containing at least one oxidizing agent.

\* \* \* \* \*

UNITED STATES PATENT AND TRADEMARK OFFICE
CERTIFICATE OF CORRECTION

PATENT NO.         : 7,531,008 B2
APPLICATION NO. : 11/606115
DATED               : May 12, 2009
INVENTOR(S)        : Alain Lagrange Page 1 of 1

It is certified that error appears in the above-identified patent and that said Letters Patent is hereby corrected as shown below:

Claim 48, col. 75, line 21, below "in said medium, at least one direct dye or formula (I):", insert:

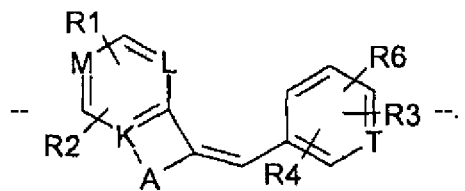

Signed and Sealed this

Eighteenth Day of August, 2009

David J. Kappos
*Director of the United States Patent and Trademark Office*